(12) United States Patent
Hacking et al.

(10) Patent No.: US 12,059,591 B2
(45) Date of Patent: Aug. 13, 2024

(54) BENDABLE SENSOR DEVICE FOR MONITORING JOINT EXTENSION AND FLEXION

(71) Applicant: ROM TECHNOLOGIES, INC., Brookfield, CT (US)

(72) Inventors: S. Adam Hacking, Nashua, NH (US); Daniel Lipszyc, Glasgow, MT (US)

(73) Assignee: ROM Technologies, Inc., Brookfield, CT (US)

( * ) Notice: Subject to any disclaimer, the term of this patent is extended or adjusted under 35 U.S.C. 154(b) by 103 days.

(21) Appl. No.: 17/551,975

(22) Filed: Dec. 15, 2021

(65) Prior Publication Data

US 2022/0105384 A1    Apr. 7, 2022

Related U.S. Application Data

(62) Division of application No. 16/675,753, filed on Nov. 6, 2019.
(Continued)

(51) Int. Cl.
*A63B 22/06* (2006.01)
*A61B 5/11* (2006.01)
(Continued)

(52) U.S. Cl.
CPC ........ *A63B 22/0605* (2013.01); *A61B 5/1121* (2013.01); *A61B 5/221* (2013.01);
(Continued)

(58) Field of Classification Search
CPC .......... A63B 22/0605; A63B 21/00072; A63B 21/00178; A63B 21/00181;
(Continued)

(56) References Cited

U.S. PATENT DOCUMENTS

| 59,915 A | 11/1866 | Lallement |
|---|---|---|
| 363,522 A | 5/1887 | Knous |

(Continued)

FOREIGN PATENT DOCUMENTS

| CA | 3193419 A1 | 3/2022 |
|---|---|---|
| CN | 2885238 Y | 4/2007 |

(Continued)

OTHER PUBLICATIONS

Malloy, Online Article "AI-enabled EKGs find difference between numerical age and biological age significantly affects health, longevity", Website: https://newsnetwork.mayoclinic.org/discussion/ai-enabled-ekgs-find-difference-between-numerical-age-and-biological-age-significantly-affects-health-longevity/, Mayo Clinic News Network, May 20, 2021, retrieved: Jan. 23, 2023, p. 1-4.

(Continued)

*Primary Examiner* — Sundhara M Ganesan
(74) *Attorney, Agent, or Firm* — Dickinson Wright PLLC; Stephen A. Mason; Jonathan H. Harder

(57) ABSTRACT

A system for rehabilitation is disclosed. The system for rehabilitation includes one or more electronic devices comprising one or more memory devices storing instructions, one or more network interface cards, and one or more sensors, wherein the one or more electronic devices are coupled to a user. The system for rehabilitation further includes one or more processing devices operatively coupled to the one or more memory devices, the one or more network interface cards, and the one or more sensors. The one or more processing devices are configured to execute the instructions to receive information from the one or more sensors. The one or more processing devices are further configured to execute the instructions to transmit the information to a computing device controlling an electromechanical device, via the one or more network interface cards.

5 Claims, 37 Drawing Sheets

Related U.S. Application Data

(60) Provisional application No. 62/816,503, filed on Mar. 11, 2019.

(51) Int. Cl.

| | |
|---|---|
| *A61B 5/22* | (2006.01) |
| *A61H 1/02* | (2006.01) |
| *A63B 21/00* | (2006.01) |
| *A63B 21/005* | (2006.01) |
| *A63B 24/00* | (2006.01) |
| *A63B 71/00* | (2006.01) |
| *G06F 3/04817* | (2022.01) |
| *G06F 3/0482* | (2013.01) |
| *G16H 20/30* | (2018.01) |
| *H04N 23/60* | (2023.01) |
| *A61B 5/00* | (2006.01) |
| *A63B 22/00* | (2006.01) |
| *A63B 71/06* | (2006.01) |
| *G06F 3/04847* | (2022.01) |

(52) U.S. Cl.
CPC ..... *A61H 1/0214* (2013.01); *A63B 21/00072* (2013.01); *A63B 21/00178* (2013.01); *A63B 21/00181* (2013.01); *A63B 21/0058* (2013.01); *A63B 21/4034* (2015.10); *A63B 24/0062* (2013.01); *A63B 24/0075* (2013.01); *A63B 71/0054* (2013.01); *G06F 3/04817* (2013.01); *G06F 3/0482* (2013.01); *G16H 20/30* (2018.01); *H04N 23/60* (2023.01); *A61B 5/4824* (2013.01); *A61B 5/6812* (2013.01); *A63B 2022/0094* (2013.01); *A63B 2024/0068* (2013.01); *A63B 2024/0093* (2013.01); *A63B 2024/0096* (2013.01); *A63B 2071/0081* (2013.01); *A63B 71/0622* (2013.01); *A63B 2071/0647* (2013.01); *A63B 2071/0658* (2013.01); *A63B 2071/0675* (2013.01); *A63B 2209/08* (2013.01); *A63B 2220/17* (2013.01); *A63B 2220/24* (2013.01); *A63B 2220/40* (2013.01); *A63B 2220/51* (2013.01); *A63B 2220/807* (2013.01); *A63B 2220/833* (2013.01); *A63B 2220/836* (2013.01); *A63B 2225/096* (2013.01); *A63B 2225/20* (2013.01); *A63B 2225/52* (2013.01); *G06F 3/04847* (2013.01)

(58) Field of Classification Search
CPC ............ A63B 21/0058; A63B 21/4034; A63B 24/0062; A63B 24/0075; A63B 71/0054; A63B 71/0622; A63B 2022/0094; A63B 2024/0068; A63B 2024/0093; A63B 2024/0096; A63B 2071/0081; A63B 2071/0647; A63B 2071/0658; A63B 2071/0675; A63B 2209/08; A63B 2220/17; A63B 2220/24; A63B 2220/40; A63B 2220/51; A63B 2220/807; A63B 2220/833; A63B 2220/836; A63B 2225/096; A63B 2225/20; A63B 2225/52; A63B 2071/065; A63B 2220/62; A63B 2230/06; A63B 21/0059; A63B 21/157; A63B 23/0476; A63B 24/0087; A63B 2022/0623; A63B 2024/0071; A63B 2071/0625; A63B 2071/0655; A63B 2209/10; A63B 2210/50; A63B 2220/05; A63B 2220/20; A63B 2220/805; A63B 2225/09; A63B 2225/50; A63B 2225/74; A63B 2230/207; A61B 5/1121; A61B 5/221; A61B 5/4824; A61B 5/6812; A61B 5/0077; A61B 5/4585; A61B 5/021; A61B 5/02416; A61B 5/14551; A61B 5/6895; A61B 5/743; A61B 2562/0219; A61B 5/0022; A61B 5/0205; A61B 5/681; A61B 5/7435; A61B 2505/09; A61H 1/0214; A61H 1/00; G06F 3/04817; G06F 3/0482; G06F 3/04847; G16H 20/30; G16H 40/67; H04N 23/60; H04N 23/661; G06N 3/02

See application file for complete search history.

(56) References Cited

U.S. PATENT DOCUMENTS

| | | |
|---|---|---|
| 446,671 A | 2/1891 | Elliot |
| 631,276 A | 3/1898 | Bulova |
| 610,157 A | 8/1898 | Campbell |
| 823,712 A | 6/1906 | Uhlmann |
| 1,149,029 A | 8/1915 | Clark |
| 1,227,743 A | 5/1917 | Burgedorff |
| 1,784,230 A | 12/1930 | Freeman |
| 3,081,645 A | 3/1963 | Bergfors |
| 3,100,640 A | 8/1963 | Weitzel |
| 3,137,014 A | 6/1964 | Meucci |
| 3,143,316 A | 8/1964 | Shapiro |
| 3,713,438 A | 1/1973 | Knutsen |
| 3,744,480 A | 7/1973 | Gause et al. |
| 3,888,136 A | 6/1975 | Lapeyre |
| 4,079,957 A | 3/1978 | Blease |
| 4,408,613 A | 10/1983 | Relyea |
| 4,436,097 A | 3/1984 | Cunningham |
| 4,446,753 A | 5/1984 | Nagano |
| 4,477,072 A | 10/1984 | DeCloux |
| 4,499,900 A | 2/1985 | Petrofsky et al. |
| 4,509,742 A | 4/1985 | Cones |
| 4,606,241 A | 8/1986 | Fredriksson |
| 4,611,807 A | 9/1986 | Castillo |
| 4,616,823 A | 10/1986 | Yang |
| 4,648,287 A | 3/1987 | Preskitt |
| 4,673,178 A | 6/1987 | Dwight |
| 4,822,032 A | 4/1989 | Whitmore et al. |
| 4,824,104 A | 4/1989 | Bloch |
| 4,850,245 A | 7/1989 | Feamster et al. |
| 4,858,942 A | 8/1989 | Rodriguez |
| 4,869,497 A | 9/1989 | Stewart et al. |
| 4,915,374 A | 4/1990 | Watkins |
| 4,930,768 A | 6/1990 | Lapcevic |
| 4,932,650 A | 6/1990 | Bingham et al. |
| 4,961,570 A | 10/1990 | Chang |
| 5,137,501 A | 8/1992 | Mertesdorf |
| 5,161,430 A | 11/1992 | Febey |
| 5,202,794 A | 4/1993 | Schnee et al. |
| 5,240,417 A | 8/1993 | Smithson et al. |
| 5,247,853 A | 9/1993 | Dalebout |
| 5,256,115 A | 10/1993 | Scholder et al. |
| 5,256,117 A | 10/1993 | Potts et al. |
| D342,299 S | 12/1993 | Birrell et al. |
| 5,282,748 A | 2/1994 | Little |
| 5,284,131 A | 2/1994 | Gray |
| 5,316,532 A | 5/1994 | Butler |
| 5,318,487 A | 6/1994 | Golen |
| 5,324,241 A | 6/1994 | Artigues et al. |
| 5,336,147 A | 8/1994 | Sweeney, III |
| 5,338,272 A | 8/1994 | Sweeney, III |
| 5,356,356 A | 10/1994 | Hildebrandt |
| 5,361,649 A | 11/1994 | Slocum, Jr. |
| D353,421 S | 12/1994 | Gallivan |
| D359,777 S | 6/1995 | Hildebrandt |
| 5,429,140 A | 7/1995 | Burdea et al. |
| 5,458,022 A | 10/1995 | Mattfeld et al. |
| 5,487,713 A | 1/1996 | Butler |
| 5,566,589 A | 10/1996 | Buck |
| 5,580,338 A | 12/1996 | Scelta et al. |
| 5,676,349 A | 10/1997 | Wilson |
| 5,685,804 A | 11/1997 | Whan-Tong et al. |
| 5,738,636 A | 4/1998 | Saringer et al. |

(56) References Cited

U.S. PATENT DOCUMENTS

| | | |
|---|---|---|
| 5,860,941 A | 1/1999 | Saringer et al. |
| 5,950,813 A | 9/1999 | Hoskins et al. |
| 6,007,459 A | 12/1999 | Burgess |
| D421,075 S | 2/2000 | Hildebrandt |
| 6,053,847 A | 4/2000 | Stearns et al. |
| 6,077,201 A | 6/2000 | Cheng |
| 6,102,834 A | 8/2000 | Chen |
| 6,110,130 A | 8/2000 | Kramer |
| 6,155,958 A | 12/2000 | Goldberg |
| 6,162,189 A | 12/2000 | Girone et al. |
| 6,182,029 B1 | 1/2001 | Friedman |
| D438,580 S | 3/2001 | Shaw |
| 6,253,638 B1 | 7/2001 | Bermudez |
| 6,267,735 B1 | 7/2001 | Blanchard et al. |
| 6,273,863 B1 | 8/2001 | Avni et al. |
| D450,100 S | 11/2001 | Hsu |
| D450,101 S | 11/2001 | Hsu |
| D451,972 S | 12/2001 | Easley |
| D452,285 S | 12/2001 | Easley |
| D454,605 S | 3/2002 | Lee |
| 6,371,891 B1 | 4/2002 | Speas |
| D459,776 S | 7/2002 | Lee |
| 6,413,190 B1 | 7/2002 | Wood et al. |
| 6,430,436 B1 | 8/2002 | Richter |
| 6,436,058 B1 | 8/2002 | Krahner et al. |
| 6,450,923 B1 | 9/2002 | Vatti |
| 6,474,193 B1 | 11/2002 | Farney |
| 6,491,649 B1 | 12/2002 | Ombrellaro |
| 6,514,085 B2 | 2/2003 | Slattery et al. |
| 6,535,861 B1 | 3/2003 | OConnor et al. |
| 6,543,309 B2 | 4/2003 | Heim |
| D475,424 S | 6/2003 | Lee |
| 6,589,139 B1 | 7/2003 | Butterworth |
| 6,601,016 B1 | 7/2003 | Brown et al. |
| 6,602,191 B2 | 8/2003 | Quy |
| 6,613,000 B1 | 9/2003 | Reinkensmeyer et al. |
| 6,626,800 B1 | 9/2003 | Casler |
| 6,626,805 B1 | 9/2003 | Lightbody |
| 6,640,122 B2 | 10/2003 | Manoli |
| D482,416 S | 11/2003 | Yang |
| 6,640,662 B1 | 11/2003 | Baxter |
| 6,652,425 B1 | 11/2003 | Martin et al. |
| D484,931 S | 1/2004 | Tsai |
| 6,820,517 B1 | 11/2004 | Farney |
| 6,865,969 B2 | 3/2005 | Stevens |
| 6,890,312 B1 | 5/2005 | Priester et al. |
| 6,895,834 B1 | 5/2005 | Baatz |
| 6,902,513 B1 | 6/2005 | McClure |
| 7,058,453 B2 | 6/2006 | Nelson et al. |
| 7,063,643 B2 | 6/2006 | Arai |
| 7,156,665 B1 | 1/2007 | OConnor et al. |
| 7,156,780 B1 | 1/2007 | Fuchs et al. |
| 7,169,085 B1 | 1/2007 | Killin et al. |
| 7,204,788 B2 | 4/2007 | Andrews |
| 7,209,886 B2 | 4/2007 | Kimmel |
| 7,226,394 B2 | 6/2007 | Johnson |
| RE39,904 E | 10/2007 | Lee |
| 7,406,003 B2 | 7/2008 | Burkhardt et al. |
| D575,836 S | 8/2008 | Hsiao |
| 7,507,188 B2 | 3/2009 | Nurre |
| 7,594,879 B2 | 9/2009 | Johnson |
| 7,628,730 B1 | 12/2009 | Watterson et al. |
| D610,635 S | 2/2010 | Hildebrandt |
| 7,726,034 B2 | 6/2010 | Wixey |
| 7,778,851 B2 | 8/2010 | Schoenberg et al. |
| 7,809,601 B2 | 10/2010 | Shaya et al. |
| 7,815,551 B2 | 10/2010 | Merli |
| 7,833,135 B2 | 11/2010 | Radow et al. |
| 7,837,472 B1 | 11/2010 | Elsmore et al. |
| 7,955,219 B2 | 6/2011 | Birrell et al. |
| 7,969,315 B1 | 6/2011 | Ross et al. |
| 7,988,599 B2 | 8/2011 | Ainsworth et al. |
| 8,012,107 B2 | 9/2011 | Einav et al. |
| 8,021,270 B2 | 9/2011 | D'Eredita |
| 8,038,578 B2 | 10/2011 | Olrik et al. |
| 8,079,937 B2 | 12/2011 | Bedell |
| 8,113,991 B2 | 2/2012 | Kutliroff |
| 8,177,732 B2 | 5/2012 | Einav et al. |
| 8,287,434 B2 | 10/2012 | Zavadsky et al. |
| 8,298,123 B2 | 10/2012 | Hickman |
| 8,371,990 B2 | 2/2013 | Shea |
| 8,419,593 B2 | 4/2013 | Ainsworth et al. |
| 8,465,398 B2 | 6/2013 | Lee et al. |
| 8,506,458 B2 | 8/2013 | Dugan |
| 8,515,777 B1 | 8/2013 | Rajasenan |
| 8,540,515 B2 | 9/2013 | Williams et al. |
| 8,540,516 B2 | 9/2013 | Williams et al. |
| 8,556,778 B1 | 10/2013 | Dugan |
| 8,607,465 B1 | 12/2013 | Edwards |
| 8,613,689 B2 | 12/2013 | Dyer et al. |
| 8,672,812 B2 | 3/2014 | Dugan |
| 8,751,264 B2 | 6/2014 | Beraja et al. |
| 8,784,273 B2 | 7/2014 | Dugan |
| 8,823,448 B1 | 9/2014 | Shen |
| 8,845,493 B2 | 9/2014 | Watterson et al. |
| 8,849,681 B2 | 9/2014 | Hargrove et al. |
| 8,864,628 B2 | 10/2014 | Boyette et al. |
| 8,893,287 B2 | 11/2014 | Gjonej et al. |
| 8,911,327 B1 | 12/2014 | Boyette |
| 8,979,711 B2 | 3/2015 | Dugan |
| 9,004,598 B2 | 4/2015 | Weber |
| 9,044,630 B1 | 6/2015 | Lampert et al. |
| 9,167,281 B2 | 10/2015 | Petrov et al. |
| D744,050 S | 11/2015 | Colburn |
| 9,248,071 B1 | 2/2016 | Brenda |
| 9,272,185 B2 | 3/2016 | Dugan |
| 9,283,434 B1 | 3/2016 | Wu |
| 9,311,789 B1 | 4/2016 | Gwin |
| 9,312,907 B2 | 4/2016 | Auchinleck et al. |
| 9,367,668 B2 | 6/2016 | Flynt et al. |
| 9,409,054 B2 | 8/2016 | Dugan |
| 9,443,205 B2 | 9/2016 | Wall |
| 9,474,935 B2 | 10/2016 | Abbondanza et al. |
| 9,480,873 B2 | 11/2016 | Chuang |
| 9,481,428 B2 | 11/2016 | Gros |
| 9,514,277 B2 | 12/2016 | Hassing et al. |
| 9,566,472 B2 | 2/2017 | Dugan |
| 9,579,056 B2 | 2/2017 | Rosenbek et al. |
| 9,629,558 B2 | 4/2017 | Yuen et al. |
| 9,640,057 B1 | 5/2017 | Ross |
| 9,707,147 B2 | 7/2017 | Levital et al. |
| 9,713,744 B2 | 7/2017 | Suzuki |
| D793,494 S | 8/2017 | Mansfield et al. |
| D794,142 S | 8/2017 | Zhou |
| 9,717,947 B2 | 8/2017 | Lin |
| 9,737,761 B1 | 8/2017 | Govindarajan |
| 9,757,612 B2 | 9/2017 | Weber |
| 9,782,621 B2 | 10/2017 | Chiang et al. |
| 9,802,076 B2 | 10/2017 | Murray et al. |
| 9,802,081 B2 | 10/2017 | Ridgel et al. |
| 9,813,239 B2 | 11/2017 | Chee et al. |
| 9,826,908 B2 | 11/2017 | Wu |
| 9,827,445 B2 | 11/2017 | Marcos et al. |
| 9,849,337 B2 | 12/2017 | Roman et al. |
| 9,868,028 B2 | 1/2018 | Shin |
| 9,872,087 B2 | 1/2018 | DelloStritto et al. |
| 9,872,637 B2 | 1/2018 | Kording et al. |
| 9,914,053 B2 | 3/2018 | Dugan |
| 9,919,198 B2 | 3/2018 | Romeo et al. |
| 9,937,382 B2 | 4/2018 | Dugan |
| 9,939,784 B1 | 4/2018 | Berardinelli |
| 9,977,587 B2 | 5/2018 | Mountain |
| 9,993,181 B2 | 6/2018 | Ross |
| 10,004,946 B2 | 6/2018 | Ross |
| D826,349 S | 8/2018 | Oblamski |
| 10,055,550 B2 | 8/2018 | Goetz |
| 10,058,473 B2 | 8/2018 | Oshima et al. |
| 10,074,148 B2 | 9/2018 | Cashman et al. |
| 10,089,443 B2 | 10/2018 | Miller et al. |
| 10,111,643 B2 | 10/2018 | Shulhauser et al. |
| 10,137,328 B2 | 11/2018 | Baudhuin |
| 10,143,395 B2 | 12/2018 | Chakravarthy et al. |
| 10,155,134 B2 | 12/2018 | Dugan |
| 10,159,872 B2 | 12/2018 | Sasaki et al. |

(56) References Cited

U.S. PATENT DOCUMENTS

| | | |
|---|---|---|
| 10,173,094 B2 | 1/2019 | Gomberg |
| 10,173,095 B2 | 1/2019 | Gomberg et al. |
| 10,173,096 B2 | 1/2019 | Gomberg et al. |
| 10,173,097 B2 | 1/2019 | Gomberg et al. |
| 10,198,928 B1 | 2/2019 | Ross et al. |
| 10,226,663 B2 | 3/2019 | Gomberg et al. |
| 10,231,664 B2 | 3/2019 | Ganesh |
| 10,244,990 B2 | 4/2019 | Hu et al. |
| 10,258,823 B2 | 4/2019 | Cole |
| 10,325,070 B2 | 6/2019 | Beale et al. |
| 10,327,697 B1 | 6/2019 | Stein et al. |
| 10,369,021 B2 | 8/2019 | Zoss et al. |
| 10,380,866 B1 | 8/2019 | Ross et al. |
| 10,413,238 B1 | 9/2019 | Cooper |
| 10,424,033 B2 | 9/2019 | Romeo |
| 10,430,552 B2 | 10/2019 | Mihai |
| D866,957 S | 11/2019 | Ross et al. |
| 10,468,131 B2 | 11/2019 | Macoviak et al. |
| 10,475,323 B1 | 11/2019 | Ross |
| 10,475,537 B2 | 11/2019 | Purdie et al. |
| 10,492,977 B2 | 12/2019 | Kapure et al. |
| 10,507,358 B2 | 12/2019 | Kinnunen et al. |
| 10,542,914 B2 | 1/2020 | Forth et al. |
| 10,546,467 B1 | 1/2020 | Luciano, Jr. et al. |
| 10,569,122 B2 | 2/2020 | Johnson |
| 10,572,626 B2 | 2/2020 | Balram |
| 10,576,331 B2 | 3/2020 | Kuo |
| 10,581,896 B2 | 3/2020 | Nachenberg |
| 10,625,114 B2 | 4/2020 | Ercanbrack |
| 10,646,746 B1 | 5/2020 | Gomberg et al. |
| 10,660,534 B2 | 5/2020 | Lee et al. |
| 10,678,890 B2 | 6/2020 | Bitran et al. |
| 10,685,092 B2 | 6/2020 | Paparella et al. |
| 10,777,200 B2 | 9/2020 | Will et al. |
| D899,605 S | 10/2020 | Ross et al. |
| 10,792,495 B2 | 10/2020 | Izvorski et al. |
| 10,867,695 B2 | 12/2020 | Neagle |
| 10,874,905 B2 | 12/2020 | Belson et al. |
| D907,143 S | 1/2021 | Ach et al. |
| 10,881,911 B2 | 1/2021 | Kwon et al. |
| 10,918,332 B2 | 2/2021 | Belson et al. |
| 10,931,643 B1 | 2/2021 | Neumann |
| 10,987,176 B2 | 4/2021 | Poltaretskyi et al. |
| 10,991,463 B2 | 4/2021 | Kutzko et al. |
| 11,000,735 B2 | 5/2021 | Orady et al. |
| 11,040,238 B2 | 6/2021 | Colburn |
| 11,045,709 B2 | 6/2021 | Putnam |
| 11,065,170 B2 | 7/2021 | Yang et al. |
| 11,065,527 B2 | 7/2021 | Putnam |
| 11,069,436 B2 | 7/2021 | Mason et al. |
| 11,071,597 B2 | 7/2021 | Posnack et al. |
| 11,075,000 B2 | 7/2021 | Mason et al. |
| D928,635 S | 8/2021 | Hacking et al. |
| 11,087,865 B2 | 8/2021 | Mason et al. |
| 11,101,028 B2 | 8/2021 | Mason et al. |
| 11,107,591 B1 | 8/2021 | Mason |
| 11,139,060 B2 | 10/2021 | Mason et al. |
| 11,185,735 B2 | 11/2021 | Arn et al. |
| D939,096 S | 12/2021 | Lee |
| D939,644 S | 12/2021 | Ach et al. |
| D940,797 S | 1/2022 | Ach et al. |
| D940,891 S | 1/2022 | Lee |
| 11,229,727 B2 | 1/2022 | Tatonetti |
| 11,270,795 B2 | 3/2022 | Mason et al. |
| 11,272,879 B2 | 3/2022 | Wiedenhoefer et al. |
| 11,278,766 B2 | 3/2022 | Lee |
| 11,282,599 B2 | 3/2022 | Mason et al. |
| 11,282,604 B2 | 3/2022 | Mason et al. |
| 11,282,608 B2 | 3/2022 | Mason et al. |
| 11,284,797 B2 | 3/2022 | Mason et al. |
| D948,639 S | 4/2022 | Ach et al. |
| 11,295,848 B2 | 4/2022 | Mason et al. |
| 11,298,284 B2 | 4/2022 | Bayerlein |
| 11,309,085 B2 | 4/2022 | Mason et al. |
| 11,317,975 B2 | 5/2022 | Mason et al. |
| 11,325,005 B2 | 5/2022 | Mason et al. |
| 11,328,807 B2 | 5/2022 | Mason et al. |
| 11,337,648 B2 | 5/2022 | Mason |
| 11,348,683 B2 | 5/2022 | Guaneri et al. |
| 11,376,470 B2 | 7/2022 | Weldemariam |
| 11,404,150 B2 | 8/2022 | Guaneri et al. |
| 11,410,768 B2 | 8/2022 | Mason et al. |
| 11,422,841 B2 | 8/2022 | Jeong |
| 11,495,355 B2 | 11/2022 | McNutt et al. |
| 11,508,258 B2 | 11/2022 | Nakashima et al. |
| 11,508,482 B2 | 11/2022 | Mason et al. |
| 11,515,021 B2 | 11/2022 | Mason |
| 11,515,028 B2 | 11/2022 | Mason |
| 11,524,210 B2 | 12/2022 | Kim et al. |
| 11,527,326 B2 | 12/2022 | McNair et al. |
| 11,532,402 B2 | 12/2022 | Farley et al. |
| 11,534,654 B2 | 12/2022 | Silcock et al. |
| D976,339 S | 1/2023 | Li |
| 11,541,274 B2 | 1/2023 | Hacking |
| 11,636,944 B2 | 4/2023 | Hanrahan et al. |
| 11,663,673 B2 | 5/2023 | Pyles |
| 11,701,548 B2 | 7/2023 | Posnack et al. |
| 2001/0044573 A1 | 11/2001 | Manoli |
| 2002/0072452 A1 | 6/2002 | Torkelson |
| 2002/0143279 A1 | 10/2002 | Porter et al. |
| 2002/0160883 A1 | 10/2002 | Dugan |
| 2002/0183599 A1 | 12/2002 | Castellanos |
| 2003/0013072 A1 | 1/2003 | Thomas |
| 2003/0036683 A1 | 2/2003 | Kehr et al. |
| 2003/0045402 A1 | 3/2003 | Pyle |
| 2003/0064863 A1 | 4/2003 | Chen |
| 2003/0083596 A1 | 5/2003 | Kramer |
| 2003/0092536 A1 | 5/2003 | Romanelli |
| 2003/0109814 A1 | 6/2003 | Rummerfield |
| 2003/0181832 A1 | 9/2003 | Carnahan et al. |
| 2004/0102931 A1 | 5/2004 | Ellis et al. |
| 2004/0106502 A1 | 6/2004 | Sher |
| 2004/0147969 A1 | 7/2004 | Mann et al. |
| 2004/0172093 A1 | 9/2004 | Rummerfield |
| 2004/0194572 A1 | 10/2004 | Kim |
| 2004/0204959 A1 | 10/2004 | Moreano et al. |
| 2005/0015118 A1 | 1/2005 | Davis et al. |
| 2005/0020411 A1 | 1/2005 | Andrews |
| 2005/0043153 A1 | 2/2005 | Krietzman |
| 2005/0049122 A1 | 3/2005 | Vallone et al. |
| 2005/0085346 A1 | 4/2005 | Johnson |
| 2005/0085353 A1 | 4/2005 | Johnson |
| 2005/0115561 A1 | 6/2005 | Stahmann |
| 2005/0274220 A1 | 12/2005 | Reboullet |
| 2006/0003871 A1 | 1/2006 | Houghton et al. |
| 2006/0046905 A1 | 3/2006 | Doody et al. |
| 2006/0058648 A1 | 3/2006 | Meier |
| 2006/0064136 A1 | 3/2006 | Wang |
| 2006/0064329 A1 | 3/2006 | Abolfathi et al. |
| 2006/0199700 A1 | 9/2006 | LaStayo et al. |
| 2006/0247095 A1 | 11/2006 | Rummerfield |
| 2007/0042868 A1 | 2/2007 | Fisher et al. |
| 2007/0118389 A1 | 5/2007 | Shipon |
| 2007/0137307 A1 | 6/2007 | Gruben et al. |
| 2007/0173392 A1 | 7/2007 | Stanford |
| 2007/0184414 A1 | 8/2007 | Perez |
| 2007/0194939 A1 | 8/2007 | Alvarez et al. |
| 2007/0219059 A1 | 9/2007 | Schwartz |
| 2007/0287597 A1 | 12/2007 | Cameron |
| 2008/0021834 A1 | 1/2008 | Holla et al. |
| 2008/0082356 A1 | 4/2008 | Friedlander et al. |
| 2008/0096726 A1 | 4/2008 | Riley et al. |
| 2008/0153592 A1 | 6/2008 | James-Herbert |
| 2008/0161166 A1 | 7/2008 | Lo |
| 2008/0161733 A1 | 7/2008 | Einav et al. |
| 2008/0221485 A1 | 9/2008 | Lissek et al. |
| 2008/0281633 A1 | 11/2008 | Burdea et al. |
| 2008/0300914 A1 | 12/2008 | Karkanias et al. |
| 2009/0011907 A1 | 1/2009 | Radow et al. |
| 2009/0058635 A1 | 3/2009 | LaLonde et al. |
| 2009/0070138 A1 | 3/2009 | Langheier et al. |
| 2009/0211395 A1 | 8/2009 | Mule |
| 2009/0270227 A1 | 10/2009 | Ashby et al. |
| 2009/0287503 A1 | 11/2009 | Angell et al. |

(56) References Cited

U.S. PATENT DOCUMENTS

| | | |
|---|---|---|
| 2009/0299766 A1 | 12/2009 | Friedlander et al. |
| 2010/0048358 A1 | 2/2010 | Tchao et al. |
| 2010/0076786 A1 | 3/2010 | Dalton et al. |
| 2010/0121160 A1 | 5/2010 | Stark et al. |
| 2010/0173747 A1 | 7/2010 | Chen et al. |
| 2010/0216168 A1 | 8/2010 | Heinzman et al. |
| 2010/0248899 A1 | 9/2010 | Bedell et al. |
| 2010/0248905 A1 | 9/2010 | Lu |
| 2010/0268304 A1 | 10/2010 | Matos |
| 2010/0298102 A1 | 11/2010 | Bosecker et al. |
| 2010/0326207 A1 | 12/2010 | Topel |
| 2011/0010188 A1 | 1/2011 | Yoshikawa et al. |
| 2011/0047108 A1 | 2/2011 | Chakrabarty et al. |
| 2011/0119212 A1 | 5/2011 | De Bruin et al. |
| 2011/0172059 A1 | 7/2011 | Watterson et al. |
| 2011/0195819 A1 | 8/2011 | Shaw et al. |
| 2011/0218814 A1 | 9/2011 | Coats |
| 2011/0275483 A1 | 11/2011 | Dugan |
| 2011/0306846 A1 | 12/2011 | Osorio |
| 2012/0041771 A1 | 2/2012 | Cosentino et al. |
| 2012/0065987 A1 | 3/2012 | Farooq et al. |
| 2012/0116258 A1 | 5/2012 | Lee |
| 2012/0167709 A1 | 7/2012 | Chen et al. |
| 2012/0183939 A1 | 7/2012 | Aragones et al. |
| 2012/0190502 A1 | 7/2012 | Paulus et al. |
| 2012/0232438 A1 | 9/2012 | Cataldi et al. |
| 2012/0259648 A1 | 10/2012 | Mallon et al. |
| 2012/0295240 A1 | 11/2012 | Walker et al. |
| 2012/0296455 A1 | 11/2012 | Ohnemus et al. |
| 2012/0310667 A1 | 12/2012 | Altman et al. |
| 2013/0123071 A1 | 5/2013 | Rhea |
| 2013/0123667 A1 | 5/2013 | Komatireddy et al. |
| 2013/0137550 A1 | 5/2013 | Skinner et al. |
| 2013/0178334 A1 | 7/2013 | Brammer |
| 2013/0211281 A1 | 8/2013 | Ross et al. |
| 2013/0253943 A1 | 9/2013 | Lee et al. |
| 2013/0274069 A1 | 10/2013 | Watterson et al. |
| 2013/0296987 A1 | 11/2013 | Rogers et al. |
| 2013/0318027 A1 | 11/2013 | Almogy et al. |
| 2013/0332616 A1 | 12/2013 | Landwehr |
| 2013/0345025 A1 | 12/2013 | van der Merwe |
| 2014/0006042 A1 | 1/2014 | Keefe et al. |
| 2014/0011640 A1 | 1/2014 | Dugan |
| 2014/0073486 A1 | 3/2014 | Ahmed et al. |
| 2014/0089836 A1 | 3/2014 | Damani et al. |
| 2014/0113768 A1 | 4/2014 | Lin et al. |
| 2014/0155129 A1 | 6/2014 | Dugan |
| 2014/0172442 A1 | 6/2014 | Broderick |
| 2014/0172460 A1 | 6/2014 | Kohli |
| 2014/0188009 A1 | 7/2014 | Lange et al. |
| 2014/0194250 A1 | 7/2014 | Reich et al. |
| 2014/0194251 A1 | 7/2014 | Reich et al. |
| 2014/0207264 A1 | 7/2014 | Quy |
| 2014/0207486 A1 | 7/2014 | Carty et al. |
| 2014/0228649 A1 | 8/2014 | Rayner et al. |
| 2014/0246499 A1 | 9/2014 | Proud et al. |
| 2014/0256511 A1 | 9/2014 | Smith |
| 2014/0257837 A1 | 9/2014 | Walker et al. |
| 2014/0274565 A1 | 9/2014 | Boyette et al. |
| 2014/0274622 A1 | 9/2014 | Leonhard |
| 2014/0303540 A1 | 10/2014 | Baym |
| 2014/0309083 A1 | 10/2014 | Dugan |
| 2014/0315689 A1 | 10/2014 | Vauquelin et al. |
| 2014/0322686 A1 | 10/2014 | Kang |
| 2014/0371816 A1 | 12/2014 | Matos |
| 2015/0025816 A1 | 1/2015 | Ross |
| 2015/0045700 A1 | 2/2015 | Cavanagh et al. |
| 2015/0073814 A1 | 3/2015 | Linebaugh |
| 2015/0088544 A1 | 3/2015 | Goldberg |
| 2015/0094192 A1 | 4/2015 | Skwortsow et al. |
| 2015/0099458 A1 | 4/2015 | Weisner et al. |
| 2015/0099952 A1 | 4/2015 | Lain et al. |
| 2015/0112230 A1 | 4/2015 | Iglesias |
| 2015/0130830 A1 | 5/2015 | Nagasaki |
| 2015/0141200 A1 * | 5/2015 | Murray ............ A63B 22/0087 482/52 |
| 2015/0149217 A1 | 5/2015 | Kaburagi |
| 2015/0151162 A1 | 6/2015 | Dugan |
| 2015/0158549 A1 | 6/2015 | Gros et al. |
| 2015/0161331 A1 | 6/2015 | Oleynik |
| 2015/0196805 A1 | 7/2015 | Koduri |
| 2015/0257679 A1 | 9/2015 | Ross |
| 2015/0265209 A1 | 9/2015 | Zhang |
| 2015/0290061 A1 | 10/2015 | Stafford et al. |
| 2015/0339442 A1 | 11/2015 | Oleynik |
| 2015/0341812 A1 | 11/2015 | Dion et al. |
| 2015/0351664 A1 | 12/2015 | Ross |
| 2015/0351665 A1 | 12/2015 | Ross |
| 2015/0360069 A1 | 12/2015 | Marti et al. |
| 2015/0379232 A1 | 12/2015 | Mainwaring et al. |
| 2015/0379430 A1 | 12/2015 | Dirac et al. |
| 2016/0007885 A1 | 1/2016 | Basta |
| 2016/0023081 A1 | 1/2016 | Popa-Simil et al. |
| 2016/0045170 A1 | 2/2016 | Migita |
| 2016/0096073 A1 | 4/2016 | Rahman et al. |
| 2016/0117471 A1 | 4/2016 | Belt et al. |
| 2016/0140319 A1 | 5/2016 | Stark |
| 2016/0143593 A1 | 5/2016 | Fu et al. |
| 2016/0151670 A1 | 6/2016 | Dugan |
| 2016/0166833 A1 | 6/2016 | Bum |
| 2016/0166881 A1 | 6/2016 | Ridgel et al. |
| 2016/0193306 A1 | 7/2016 | Rabovsky et al. |
| 2016/0213924 A1 | 7/2016 | Coleman |
| 2016/0275259 A1 | 9/2016 | Nolan et al. |
| 2016/0287166 A1 | 10/2016 | Tran |
| 2016/0302721 A1 | 10/2016 | Wiedenhoefer et al. |
| 2016/0317869 A1 | 11/2016 | Dugan |
| 2016/0322078 A1 | 11/2016 | Bose et al. |
| 2016/0325140 A1 | 11/2016 | Wu |
| 2016/0332028 A1 | 11/2016 | Melnik |
| 2016/0354636 A1 | 12/2016 | Jang |
| 2016/0361597 A1 | 12/2016 | Cole et al. |
| 2016/0373477 A1 | 12/2016 | Moyle |
| 2017/0004260 A1 | 1/2017 | Moturu et al. |
| 2017/0014671 A1 | 1/2017 | Burns, Sr. |
| 2017/0033375 A1 | 2/2017 | Ohmori et al. |
| 2017/0042467 A1 | 2/2017 | Herr et al. |
| 2017/0046488 A1 | 2/2017 | Pereira |
| 2017/0065851 A1 | 3/2017 | Deluca et al. |
| 2017/0080320 A1 | 3/2017 | Smith |
| 2017/0095670 A1 | 4/2017 | Ghaffari et al. |
| 2017/0095692 A1 | 4/2017 | Chang et al. |
| 2017/0095693 A1 | 4/2017 | Chang et al. |
| 2017/0100637 A1 | 4/2017 | Princen et al. |
| 2017/0106242 A1 | 4/2017 | Dugan |
| 2017/0113092 A1 | 4/2017 | Johnson |
| 2017/0128769 A1 | 5/2017 | Long et al. |
| 2017/0132947 A1 | 5/2017 | Maeda et al. |
| 2017/0136296 A1 | 5/2017 | Barrera et al. |
| 2017/0143261 A1 | 5/2017 | Wiedenhoefer et al. |
| 2017/0147752 A1 | 5/2017 | Toru |
| 2017/0147789 A1 | 5/2017 | Wiedenhoefer et al. |
| 2017/0148297 A1 | 5/2017 | Ross |
| 2017/0168555 A1 | 6/2017 | Munoz et al. |
| 2017/0181698 A1 | 6/2017 | Wiedenhoefer et al. |
| 2017/0190052 A1 | 7/2017 | Jaekel et al. |
| 2017/0202724 A1 | 7/2017 | De Rossi |
| 2017/0209766 A1 | 7/2017 | Riley et al. |
| 2017/0220751 A1 | 8/2017 | Davis |
| 2017/0235882 A1 | 8/2017 | Orlov et al. |
| 2017/0235906 A1 | 8/2017 | Dorris et al. |
| 2017/0243028 A1 | 8/2017 | LaFever et al. |
| 2017/0262604 A1 | 9/2017 | Francois |
| 2017/0265800 A1 | 9/2017 | Auchinleck et al. |
| 2017/0266501 A1 | 9/2017 | Sanders et al. |
| 2017/0270260 A1 | 9/2017 | Shetty |
| 2017/0278209 A1 | 9/2017 | Olsen et al. |
| 2017/0282015 A1 | 10/2017 | Wicks et al. |
| 2017/0283508 A1 | 10/2017 | Demopulos et al. |
| 2017/0286621 A1 | 10/2017 | Cox |
| 2017/0300654 A1 | 10/2017 | Stein et al. |
| 2017/0304024 A1 | 10/2017 | Nobrega |
| 2017/0312614 A1 | 11/2017 | Tran et al. |

(56) References Cited

U.S. PATENT DOCUMENTS

| | | |
|---|---|---|
| 2017/0323481 A1 | 11/2017 | Tran et al. |
| 2017/0329917 A1 | 11/2017 | McRaith et al. |
| 2017/0329933 A1 | 11/2017 | Brust |
| 2017/0333755 A1 | 11/2017 | Rider |
| 2017/0337033 A1 | 11/2017 | Duyan et al. |
| 2017/0337334 A1 | 11/2017 | Stanczak |
| 2017/0344726 A1 | 11/2017 | Duffy et al. |
| 2017/0347923 A1 | 12/2017 | Roh |
| 2017/0360586 A1 | 12/2017 | Dempers et al. |
| 2017/0368413 A1 | 12/2017 | Shavit |
| 2018/0017806 A1 | 1/2018 | Wang et al. |
| 2018/0036593 A1 | 2/2018 | Ridgel et al. |
| 2018/0052962 A1 | 2/2018 | Van Der Koijk et al. |
| 2018/0056104 A1 | 3/2018 | Cromie et al. |
| 2018/0060494 A1 | 3/2018 | Dias et al. |
| 2018/0071565 A1 | 3/2018 | Gomberg et al. |
| 2018/0071566 A1 | 3/2018 | Gomberg et al. |
| 2018/0071569 A1 | 3/2018 | Gomberg et al. |
| 2018/0071570 A1 | 3/2018 | Gomberg et al. |
| 2018/0071571 A1 | 3/2018 | Gomberg et al. |
| 2018/0071572 A1 | 3/2018 | Gomberg et al. |
| 2018/0075205 A1 | 3/2018 | Moturu et al. |
| 2018/0078843 A1 | 3/2018 | Tran et al. |
| 2018/0085615 A1 | 3/2018 | Astolfi et al. |
| 2018/0096111 A1 | 4/2018 | Wells et al. |
| 2018/0102190 A1 | 4/2018 | Hogue et al. |
| 2018/0116741 A1 | 5/2018 | Garcia Kilroy et al. |
| 2018/0140927 A1 | 5/2018 | Kito |
| 2018/0146870 A1 | 5/2018 | Shemesh |
| 2018/0177612 A1 | 6/2018 | Trabish et al. |
| 2018/0178061 A1 | 6/2018 | O'larte et al. |
| 2018/0199855 A1 | 7/2018 | Odame et al. |
| 2018/0200577 A1 | 7/2018 | Dugan |
| 2018/0220935 A1 | 8/2018 | Tadano et al. |
| 2018/0228682 A1 | 8/2018 | Bayerlein et al. |
| 2018/0240552 A1 | 8/2018 | Tuyl et al. |
| 2018/0253991 A1 | 9/2018 | Tang et al. |
| 2018/0256079 A1 | 9/2018 | Yang et al. |
| 2018/0263530 A1 | 9/2018 | Jung |
| 2018/0263535 A1 | 9/2018 | Cramer |
| 2018/0263552 A1 | 9/2018 | Graman et al. |
| 2018/0264312 A1 | 9/2018 | Pompile et al. |
| 2018/0271432 A1 | 9/2018 | Auchinleck et al. |
| 2018/0272184 A1 | 9/2018 | Vassilaros et al. |
| 2018/0280784 A1 | 10/2018 | Romeo et al. |
| 2018/0296143 A1 | 10/2018 | Anderson et al. |
| 2018/0296157 A1 | 10/2018 | Bleich et al. |
| 2018/0326243 A1 | 11/2018 | Badi et al. |
| 2018/0330058 A1 | 11/2018 | Bates |
| 2018/0330810 A1 | 11/2018 | Gamarnik |
| 2018/0330824 A1 | 11/2018 | Athey et al. |
| 2018/0290017 A1 | 12/2018 | Fung |
| 2018/0353812 A1 | 12/2018 | Lannon et al. |
| 2018/0360340 A1 | 12/2018 | Rehse et al. |
| 2018/0373844 A1 | 12/2018 | Ferrandez-Escamez et al. |
| 2019/0009135 A1 | 1/2019 | Wu |
| 2019/0019163 A1 | 1/2019 | Batey et al. |
| 2019/0019573 A1 | 1/2019 | Lake et al. |
| 2019/0019578 A1 | 1/2019 | Vaccaro |
| 2019/0030415 A1 | 1/2019 | Volpe, Jr. |
| 2019/0031284 A1 | 1/2019 | Fuchs |
| 2019/0046794 A1 | 2/2019 | Goodall et al. |
| 2019/0060708 A1 | 2/2019 | Fung |
| 2019/0065970 A1 | 2/2019 | Bonutti et al. |
| 2019/0066832 A1 | 2/2019 | Kang et al. |
| 2019/0076701 A1 | 3/2019 | Dugan |
| 2019/0080802 A1 | 3/2019 | Ziobro et al. |
| 2019/0088356 A1 | 3/2019 | Oliver et al. |
| 2019/0090744 A1 | 3/2019 | Mahfouz |
| 2019/0091506 A1 | 3/2019 | Gatelli et al. |
| 2019/0111299 A1 | 4/2019 | Radcliffe et al. |
| 2019/0115097 A1 | 4/2019 | Macoviak et al. |
| 2019/0117128 A1 | 4/2019 | Chen et al. |
| 2019/0118038 A1 | 4/2019 | Tana et al. |
| 2019/0126099 A1 | 5/2019 | Hoang |
| 2019/0132948 A1 | 5/2019 | Longinotti-Buitoni et al. |
| 2019/0134454 A1 | 5/2019 | Mahoney et al. |
| 2019/0137988 A1 | 5/2019 | Cella et al. |
| 2019/0167988 A1 | 6/2019 | Shahriari et al. |
| 2019/0172587 A1 | 6/2019 | Park et al. |
| 2019/0175988 A1 | 6/2019 | Volterrani et al. |
| 2019/0183715 A1 | 6/2019 | Kapure et al. |
| 2019/0200920 A1 | 7/2019 | Tien et al. |
| 2019/0209891 A1 | 7/2019 | Fung |
| 2019/0223797 A1 | 7/2019 | Tran |
| 2019/0228856 A1 | 7/2019 | Leifer |
| 2019/0240103 A1 | 8/2019 | Hepler et al. |
| 2019/0240541 A1 | 8/2019 | Denton et al. |
| 2019/0244540 A1 | 8/2019 | Errante et al. |
| 2019/0251456 A1 | 8/2019 | Constantin |
| 2019/0262084 A1 | 8/2019 | Roh |
| 2019/0269343 A1 | 9/2019 | Ramos Murguialday et al. |
| 2019/0274523 A1 | 9/2019 | Bates et al. |
| 2019/0275368 A1 | 9/2019 | Maroldi |
| 2019/0304584 A1 | 10/2019 | Savolainen |
| 2019/0307983 A1 | 10/2019 | Goldman |
| 2019/0314681 A1 | 10/2019 | Yang |
| 2019/0344123 A1 | 11/2019 | Rubin et al. |
| 2019/0354632 A1 | 11/2019 | Mital et al. |
| 2019/0362242 A1 | 11/2019 | Pillai et al. |
| 2019/0366146 A1 | 12/2019 | Tong et al. |
| 2019/0388728 A1 | 12/2019 | Wang et al. |
| 2020/0005928 A1 | 1/2020 | Daniel |
| 2020/0038703 A1* | 2/2020 | Cleary ................. G06F 3/0346 |
| 2020/0051446 A1 | 2/2020 | Rubinstein et al. |
| 2020/0066390 A1 | 2/2020 | Svendrys et al. |
| 2020/0085300 A1 | 3/2020 | Kwatra et al. |
| 2020/0093418 A1 | 3/2020 | Kluger et al. |
| 2020/0143922 A1 | 5/2020 | Chekroud et al. |
| 2020/0151595 A1 | 5/2020 | Jayalath et al. |
| 2020/0151646 A1 | 5/2020 | De La Fuente Sanchez |
| 2020/0152339 A1 | 5/2020 | Pulitzer et al. |
| 2020/0160198 A1 | 5/2020 | Reeves et al. |
| 2020/0170876 A1 | 6/2020 | Kapure et al. |
| 2020/0176098 A1 | 6/2020 | Lucas et al. |
| 2020/0197744 A1 | 6/2020 | Schweighofer |
| 2020/0221975 A1 | 7/2020 | Basta et al. |
| 2020/0237291 A1 | 7/2020 | Raja |
| 2020/0267487 A1 | 8/2020 | Siva |
| 2020/0275886 A1 | 9/2020 | Mason |
| 2020/0289045 A1 | 9/2020 | Hacking et al. |
| 2020/0289046 A1 | 9/2020 | Hacking et al. |
| 2020/0289878 A1 | 9/2020 | Arn et al. |
| 2020/0289879 A1 | 9/2020 | Hacking et al. |
| 2020/0289880 A1 | 9/2020 | Hacking et al. |
| 2020/0289881 A1 | 9/2020 | Hacking et al. |
| 2020/0289889 A1 | 9/2020 | Hacking et al. |
| 2020/0293712 A1 | 9/2020 | Potts et al. |
| 2020/0303063 A1 | 9/2020 | Sharma et al. |
| 2020/0334972 A1 | 10/2020 | Gopalakrishnan |
| 2020/0357299 A1 | 11/2020 | Patel et al. |
| 2020/0365256 A1 | 11/2020 | Hayashitani et al. |
| 2020/0395112 A1 | 12/2020 | Ronner |
| 2020/0401224 A1 | 12/2020 | Cotton |
| 2020/0410385 A1 | 12/2020 | Otsuki |
| 2020/0411162 A1 | 12/2020 | Lien et al. |
| 2021/0005224 A1 | 1/2021 | Rothschild et al. |
| 2021/0005319 A1 | 1/2021 | Otsuki et al. |
| 2021/0074178 A1 | 3/2021 | Ilan et al. |
| 2021/0076981 A1 | 3/2021 | Hacking et al. |
| 2021/0077860 A1 | 3/2021 | Posnack et al. |
| 2021/0098129 A1 | 4/2021 | Neumann |
| 2021/0101051 A1 | 4/2021 | Posnack et al. |
| 2021/0113890 A1 | 4/2021 | Posnack et al. |
| 2021/0127974 A1 | 5/2021 | Mason et al. |
| 2021/0128080 A1 | 5/2021 | Mason et al. |
| 2021/0128255 A1 | 5/2021 | Mason et al. |
| 2021/0128978 A1 | 5/2021 | Gilstrom et al. |
| 2021/0134412 A1 | 5/2021 | Guaneri et al. |
| 2021/0134425 A1 | 5/2021 | Mason et al. |
| 2021/0134428 A1 | 5/2021 | Mason et al. |
| 2021/0134430 A1 | 5/2021 | Mason et al. |
| 2021/0134432 A1 | 5/2021 | Mason et al. |
| 2021/0134456 A1 | 5/2021 | Posnack et al. |

(56) References Cited

U.S. PATENT DOCUMENTS

| | | |
|---|---|---|
| 2021/0134457 A1 | 5/2021 | Mason et al. |
| 2021/0134458 A1 | 5/2021 | Mason et al. |
| 2021/0134463 A1 | 5/2021 | Mason et al. |
| 2021/0138304 A1 | 5/2021 | Mason et al. |
| 2021/0142875 A1 | 5/2021 | Mason et al. |
| 2021/0142893 A1 | 5/2021 | Guaneri et al. |
| 2021/0142898 A1 | 5/2021 | Mason et al. |
| 2021/0142903 A1 | 5/2021 | Mason et al. |
| 2021/0144074 A1 | 5/2021 | Guaneri et al. |
| 2021/0186419 A1 | 6/2021 | Van Ee et al. |
| 2021/0202090 A1 | 7/2021 | ODonovan et al. |
| 2021/0202103 A1 | 7/2021 | Bostic et al. |
| 2021/0244998 A1 | 8/2021 | Hacking et al. |
| 2021/0245003 A1 | 8/2021 | Turner |
| 2021/0251562 A1 | 8/2021 | Jain |
| 2021/0272677 A1 | 9/2021 | Barbee |
| 2021/0338469 A1 | 11/2021 | Dempers |
| 2021/0343384 A1 | 11/2021 | Purushothaman et al. |
| 2021/0345879 A1 | 11/2021 | Mason et al. |
| 2021/0345975 A1 | 11/2021 | Mason et al. |
| 2021/0350888 A1 | 11/2021 | Guaneri et al. |
| 2021/0350898 A1 | 11/2021 | Mason et al. |
| 2021/0350899 A1 | 11/2021 | Mason et al. |
| 2021/0350901 A1 | 11/2021 | Mason et al. |
| 2021/0350902 A1 | 11/2021 | Mason et al. |
| 2021/0350914 A1 | 11/2021 | Guaneri et al. |
| 2021/0350926 A1 | 11/2021 | Mason et al. |
| 2021/0361514 A1 | 11/2021 | Choi et al. |
| 2021/0366587 A1 | 11/2021 | Mason et al. |
| 2021/0383909 A1 | 12/2021 | Mason et al. |
| 2021/0391091 A1 | 12/2021 | Mason |
| 2021/0398668 A1 | 12/2021 | Chock et al. |
| 2021/0407670 A1 | 12/2021 | Mason et al. |
| 2021/0407681 A1 | 12/2021 | Mason et al. |
| 2022/0000556 A1 | 1/2022 | Casey et al. |
| 2022/0015838 A1 | 1/2022 | Posnack et al. |
| 2022/0016480 A1 | 1/2022 | Bissonnette et al. |
| 2022/0016482 A1 | 1/2022 | Bissonnette |
| 2022/0016485 A1 | 1/2022 | Bissonnette et al. |
| 2022/0016486 A1 | 1/2022 | Bissonnette |
| 2022/0020469 A1 | 1/2022 | Tanner |
| 2022/0044806 A1 | 2/2022 | Sanders et al. |
| 2022/0047921 A1 | 2/2022 | Bissonnette et al. |
| 2022/0079690 A1 | 3/2022 | Mason et al. |
| 2022/0080256 A1 | 3/2022 | Am et al. |
| 2022/0080265 A1 | 3/2022 | Watterson |
| 2022/0105385 A1 | 4/2022 | Hacking et al. |
| 2022/0105390 A1 | 4/2022 | Yuasa |
| 2022/0115133 A1 | 4/2022 | Mason et al. |
| 2022/0118218 A1 | 4/2022 | Bense et al. |
| 2022/0126169 A1 | 4/2022 | Mason |
| 2022/0133576 A1 | 5/2022 | Choi et al. |
| 2022/0148725 A1 | 5/2022 | Mason et al. |
| 2022/0158916 A1 | 5/2022 | Mason et al. |
| 2022/0176039 A1 | 6/2022 | Lintereur et al. |
| 2022/0181004 A1 | 6/2022 | Zilca et al. |
| 2022/0193491 A1 | 6/2022 | Mason et al. |
| 2022/0230729 A1 | 7/2022 | Mason et al. |
| 2022/0238223 A1 | 7/2022 | Mason et al. |
| 2022/0262483 A1 | 8/2022 | Rosenberg et al. |
| 2022/0262504 A1 | 8/2022 | Bratty et al. |
| 2022/0266094 A1 | 8/2022 | Mason et al. |
| 2022/0270738 A1 | 8/2022 | Mason et al. |
| 2022/0273985 A1 | 9/2022 | Jeong et al. |
| 2022/0273986 A1 | 9/2022 | Mason |
| 2022/0288460 A1 | 9/2022 | Mason |
| 2022/0288461 A1 | 9/2022 | Ashley et al. |
| 2022/0288462 A1 | 9/2022 | Ashley et al. |
| 2022/0293257 A1 | 9/2022 | Guaneri et al. |
| 2022/0300787 A1 | 9/2022 | Wall et al. |
| 2022/0304881 A1 | 9/2022 | Choi et al. |
| 2022/0304882 A1 | 9/2022 | Choi |
| 2022/0305328 A1 | 9/2022 | Choi et al. |
| 2022/0314075 A1 | 10/2022 | Mason et al. |
| 2022/0323826 A1 | 10/2022 | Khurana |
| 2022/0327714 A1 | 10/2022 | Cook et al. |
| 2022/0327807 A1 | 10/2022 | Cook et al. |
| 2022/0328181 A1 | 10/2022 | Mason et al. |
| 2022/0330823 A1 | 10/2022 | Janssen |
| 2022/0331663 A1 | 10/2022 | Mason |
| 2022/0338761 A1 | 10/2022 | Maddahi et al. |
| 2022/0339052 A1 | 10/2022 | Kim |
| 2022/0339501 A1 | 10/2022 | Mason et al. |
| 2022/0384012 A1 | 12/2022 | Mason |
| 2022/0392591 A1 | 12/2022 | Guaneri et al. |
| 2022/0395232 A1 | 12/2022 | Locke |
| 2022/0401783 A1 | 12/2022 | Choi |
| 2022/0415469 A1 | 12/2022 | Mason |
| 2022/0415471 A1 | 12/2022 | Mason |
| 2023/0001268 A1 | 1/2023 | Bissonnette et al. |
| 2023/0013530 A1 | 1/2023 | Mason |
| 2023/0014598 A1 | 1/2023 | Mason et al. |
| 2023/0029639 A1 | 2/2023 | Roy |
| 2023/0048040 A1 | 2/2023 | Hacking et al. |
| 2023/0051751 A1 | 2/2023 | Hacking et al. |
| 2023/0058605 A1 | 2/2023 | Mason |
| 2023/0060039 A1 | 2/2023 | Mason |
| 2023/0072368 A1 | 3/2023 | Mason |
| 2023/0078793 A1 | 3/2023 | Mason |
| 2023/0119461 A1 | 4/2023 | Mason |
| 2023/0190100 A1 | 6/2023 | Stump |
| 2023/0201656 A1 | 6/2023 | Hacking et al. |
| 2023/0207097 A1 | 6/2023 | Mason |
| 2023/0207124 A1 | 6/2023 | Walsh et al. |
| 2023/0215539 A1 | 7/2023 | Rosenberg et al. |
| 2023/0215552 A1 | 7/2023 | Khotilovich et al. |
| 2023/0245747 A1 | 8/2023 | Rosenberg et al. |
| 2023/0245748 A1 | 8/2023 | Rosenberg et al. |
| 2023/0245750 A1 | 8/2023 | Rosenberg et al. |
| 2023/0245751 A1 | 8/2023 | Rosenberg et al. |
| 2023/0253089 A1 | 8/2023 | Rosenberg et al. |
| 2023/0255555 A1 | 8/2023 | Sundaram et al. |
| 2023/0263428 A1 | 8/2023 | Hull et al. |
| 2023/0274813 A1 | 8/2023 | Rosenberg et al. |
| 2023/0282329 A1 | 9/2023 | Mason et al. |
| 2023/0364472 A1 | 11/2023 | Posnack |
| 2023/0368886 A1 | 11/2023 | Rosenberg |
| 2023/0377711 A1 | 11/2023 | Rosenberg |
| 2023/0377712 A1 | 11/2023 | Rosenberg |
| 2023/0386639 A1 | 11/2023 | Rosenberg |
| 2023/0395231 A1 | 12/2023 | Rosenberg |
| 2023/0395232 A1 | 12/2023 | Rosenberg |
| 2024/0029856 A1 | 1/2024 | Rosenberg |

FOREIGN PATENT DOCUMENTS

| | | |
|---|---|---|
| CN | 101964151 A | 2/2011 |
| CN | 201889024 U | 7/2011 |
| CN | 202220794 U | 5/2012 |
| CN | 102670381 A | 9/2012 |
| CN | 103263336 A | 8/2013 |
| CN | 103390357 A | 11/2013 |
| CN | 103473631 A | 12/2013 |
| CN | 103488880 A | 1/2014 |
| CN | 103501328 A | 1/2014 |
| CN | 103721343 A | 4/2014 |
| CN | 203677851 U | 7/2014 |
| CN | 104335211 | 2/2015 |
| CN | 105620643 A | 6/2016 |
| CN | 105683977 A | 6/2016 |
| CN | 103136447 B | 8/2016 |
| CN | 105894088 A | 8/2016 |
| CN | 105930668 A | 9/2016 |
| CN | 205626871 U | 10/2016 |
| CN | 106127646 A | 11/2016 |
| CN | 106236502 A | 12/2016 |
| CN | 106510985 A | 3/2017 |
| CN | 106621195 A | 5/2017 |
| CN | 107066819 A | 8/2017 |
| CN | 107430641 A | 12/2017 |
| CN | 107551475 A | 1/2018 |
| CN | 107736982 A | 2/2018 |
| CN | 107930021 A | 4/2018 |
| CN | 207220817 U | 4/2018 |

(56) References Cited

FOREIGN PATENT DOCUMENTS

| | | | |
|---|---|---|---|
| CN | 108078737 | A | 5/2018 |
| CN | 208224811 | A | 12/2018 |
| CN | 109191954 | A | 1/2019 |
| CN | 109363887 | A | 2/2019 |
| CN | 208573971 | U | 3/2019 |
| CN | 110148472 | A | 8/2019 |
| CN | 110201358 | A | 9/2019 |
| CN | 110215188 | A | 9/2019 |
| CN | 110322957 | A | 10/2019 |
| CN | 110808092 | A | 2/2020 |
| CN | 110931103 | A | 3/2020 |
| CN | 110993057 | A | 4/2020 |
| CN | 111084618 | A | 5/2020 |
| CN | 111105859 | A | 5/2020 |
| CN | 111111110 | A | 5/2020 |
| CN | 111370088 | A | 7/2020 |
| CN | 111460305 | A | 7/2020 |
| CN | 112071393 | A | 12/2020 |
| CN | 212141371 | U | 12/2020 |
| CN | 112289425 | A | 1/2021 |
| CN | 212624809 | U | 2/2021 |
| CN | 112603295 | A | 4/2021 |
| CN | 213190965 | U | 5/2021 |
| CN | 113384850 | A | 9/2021 |
| CN | 113499572 | A | 10/2021 |
| CN | 214388673 | U | 10/2021 |
| CN | 215136488 | U | 12/2021 |
| CN | 113885361 | A | 1/2022 |
| CN | 114049961 | A | 2/2022 |
| CN | 114203274 | A | 3/2022 |
| CN | 216258145 | U | 4/2022 |
| CN | 114694824 | A | 7/2022 |
| CN | 114898832 | A | 8/2022 |
| CN | 114983760 | A | 9/2022 |
| CN | 217472652 | U | 9/2022 |
| CN | 110270062 | B | 10/2022 |
| CN | 218420859 | U | 2/2023 |
| CN | 115954081 | A | 4/2023 |
| DE | 95019 | C | 1/1897 |
| DE | 7628633 | U1 | 12/1977 |
| DE | 8519150 | U1 | 10/1985 |
| DE | 3732905 | A1 | 7/1988 |
| DE | 19619820 | A1 | 12/1996 |
| DE | 29620008 | U1 | 2/1997 |
| DE | 19947926 | A1 | 4/2001 |
| DE | 102018202497 | A1 | 8/2018 |
| DE | 102018211212 | A1 | 1/2019 |
| DE | 102019108425 | B3 | 8/2020 |
| EP | 199600 | A2 | 10/1986 |
| EP | 0383137 | A2 | 8/1990 |
| EP | 634319 | A2 | 1/1995 |
| EP | 1034817 | A1 | 9/2000 |
| EP | 1159989 | A1 | 12/2001 |
| EP | 1968028 | | 9/2008 |
| EP | 2564904 | A1 | 3/2013 |
| EP | 1909730 | B1 | 4/2014 |
| EP | 2815242 | A4 | 12/2014 |
| EP | 2869805 | A | 5/2015 |
| EP | 2997951 | A1 | 3/2016 |
| EP | 2688472 | B1 | 4/2016 |
| EP | 3264303 | A1 | 1/2018 |
| EP | 3323473 | A1 | 5/2018 |
| EP | 3627514 | A1 | 3/2020 |
| EP | 3671700 | A1 | 6/2020 |
| EP | 3688537 | A1 | 8/2020 |
| EP | 3731733 | A1 | 11/2020 |
| EP | 3984508 | A1 | 4/2022 |
| EP | 3984509 | A1 | 4/2022 |
| EP | 3984510 | A1 | 4/2022 |
| EP | 3984511 | A1 | 4/2022 |
| EP | 3984512 | A1 | 4/2022 |
| EP | 3984513 | A1 | 4/2022 |
| EP | 4054699 | A1 | 9/2022 |
| EP | 4112033 | A1 | 1/2023 |
| FR | 2527541 | A2 | 12/1983 |
| FR | 3127393 | A1 | 3/2023 |
| GB | 141664 | A | 11/1920 |
| GB | 2336140 | A | 10/1999 |
| GB | 2372459 | A | 8/2002 |
| GB | 2512431 | A | 10/2014 |
| GB | 2591542 | B | 3/2022 |
| IN | 201811043670 | A | 7/2018 |
| JP | 2000005339 | A | 1/2000 |
| JP | 2003225875 | A | 8/2003 |
| JP | 2005227928 | A | 8/2005 |
| JP | 2005227928 | A1 | 8/2005 |
| JP | 2009112336 | A | 5/2009 |
| JP | 2013515995 | A | 5/2013 |
| JP | 3193662 | U | 10/2014 |
| JP | 3198173 | U | 6/2015 |
| JP | 5804063 | B2 | 11/2015 |
| JP | 2018102842 | A | 7/2018 |
| JP | 2019028647 | A | 2/2019 |
| JP | 2019134909 | A | 8/2019 |
| JP | 6573739 | B1 | 9/2019 |
| JP | 6659831 | B2 | 3/2020 |
| JP | 6710357 | B1 | 6/2020 |
| JP | 6775757 | B1 | 10/2020 |
| JP | 2021027917 | A | 2/2021 |
| JP | 6871379 | B2 | 5/2021 |
| JP | 2022521378 | A | 4/2022 |
| JP | 3238491 | U | 7/2022 |
| JP | 7198364 | B2 | 12/2022 |
| JP | 7202474 | B2 | 1/2023 |
| JP | 7231750 | B2 | 3/2023 |
| JP | 7231751 | B2 | 3/2023 |
| JP | 7231752 | B2 | 3/2023 |
| KR | 20020009724 | A | 2/2002 |
| KR | 200276919 | Y1 | 5/2002 |
| KR | 20020065253 | A | 8/2002 |
| KR | 100582596 | B1 | 5/2006 |
| KR | 101042258 | B1 | 6/2011 |
| KR | 20110099953 | A | 9/2011 |
| KR | 101258250 | B1 | 4/2013 |
| KR | 101325581 | B1 | 11/2013 |
| KR | 20140128630 | A | 11/2014 |
| KR | 20150017693 | A | 2/2015 |
| KR | 20150078191 | A | 7/2015 |
| KR | 101580071 | B1 | 12/2015 |
| KR | 101647620 | B1 | 8/2016 |
| KR | 20160093990 | A | 8/2016 |
| KR | 20170038837 | A | 4/2017 |
| KR | 20180004928 | A | 1/2018 |
| KR | 20190029175 | A | 3/2019 |
| KR | 20190056116 | A | 5/2019 |
| KR | 101988167 | B1 | 6/2019 |
| KR | 101969392 | B1 | 8/2019 |
| KR | 102055279 | B1 | 12/2019 |
| KR | 102088333 | B1 | 3/2020 |
| KR | 20200025290 | A | 3/2020 |
| KR | 20200029180 | A | 3/2020 |
| KR | 102116664 | B1 | 5/2020 |
| KR | 102116968 | B1 | 5/2020 |
| KR | 20200056233 | A | 5/2020 |
| KR | 102120828 | B1 | 6/2020 |
| KR | 102121586 | B1 | 6/2020 |
| KR | 102142713 | B1 | 8/2020 |
| KR | 102162522 | B1 | 10/2020 |
| KR | 20200119665 | A | 10/2020 |
| KR | 102173553 | B1 | 11/2020 |
| KR | 102180079 | B1 | 11/2020 |
| KR | 102188766 | B1 | 12/2020 |
| KR | 102196793 | B1 | 12/2020 |
| KR | 20210006212 | A | 1/2021 |
| KR | 102224188 | B1 | 3/2021 |
| KR | 102224618 | B1 | 3/2021 |
| KR | 102246049 | B1 | 4/2021 |
| KR | 102246050 | B1 | 4/2021 |
| KR | 102246051 | B1 | 4/2021 |
| KR | 102246052 | B1 | 4/2021 |
| KR | 102264498 | B1 | 6/2021 |
| KR | 102352602 | B1 | 1/2022 |
| KR | 102352603 | B1 | 1/2022 |
| KR | 102352604 | B1 | 1/2022 |

(56) References Cited

FOREIGN PATENT DOCUMENTS

| | | |
|---|---|---|
| KR | 20220004639 A | 1/2022 |
| KR | 102387577 B1 | 4/2022 |
| KR | 102421437 B1 | 7/2022 |
| KR | 20220102207 A | 7/2022 |
| KR | 102427545 B1 | 8/2022 |
| KR | 102467495 B1 | 11/2022 |
| KR | 102467496 B1 | 11/2022 |
| KR | 102469723 B1 | 11/2022 |
| KR | 102471990 B1 | 11/2022 |
| KR | 20220145989 A | 11/2022 |
| KR | 20220156134 A | 11/2022 |
| KR | 102502744 B1 | 2/2023 |
| KR | 20230019349 A | 2/2023 |
| KR | 20230019350 A | 2/2023 |
| KR | 20230026556 A | 2/2023 |
| KR | 20230026668 A | 2/2023 |
| KR | 20230040526 | 3/2023 |
| KR | 20230050506 A | 4/2023 |
| KR | 20230056118 A | 4/2023 |
| KR | 102528503 B1 | 5/2023 |
| KR | 102531930 B1 | 5/2023 |
| KR | 102532766 B1 | 5/2023 |
| KR | 102539190 B1 | 6/2023 |
| RU | 2014131288 A | 2/2016 |
| RU | 2607953 C2 | 1/2017 |
| TW | M474545 U | 3/2014 |
| TW | I442956 B | 7/2014 |
| TW | M638437 U | 3/2023 |
| WO | 1998009687 | 3/1998 |
| WO | 0149235 A2 | 7/2001 |
| WO | 0151083 A2 | 7/2001 |
| WO | 2001050387 A1 | 7/2001 |
| WO | 2001056465 A1 | 8/2001 |
| WO | 02093312 A2 | 11/2002 |
| WO | 2003043494 A1 | 5/2003 |
| WO | 2005018453 A1 | 3/2005 |
| WO | 2006004430 A2 | 1/2006 |
| WO | 2006012694 A1 | 2/2006 |
| WO | 2007102709 A1 | 9/2007 |
| WO | 2008114291 A1 | 9/2008 |
| WO | 2011025322 A2 | 3/2011 |
| WO | 2012128801 A1 | 9/2012 |
| WO | 2013002568 A2 | 1/2013 |
| WO | 2023164292 A1 | 3/2013 |
| WO | 2013122839 A1 | 8/2013 |
| WO | 2014011447 A1 | 1/2014 |
| WO | 2014039567 A1 | 3/2014 |
| WO | 2014163976 A1 | 10/2014 |
| WO | 2015026744 A1 | 2/2015 |
| WO | 2015065298 A1 | 5/2015 |
| WO | 2015082555 A1 | 6/2015 |
| WO | 2016154318 A1 | 9/2016 |
| WO | 2017030781 A1 | 2/2017 |
| WO | 2017091691 A1 | 6/2017 |
| WO | 2017165238 A1 | 9/2017 |
| WO | 2018081795 A1 | 5/2018 |
| WO | 2018171853 A1 | 9/2018 |
| WO | 2019022706 A1 | 1/2019 |
| WO | 2019143940 A1 | 7/2019 |
| WO | 2020185769 A1 | 3/2020 |
| WO | 2020075190 A1 | 4/2020 |
| WO | 2020130979 A1 | 6/2020 |
| WO | 2020149815 A2 | 7/2020 |
| WO | 2020245727 A1 | 12/2020 |
| WO | 2020249855 A1 | 12/2020 |
| WO | 2020252599 A1 | 12/2020 |
| WO | 2020256577 A1 | 12/2020 |
| WO | 2021021447 A1 | 2/2021 |
| WO | 2021038980 A1 | 3/2021 |
| WO | 2021055427 A1 | 3/2021 |
| WO | 2021055491 A1 | 3/2021 |
| WO | 2021061061 A1 | 4/2021 |
| WO | 2021081094 A1 | 4/2021 |
| WO | 2021090267 A1 | 5/2021 |
| WO | 2021138620 A1 | 7/2021 |
| WO | 2021216881 A1 | 10/2021 |
| WO | 2021236542 A1 | 11/2021 |
| WO | 2021236961 A1 | 11/2021 |
| WO | 2021262809 A1 | 12/2021 |
| WO | 2022047006 A1 | 3/2022 |
| WO | 2022092493 A1 | 5/2022 |
| WO | 2022092494 A1 | 5/2022 |
| WO | 2022212883 A1 | 10/2022 |
| WO | 2022212921 A1 | 10/2022 |
| WO | 2022216498 A1 | 10/2022 |
| WO | 2022251420 A1 | 12/2022 |
| WO | 2023008680 A1 | 2/2023 |
| WO | 2023008681 A1 | 2/2023 |
| WO | 2023022319 A1 | 2/2023 |
| WO | 2023022320 A1 | 2/2023 |
| WO | 2023052695 A1 | 4/2023 |
| WO | 2023091496 A1 | 5/2023 |
| WO | 2023215155 A1 | 11/2023 |
| WO | 2023230075 A1 | 11/2023 |

OTHER PUBLICATIONS

Jennifer Bresnick, "What is the Role of Natural Language Processing in Healthcare?", pp. 1-7, published Aug. 18, 2016, retrieved on Feb. 1, 2022 from https://healthitanalytics.com/ featu res/what-is-the-role-of-natural-language-processing-in-healthcare.

Alex Bellec, "Part-of-Speech tagging tutorial with the Keras Deep Learning library," pp. 1-16, published Mar. 27, 2018, retrieved on Feb. 1, 2022 from https://becominghuman.ai/part-of-speech-tagging-tutorial-with-the-keras-deep-learning-library-d7f93fa05537.

Kavita Ganesan, All you need to know about text preprocessing for NLP and Machine Learning, pp. 1-14, published Feb. 23, 2019, retrieved on Feb. 1, 2022 from https:// towardsdatascience.com/all-you-need-to-know-about-text-preprocessing-for-nlp-and-machine-learning-bcl c5765ff67.

Badreesh Shetty, "Natural Language Processing (NPL) for Machine Learning," pp. 1-13, published Nov. 24, 2018, retrieved on Feb. 1, 2022 from https://towardsdatascience. com/natural-language-processing-nlp-for-machine-learning-d44498845d5b.

Claris Healthcare Inc., Claris Reflex Patient Rehabilitation System Brochure, retrieved on Oct. 2, 2019, 5 pages, https://clarisreflex.com/.

Fysiomed, 16983—Vario adjustable pedal arms, retrieved from timestamp of Jun. 7, 2017 from https://web.archive.org/web/20160607052632/https://www.fysiomed.com/en/products/16983-vario-adjustable-pedal-arms on Dec. 15, 2021, 4 pages.

HCL Fitness, HCI Fitness PhysioTrainer Pro, 2017, retrieved on Aug. 19, 2021, 7 pages, https://www.amazon.com/HCI-Fitness-Physio Trainer-Electronically-Controlled/dp/B0759YMW78/.

HCL Fitness, HCI Fitness PhysioTrainer Upper Body Ergonometer, announced 2009 [online], retrieved on Aug. 19, 2021, 8 pages, www.amazon.com/HCI-Fitness-PhysioTrainer-Upper-Ergonometer/dp/B001 P5GUGM.

International Preliminary Report on Patentability of International Application No. PCT/US2017/50895, Date of Mailing Dec. 11, 2018, 52 pages.

International Searching Authority, Search Report and Written Opinion for International Application No. PCT/US2017/50895, Date of Mailing Jan. 12, 2018, 6 pages.

International Searching Authority, Search Report and Written Opinion for International Application No. PCT/US2020/021876, Date of Mailing May 28, 2020, 8 pages.

International Searching Authority, Search Report and Written Opinion for International Application No. PCT/US2020/051008, Date of Mailing Dec. 10, 2020, 9 pages.

International Searching Authority, Search Report and Written Opinion for International Application No. PCT/US2020/056661, Date of Mailing Feb. 12, 2021, 12 pages.

International Search Report and Written Opinion for PCT/US2023/014137, dated Jun. 9, 2023, 13 pages.

Website for "Esino 2022 Physical Therapy Equipments Arm Fitness Indoor Trainer Leg Spin Cycle Machine Exercise Bike for Elderly," https://www.made-in-china.com/showroom/esinogroup/product-

(56) References Cited

OTHER PUBLICATIONS detailYdZtwGhCMKVR/China-Esino-2022-Physical-Therapy-Equipments-Arm-Fitness-Indoor-Trainer-Leg-Spin-Cycle-Machine-Exercise-Bike-for-Elderly.html, retrieved on Aug. 29, 2023, 5 pages.
Abedtash, "An Interoperable Electronic Medical Record-Based Platform For Personalized Predictive Analytics", ProQuest LLC, Jul. 2017, 185 pages.
Website for "Pedal Exerciser", p. 1, retrieved on Sep. 9, 2022 from https://www.vivehealth.com/collections/physical-therapy-equipment/products/pedalexerciser.
Website for "Functional Knee Brace with ROM", p. 1, retrieved on Sep. 9, 2022 from http://medicalbrace.gr/en/product/functional-knee-brace-with-goniometer-mbtelescopicknee/.
Website for "ComfySplints Goniometer Knee", pp. 1-5, retrieved on Sep. 9, 2022 from https://www.comfysplints.com/product/knee-splints/.
Website for "BMI FlexEze Knee Corrective Orthosis (KCO)", pp. 1-4, retrieved on Sep. 9, 2022 from https://orthobmi.com/products/bmi-flexeze%C2%AE-knee-corrective-orthosis-kco.
Website for "Neoprene Knee Brace with goniometer—Patella ROM MB.4070", pp. 1-4, retrieved on Sep. 9, 2022 from https://www.fortuna.com.gr/en/product/neoprene-knee-brace-with-goniometer-patella-rom-mb-4070/.
Kuiken et al., "Computerized Biofeedback Knee Goniometer: Acceptance and Effect on Exercise Behavior in Post-total Knee Arthroplasty Rehabilitation," Biomedical Engineering Faculty Research and Publications, 2004, pp. 1-10.
Ahmed et al., "Artificial intelligence with multi-functional machine learning platform development for better healthcare and precision medicine," Database, 2020, pp. 1-35.
Davenport et al., "The potential for artificial intelligence in healthcare," Digital Technology, Future Healthcare Journal, 2019, pp. 1-5, vol. 6, No. 2.
Website for "OxeFit XS1", pp. 1-3, retrieved on Sep. 9, 2022 from https://www.oxefit.com/xs1.
Website for "Preva Mobile", pp. 1-6, retrieved on Sep. 9, 2022 from https://www.precor.com/en-us/resources/introducing-preva-mobile.
Website for "J-Bike", pp. 1-3, retrieved on Sep. 9, 2022 from https://www.magneticdays.com/en/cycling-for-physical-rehabilitation.
Website for "Excy", pp. 1-12, retrieved on Sep. 9, 2022 from https://excy.com/portable-exercise-rehabilitation-excy-xcs-pro/.
Website for "OxeFit XP1", p. 1, retrieved on Sep. 9, 2022 from https://www.oxefit.com/xp1.
Jeong et al., "Computer-assisted upper extremity training using interactive biking exercise (iBikE) platform," Sep. 2012, pp. 1-5, 34th Annual International Conference of the IEEE EMBS.
ROM3 Rehab, ROM3 Rehab System, Apr. 20, 2015, retrieved on Aug. 31, 2018, 12 pages, https://vimeo.com/125438463.
Matrix, R3xm Recumbent Cycle, retrieved on Aug. 4, 2020, 7 pages, https://www.matrixfitness.com/en/cardio/cycles/r3xm-recumbent.
International Searching Authority, Search Report and Written Opinion for International Application No. PCT/US2021/038617, Date of Mailing Oct. 15, 2021; 12 pages.
International Searching Authority, Search Report and Written Opinion for International Application No. PCT/US2021/032807, Date of Mailing Sep. 6, 2021, 11 pages.
Davenport et al., "The Potential For Artificial Intelligence In Healthcare", 2019, Future Healthcare Journal 2019, vol. 6, No. 2: Year: 2019, pp. 1-5.
Ahmed et al., "Artificial Intelligence With Multi-Functional Machine Learning Platform Development For Better Healthcare And Precision Medicine", 2020, Database (Oxford), 2020:baaa010. doi: 10.1093/database/baaa010 (Year: 2020), pp. 1-35.
Ruiz Ivan et al., "Towards a physical rehabilitation system using a telemedicine approach", Computer Methods in Biomechanics and Biomedical Engineering: Imaging & Visualization, vol. 8, No. 6, Jul. 28, 2020, pp. 671-680, XP055914810.
De Canniere Helene et al., "Wearable Monitoring and Interpretable Machine Learning Can Objectively Track Progression in Patients during Cardiac Rehabilitation", Sensors, vol. 20, No. 12, Jun. 26, 2020, XP055914617, pp. 1-15.
Boulanger Pierre et al., "A Low-cost Virtual Reality Bike for Remote Cardiac Rehabilitation", Dec. 7, 2017, Advances in Biometrics: International Conference, ICB 2007, Seoul, Korea, pp. 155-166.
Yin Chieh et al., "A Virtual Reality-Cycling Training System for Lower Limb Balance Improvement", BioMed Research International, vol. 2016, pp. 1-10.
Barrett et al., "Artificial intelligence supported patient self-care in chronic heart failure: a paradigm shift from reactive to predictive, preventive and personalised care," EPMA Journal (2019), pp. 445-464.
Oerkild et al., "Home-based cardiac rehabilitation is an attractive alternative to no cardiac rehabilitation for elderly patients with coronary heart disease: results from a randomised clinical trial," BMJ Open Accessible Medical Research, Nov. 22, 2012, pp. 1-9.
Bravo-Escobar et al., "Effectiveness and safety of a home-based cardiac rehabilitation programme of mixed surveillance in patients with ischemic heart disease at moderate cardiovascular risk: A randomised, controlled clinical trial," BMC Cardiovascular Disorders, 2017, pp. 1-11, vol. 17:66.
Thomas et al., "Home-Based Cardiac Rehabilitation," Circulation, 2019, pp. e69-e89, vol. 140.
Thomas et al., "Home-Based Cardiac Rehabilitation," Journal of the American College of Cardiology, Nov. 1, 2019, pp. 133-153, vol. 74.
Thomas et al., "Home-Based Cardiac Rehabilitation," HHS Public Access, Oct. 2, 2020, pp. 1-39.
Dittus et al., "Exercise-Based Oncology Rehabilitation: Leveraging the Cardiac Rehabilitation Model," Journal of Cardiopulmonary Rehabilitation and Prevention, 2015, pp. 130-139, vol. 35.
Chen et al., "Home-based cardiac rehabilitation improves quality of life, aerobic capacity, and readmission rates in patients with chronic heart failure," Medicine, 2018, pp. 1-5 vol. 97:4.
Lima de Melo Ghisi et al., "A systematic review of patient education in cardiac patients: Do they increase knowledge and promote health behavior change?," Patient Education and Counseling, 2014, pp. 1-15.
Fang et al., "Use of Outpatient Cardiac Rehabilitation Among Heart Attack Survivors—20 States and the District of Columbia, 2013 and Four States, 2015," Morbidity and Mortality Weekly Report, vol. 66, No. 33, Aug. 25, 2017, pp. 869-873.
Beene et al., "AI and Care Delivery: Emerging Opportunities For Artificial Intelligence To Transform How Care Is Delivered," Nov. 2019, American Hospital Association, pp. 1-12.
Alcaraz et al., "Machine Learning as Digital Therapy Assessment for Mobile Gait Rehabilitation," 2018 IEEE 28th International Workshop on Machine Learning for Signal Processing (MLSP), Aalborg, Denmark, 2018, 6 pages.
Androutsou et al., "A Smartphone Application Designed to Engage the Elderly in Home-Based Rehabilitation," Frontiers in Digital Health, Sep. 2020, vol. 2, Article 15, 13 pages.
Silva et al., "SapoFitness: A mobile health application for dietary evaluation," 2011 IEEE 13th International Conference on U e-Health Networking, Applications and Services, Columbia, MO, USA, 2011, 6 pages.
Wang et al., "Interactive wearable systems for upper body rehabilitation: a systematic review," Journal of NeuroEngineering and Rehabilitation, 2017, 21 pages.
Marzolini et al., "Eligibility, Enrollment, and Completion of Exercise-Based Cardiac Rehabilitation Following Stroke Rehabilitation: What Are the Barriers?," Physical Therapy, vol. 100, No. 1, 2019, 13 pages.
Nijjar et al., "Randomized Trial of Mindfulness-Based Stress Reduction in Cardiac Patients Eligible for Cardiac Rehabilitation," Scientific Reports, 2019, 12 pages.
Lara et al., "Human-Robot Sensor Interface for Cardiac Rehabilitation," IEEE International Conference on Rehabilitation Robotics, Jul. 2017, 8 pages.

(56) References Cited

OTHER PUBLICATIONS

Ishraque et al., "Artificial Intelligence-Based Rehabilitation Therapy Exercise Recommendation System," 2018 IEEE MIT Undergraduate Research Technology Conference (URTC), Cambridge, MA, USA, 2018, 5 pages.

Zakari et al., "Are There Limitations to Exercise Benefits in Peripheral Arterial Disease?," Frontiers in Cardiovascular Medicine, Nov. 2018, vol. 5, Article 173, 12 pages.

You et al., "Including Blood Vasculature into a Game-Theoretic Model of Cancer Dynamics," Games 2019, 10, 13, 22 pages.

Jeong et al., "Computer-assisted upper extremity training using interactive biking exercise (iBikE) platform," Sep. 2012, 34th Annual International Conference of the IEEE EMBS, 5 pages.

Chrif et al., "Control design for a lower-limb paediatric therapy device using linear motor technology," Article, 2017, pp. 119-127, Science Direct, Switzerland.

Robben et al., "Delta Features From Ambient Sensor Data are Good Predictors of Change in Functional Health," Article, 2016, pp. 2168-2194, vol. 21, No. 4, IEEE Journal of Biomedical and Health Informatics.

Kantoch et al., "Recognition of Sedentary Behavior by Machine Learning Analysis of Wearable Sensors during Activities of Daily Living for Telemedical Assessment of Cardiovascular Risk," Article, 2018, 17 pages, Sensors, Poland.

Warburton et al., "International Launch of the Par-•Q+ and ePARmed-•X+ Validation of the PAR-•Q+ and ePARmed••X+," Health & Fitness Journal of Canada, 2011, 9 pages, vol. 4, No. 2.

Gerbild et al., "Physical Activity to Improve Erectile Dysfunction: A Systematic Review of Intervention Studies," Sexual Medicine, 2018, 15 pages.

\* cited by examiner

502 — Receive a set of angles from one or more goniometers, wherein the set of angles include at least one of angles of extension of a lower leg of a user extended away from an upper leg at a knee or angles of bend of the lower leg retracting closer toward the upper leg

504 — Transmit, via one or more network interface cards, the set of angles to a computing device controlling the electromechanical device

FIG. 5

BENDABLE SENSOR DEVICE FOR MONITORING JOINT EXTENSION AND FLEXION

CROSS-REFERENCE TO RELATED APPLICATION(S)

This application is a divisional of U.S. patent application Ser. No. 16/675,753, filed Nov. 6, 2019, which claims priority to and the benefit of U.S. Provisional Application Patent Ser. No. 62/816,503, filed Mar. 11, 2019, the entire disclosure of which is hereby incorporated by reference.

TECHNICAL FIELD

This disclosure relates generally to electromechanical devices. More specifically, this disclosure relates to a control system for an electromechanical device for rehabilitation or exercise.

BACKGROUND

Various devices may be used by people for exercising and/or rehabilitating parts of their bodies. For example, as part of workout regimens to maintain a desired level of fitness, users may operate devices for a period of time or distance. In another example, a person may undergo knee surgery and a physician may provide a treatment plan for rehabilitation to strengthen and/or improve flexibility of the knee that includes periodically operating a rehabilitation device for a period of time and/or distance. The exercise and/or rehabilitation devices may include pedals on opposite sides. The devices may be operated by users engaging the pedals with their feet or their hands and rotating the pedals.

SUMMARY

In general, the present disclosure provides a control system for a rehabilitation or exercise device and associated components of the device.

In one aspect, a system for rehabilitation includes one or more electronic devices comprising one or more memory devices storing instructions, one or more network interface cards, and one or more sensors, wherein the one or more electronic devices are coupled to a user. The system for rehabilitation further includes one or more processing devices operatively coupled to the one or more memory devices, the one or more network interface cards, and the one or more sensors. The one or more processing devices are configured to execute the instructions to receive information from the one or more sensors. The one or more processing devices are further configured to execute the instructions to transmit the information to a computing device controlling an electromechanical device, via the one or more network interface cards.

In another aspect, a system for rehabilitation includes one or more electronic devices comprising one or more memory devices storing instructions, one or more network interface cards, and one or more sensors, wherein the one or more electronic devices are coupled to a user. The system for rehabilitation further includes an electromechanical device comprising an electric motor and one or more pedals. The system for rehabilitation further includes one or more processing devices operatively coupled to the one or more memory devices, the one or more network interface cards, and the one or more sensors. The one or more processing devices are configured to execute the instructions to (i) receive configuration information for a pedaling session; (ii) based on the configuration information for the pedaling session, set a resistance parameter and a maximum pedal force parameter; (iii) measure force applied to the one or more pedals of the electromechanical device as a user pedals the electromechanical device, wherein, based on the resistance parameter, the electric motor provides resistance during the pedaling session; (iv) determine whether the measured force exceeds a value of the maximum pedal force parameter; and (v) responsive to determining that the measured force exceeds the value of the maximum pedal force parameter, reduce the resistance parameter so the electric motor applies less resistance during the pedaling session to maintain a revolutions per time period threshold.

In yet another aspect, a system for rehabilitation further includes one or more electronic devices comprising one or more memory devices storing instructions, one or more network interface cards, and one or more sensors, wherein the one or more electronic devices are flexible and worn by a user. The system for rehabilitation further includes one or more processing devices operatively coupled to the one or more memory devices, the one or more network interface cards, and the one or more sensors. The one or more processing devices are further configured to execute the instructions to (i) receive, from the one or more electronic devices, a plurality of angles of extension between an upper leg and a lower leg at a knee of the user, wherein the plurality of angles is measured as the user extends the lower leg away from the upper leg via the knee; (ii) present, on a user interface, a graphical animation of the upper leg, the lower leg, and the knee of the user as the lower leg is extended away from the upper leg via the knee, wherein the graphical animation includes the plurality of angles of extension as the plurality of angles of extension changes during the extension; (iii) store a lowest value, such as a smallest angle, of the plurality of angles of extension as an extension statistic for an extension session, wherein a plurality of extension statistics is stored for a plurality of extension sessions specified by the treatment plan; (iv) present progress of the plurality of extension sessions throughout the treatment plan via a graphical element presenting the plurality of extension statistics on the user interface; (v) determine whether a range of motion threshold condition is satisfied based on the plurality of angles of extension; and (vi) responsive to determining that the range of motion threshold condition is satisfied, transmit a threshold condition update to a second computing device to cause the second computing device to present the threshold condition update, via the one or more network interface cards.

From the following figures, descriptions, and claims, other technical features may be readily apparent to one skilled in the art.

Before undertaking the DETAILED DESCRIPTION below, it may be advantageous to set forth definitions of certain words and phrases used throughout this patent document. The term "couple" and its derivatives refer to any direct or indirect communication between two or more elements, independent of whether those elements are in physical contact with one another. The terms "transmit," "receive," and "communicate," as well as derivatives thereof, encompass both direct and indirect communication. The terms "include" and "comprise," as well as derivatives thereof, mean inclusion without limitation. The term "or" is inclusive, meaning and/or. The phrase "associated with," as well as derivatives thereof, means to include, be included within, interconnect with, contain, be contained within, connect to or with, couple to or with, be communicable with, cooperate with, interleave, juxtapose, be proximate to, be bound to or with, have, have a property of, have a relationship to or with, or the like. The term "controller" means any device, system or part thereof that controls at least one operation. Such a controller may be implemented in hardware or a combination of hardware and software and/or firmware. The functionality associated with any particular controller may be centralized or distributed, whether locally or remotely. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C.

Moreover, various functions described below can be implemented or supported by one or more computer programs, each of which is formed from computer readable program code and embodied in a computer readable medium. The terms "application" and "program" refer to one or more computer programs, software components, sets of instructions, procedures, functions, objects, classes, instances, related data, or portions thereof adapted for implementation in a suitable computer readable program code. The phrase "computer readable program code" includes any type of computer code, including source code, linked or linkable code, object code, and executable code. The phrase "computer readable medium" includes any type of medium capable of being accessed by a computer, such as read only memory (ROM), solid state device (SSD) memory, random access memory (RAM), a hard disk drive, a compact disc (CD), a digital video disc (DVD), or any other type of memory. A "non-transitory" computer readable medium excludes wired, wireless, optical, or other communication links that transport transitory electrical or other signals. A non-transitory computer readable medium includes media where data can be permanently stored and media where data can be stored and later overwritten, such as a rewritable optical disc or an erasable memory device.

Definitions for other certain words and phrases are provided throughout this patent document. Those of ordinary skill in the art should understand that in many if not most instances, such definitions apply to prior as well as to future uses of such defined words and phrases.

BRIEF DESCRIPTION OF THE DRAWINGS

For a more complete understanding of this disclosure and its advantages, reference is now made to the following description, taken in conjunction with the accompanying drawings, in which:

FIG. 5 illustrates example operations of a method for using a goniometer to measure angles of bend and/or extension of a lower leg relative to an upper leg according to certain embodiments of this disclosure;

DETAILED DESCRIPTION

Figure 1:
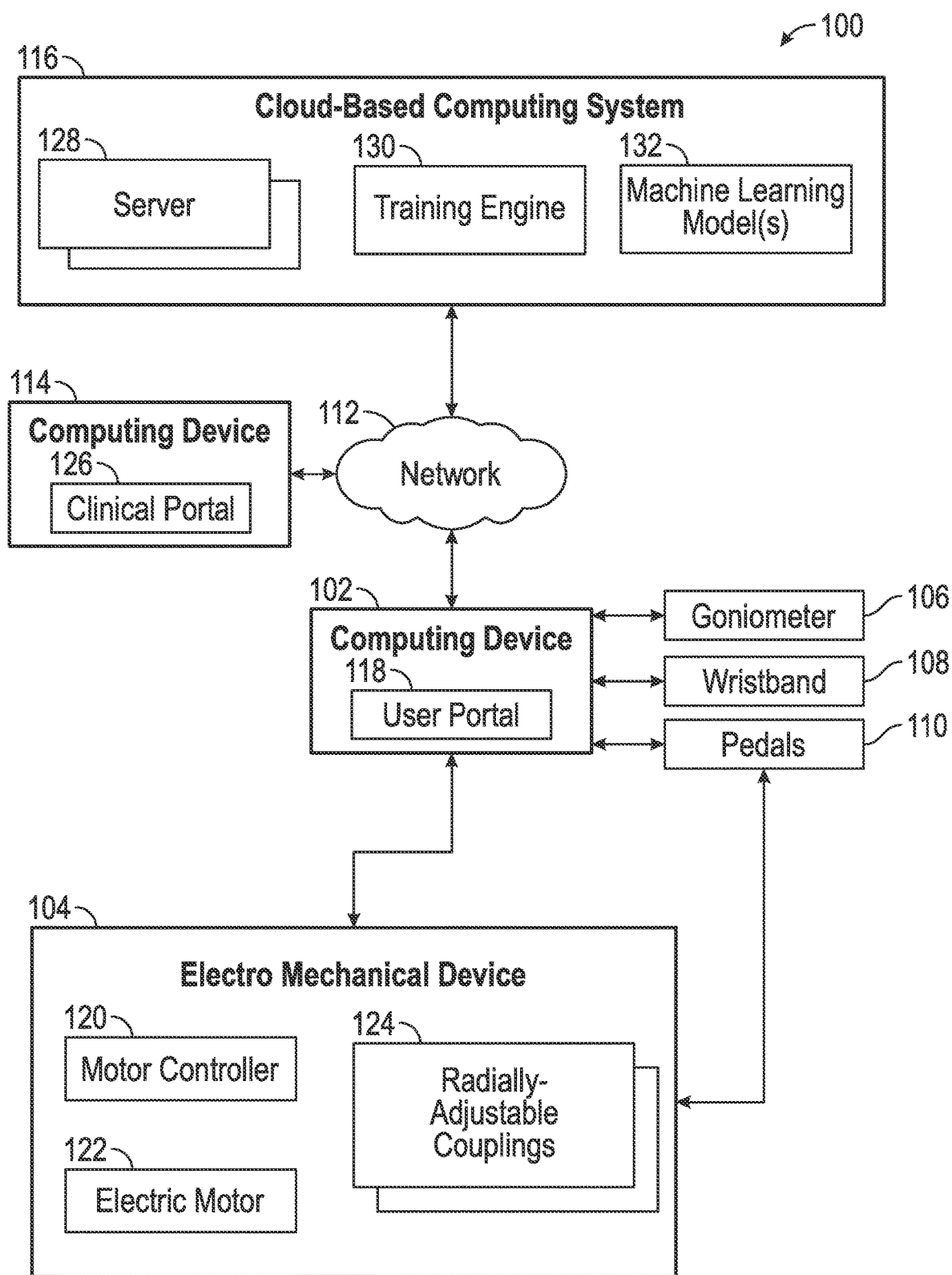
FIG. 1 illustrates a high-level component diagram of an illustrative rehabilitation system architecture according to certain embodiments of this disclosure.

Improvement is desired in the field of devices used for rehabilitation and exercise. People may sprain, fracture, tear or otherwise injure a body part and then consult a physician to diagnose the injury. In some instances, the physician may prescribe a treatment plan that includes operating one or more electromechanical devices (e.g., pedaling devices for arms or legs) for a period of time to exercise the affected area in an attempt to regain normal or closer-to-normal function by rehabilitating the injured body part and affected proximate areas. In other instances, the person with the injury may determine to operate a device without consulting a physician. In either scenario, the devices that are operated lack effective monitoring of (i) progress of rehabilitation of the affected area and (ii) control over the electromechanical device during operation by the user. Conventional devices lack components that enable the operation of the electromechanical device in various modes designed to improve the rate and/or enhance the effectiveness of rehabilitation. Further, conventional rehabilitation systems lack monitoring devices that aid in determining one or more properties of the user (e.g., range of motion of the affected area, heartrate of the user, etc.) and enable the adjustment of components based on the determined properties. When the user is supposed to be adhering to a treatment plan, conventional rehabilitation systems may not provide to the physician real-time results of sessions. That is, typically, the physicians have to rely on the patient's word as to whether he or she is adhering to the treatment plan. As a result of the abovementioned issues, conventional rehabilitation systems that use electromechanical devices may not provide effective and/or efficient rehabilitation of the affected body part.

Accordingly, aspects of the present disclosure generally relate to a control system for a rehabilitation and exercise electromechanical device (referred to herein as "electromechanical device" or "device"). The electromechanical device may include an electric motor configured to drive one or more radially-adjustable couplings to rotationally move pedals coupled to the radially-adjustable couplings. The electromechanical device may be operated by a user engaging the pedals with his or her hands or feet and rotating the pedals to exercise and/or rehabilitate a desired body part. The electromechanical device and the control system may be included as part of a larger rehabilitation system. The rehabilitation system may also include monitoring devices (e.g., goniometers, wristbands, force sensors in the pedals, etc.) that provide valuable information about the user to the control system. As such, the monitoring devices may be in direct or indirect communication with the control system.

The monitoring devices may include a goniometer configured to measure range of motion (e.g., angles of extension and/or bend) of a body part to which the goniometer is attached. The measured range of motion may be presented to the user and/or a physician via a user portal and/or a clinical portal. Also, to operate the electromechanical device during a treatment plan, the control system may use the measured range of motion to determine whether to adjust positions of the pedals on the radially-adjustable couplings and/or to change the mode types from one mode to another (e.g., from/to: passive, active-assisted, resistive, active) and/or durations. The monitoring devices may also include a wristband configured to track the steps of the user over a time period (e.g., a day, a week, etc.) and/or measure vital signs of the user (e.g., heartrate, blood pressure, oxygen level, etc.). The monitoring devices may also include force sensors disposed in the pedals and configured to measure the force exerted by the user on the pedals.

The control system may enable operating the electromechanical device in a variety of modes, such as a passive mode, an active-assisted mode, a resistive mode, and/or an active mode. The control system may use the information received from the measuring devices to adjust parameters (e.g., reduce resistance provided by electric motor, increase resistance provided by the electric motor, increase/decrease speed of the electric motor, adjust position of pedals on radially-adjustable couplings, etc.) while operating the electromechanical device in the various modes. The control system may receive the information from the monitoring devices, aggregate the information, make determinations using the information, and/or transmit the information to a cloud-based computing system for storage. The cloud-based computing system may maintain the information related to each user. As used herein, a cloud-based computing system refers, without limitation, to any remote computing system accessed over a network link.

A clinician and/or a machine learning model may generate a treatment plan for a user to rehabilitate a part of their body using at least the electromechanical device. A treatment plan may include a set of pedaling sessions using the electromechanical device, a set of joint extension sessions, a set of flex sessions, a set of walking sessions, a set of heartrate goals per pedaling session and/or walking session, and the like.

Each pedaling session may specify that a user is to operate the electromechanical device in a combination of one or more modes, including: passive, active-assisted, active, and resistive. The pedaling session may specify that the user is to wear the wristband and the goniometer during the pedaling session. Further, each pedaling session may include information specifying a set amount of time in which the electromechanical device is to operate in each mode, a target heartrate for the user during each mode in the pedaling session, target forces that the user is to exert on the pedals during each mode in the pedaling session, target ranges of motion the body parts are to attain during the pedaling session, positions of the pedals on the radially-adjustable couplings, and the like.

Each joint extension session may specify information relating to a target angle of extension at the joint, and each set of joint flex sessions may specify information relating to a target angle of flex at the joint. Each walking session may specify a target number of steps the user should take over a set period of time (e.g., a day, a week, etc.) and/or a target heartrate to achieve and/or maintain during the walking session.

The treatment plan may be stored in the cloud-based computing system and, when the user is ready to begin the treatment plan, downloaded to the computing device of the user. In some embodiments, the computing device that executes a clinical portal module (alternatively referred to herein as a clinical portal) may transmit the treatment plan to the computing device that executes a user portal and the user may initiate the treatment plan when ready.

In addition, the disclosed rehabilitation system may enable a physician to use the clinical portal to monitor the progress of the user in real-time. The clinical portal may present information pertaining to when the user is engaged in one or more sessions, statistics (e.g., speed, revolutions per minute, positions of pedals, forces on the pedals, vital signs, numbers of steps taken by user, ranges of motion, etc.) of the sessions, and the like. The clinical portal may also enable the physician to view before and after session images of the affected body part of the user to enable the physician to judge how well the treatment plan is working and/or to make adjustments to the treatment plan. The clinical portal may enable the physician, based on information received from the control system, to dynamically change a parameter (e.g., position of pedals, amount of resistance provided by electric motor, speed of the electric motor, duration of one of the modes, etc.) of the treatment plan in real-time.

The disclosed techniques provide numerous benefits over conventional systems. For example, to enhance the efficiency and effectiveness of rehabilitation of the user, the rehabilitation system provides granular control over the components of the electromechanical device. The control system enables, by controlling the electric motor, operating the electromechanical device in any suitable combination of the modes described herein. Further, the control system may use information received from the monitoring devices during a pedaling session to adjust parameters of components of the electromechanical device in real-time, for example. Additional benefits of this disclosure may include enabling a computing device operated by a physician to monitor the progress of a user participating in a treatment plan in real-time and/or to control operation of the electromechanical device during a pedaling session.

FIGS. 1 through 31, discussed below, and the various embodiments used to describe the principles of this disclosure are by way of illustration only and should not be construed in any way to limit the scope of the disclosure.

FIG. 1 illustrates a high-level component diagram of an illustrative rehabilitation system architecture 100 according to certain embodiments of this disclosure. In some embodiments, the system architecture 100 may include a computing device 102 communicatively coupled to an electromechanical device 104, a goniometer 106, a wristband 108, and/or pedals 110 of the electromechanical device 104. Each of the computing device 102, the electromechanical device 104, the goniometer 106, the wristband 108, and the pedals 110 may include one or more processing devices, memory devices, and network interface cards. The network interface cards may enable communication via a wireless protocol for transmitting data over short distances, such as Bluetooth, ZigBee, NFC, etc. In some embodiments, the computing device 102 is communicatively coupled via Bluetooth to the electromechanical device 104, goniometer 106, the wristband 108, and/or the pedals 110.

Additionally, the network interface cards may enable communicating data over long distances, and in one example, the computing device 102 may communicate with a network 112. Network 112 may be a public network (e.g., connected to the Internet via wired means (Ethernet) or wireless means (WiFi)), a private network (e.g., a local area network (LAN) or wide area network (WAN)), or a combination thereof. The computing device 102 may be communicatively coupled with a computing device 114 and a cloud-based computing system 116.

The computing device 102 may be any suitable computing device, such as a laptop, tablet, smartphone, computer or Internet of Things (IoT) sensor or device. (Other computing devices referenced herein may also be Internet of Things (IoT) sensors or devices.) The computing device 102 may include a display that is capable of presenting a user interface, such as a user portal 118. The user portal 118 may be implemented in computer instructions stored on the one or more memory devices of the computing device 102 and executable by the one or more processing devices of the computing device 102. The user portal 118 may present to a user various screens that enable the user to view a treatment plan, initiate a pedaling session for the purpose of executing the treatment plan, control parameters of the electromechanical device 104, view progress of rehabilitation during the pedaling session, and so forth as described in more detail below. The computing device 102 may also include instructions stored on the one or more memory devices that, when executed by the one or more processing devices of the computing device 102, perform operations to control the electromechanical device 104.

The computing device 114 may execute a clinical portal 126. The clinical portal 126 may be implemented in computer instructions stored on the one or more memory devices of the computing device 114 and executable by the one or more processing devices of the computing device 114. The clinical portal 126 may present to a physician or a clinician various screens that enable the physician to create a treatment plan for a patient or user, view progress of the user throughout the treatment plan, view measured properties (e.g., angles of bend/extension, force exerted on the pedals 110, heart rate, steps taken, images of the affected body part) of the user during sessions of the treatment plan, and/or view properties (e.g., modes completed, revolutions per minute, etc.) of the electromechanical device 104 during sessions of the treatment plan. So the patient may begin the treatment plan, the treatment plan specific to a patient may be transmitted via the network 112 to the cloud-based computing system 116 for storage and/or to the computing device 102. The terms "patient" and "user" may be used interchangeably throughout this disclosure.

The electromechanical device 104 may be an adjustable pedaling device for exercising and rehabilitating arms and/or legs of a user. The electromechanical device 104 may include at least one or more motor controllers 120, one or more electric motors 122, and one or more radially-adjustable couplings 124. Two pedals 110 may be coupled to two radially-adjustable couplings 124 via left and right pedal assemblies that each include respective stepper motors. The motor controller 120 may be operatively coupled to the electric motor 122 and configured to provide commands to the electric motor 122 to control operation of the electric motor 122. The motor controller 120 may include any suitable microcontroller including a circuit board having one or more processing devices, one or more memory devices (e.g., read-only memory (ROM) and/or random access memory (RAM)), one or more network interface cards, and/or programmable input/output peripherals. The motor controller 120 may provide control signals or commands to drive the electric motor 122. The electric motor 122 may be powered to drive one or more radially-adjustable couplings 124 of the electromechanical device 104 in a rotational manner. The electric motor 122 may provide the driving force to rotate the radially-adjustable couplings 124 at configurable speeds. The couplings 124 are radially-adjustable in that a pedal 110 attached to the coupling 124 may be adjusted to a number of positions on the coupling 124 in a radial fashion. Further, the electromechanical device 104 may include a current shunt to provide resistance to dissipate energy from the electric motor 122. As such, the electric motor 122 may be configured to provide resistance to rotation of the radially-adjustable couplings 124.

The computing device 102 may be communicatively connected to the electromechanical device 104 via the network interface card on the motor controller 120. The computing device 102 may transmit commands to the motor controller 120 to control the electric motor 122. The network interface card of the motor controller 120 may receive the commands and transmit the commands to the electric motor 122 to drive the electric motor 122. In this way, the computing device 102 is operatively coupled to the electric motor 122.

The computing device 102 and/or the motor controller 120 may be referred to as a control system herein. The user portal 118 may be referred to as a user interface of the control system herein. The control system may control the electric motor 122 to operate in a number of modes: passive, active-assisted, resistive, and active. The passive mode may refer to the electric motor 122 independently driving the one or more radially-adjustable couplings 124 rotationally coupled to the one or more pedals 110. In the passive mode, the electric motor 122 may be the only source of driving force on the radially-adjustable couplings. That is, the user may engage the pedals 110 with their hands or their feet and the electric motor 122 may rotate the radially-adjustable couplings 124 for the user. This may enable moving the affected body part and stretching the affected body part without the user exerting excessive force.

The active-assisted mode may refer to the electric motor 122 receiving measurements of revolutions per time period, such as a revolutions per minute, second, or any other desired time interval, of the one or more radially-adjustable couplings 124, and, when the measured revolutions per time period satisfy a threshold condition, causing the electric motor 122 to drive the one or more radially-adjustable couplings 124 rotationally coupled to the one or more pedals 110. The threshold condition may be configurable by the user and/or the physician. As long as the revolutions per time period are above a revolutions per time period threshold (e.g., revolutions threshold 1732) and the threshold condition is not satisfied, the electric motor 122 may be powered off while the user provides the driving force to the radially-adjustable couplings 124. When the revolutions per time period are less than the revolutions per minute threshold, then the threshold condition is satisfied and the electric motor 122 may be controlled to drive the radially-adjustable couplings 124 to maintain the revolutions per time period threshold.

The resistive mode may refer to the electric motor 122 providing resistance to rotation of the one or more radially-adjustable couplings 124 coupled to the one or more pedals 110. The resistive mode may increase the strength of the body part being rehabilitated by causing the muscle to exert force to move the pedals 110 against the resistance provided by the electric motor 122.

The active mode may refer to the electric motor 122 powering off to provide no driving force assistance to the radially-adjustable couplings 124. Instead, in this mode, the user, using their hands or feet, for example, provides the sole driving force of the radially-adjustable couplings.

During one or more of the modes, each of the pedals 110 may measure force exerted by a part of the body of the user on the pedal 110. For example, the pedals 110 may each contain any suitable sensor (e.g., strain gauge load cell, piezoelectric crystal, hydraulic load cell, etc.) for measuring force exerted on the pedal 110. Further, the pedals 110 may each contain any suitable sensor for detecting whether the body part of the user separates from contact with the pedals 110. In some embodiments, the measured force may be used to detect whether the body part has separated from the pedals 110. The force detected may be transmitted via the network interface card of the pedal 110 to the control system (e.g., computing device 102 and/or motor controller 120). As described further below, the control system may, based on the measured force, modify a parameter of operating the electric motor 122. Further, the control system may perform one or more preventative actions (e.g., locking the electric motor 122 to stop the radially-adjustable couplings 124 from moving, slowing down the electric motor 122, presenting a notification to the user, etc.) when the body part is detected as separated from the pedals 110, among other things.

The goniometer 106 may be configured to measure angles of extension and/or bend of body parts and to transmit the measured angles to the computing device 102 and/or the computing device 114. The goniometer 106 may be included in an electronic device that includes the one or more processing devices, memory devices, and/or network interface cards. The goniometer 106 may be attached to the user's body, for example, to an upper leg and a lower leg. The goniometer 106 may be coupled to the user via a strap, an adhesive, a mechanical brace, or any other desired attachment. The goniometer 106 may be disposed in a cavity of the mechanical brace. The cavity of the mechanical brace may be located near a center of the mechanical brace where the mechanical brace affords to bend and extend. The mechanical brace may be configured to secure to an upper body part (e.g., arm, etc.) and a lower body part (e.g., leg, etc.) to measure the angles of bend as the body parts are extended away from one another or retracted closer to one another.

The wristband 108 may include a 3-axis accelerometer to track motion in the X, Y, and Z directions, an altimeter for measuring altitude, and/or a gyroscope to measure orientation and rotation. The accelerometer, altimeter, and/or gyroscope may be operatively coupled to a processing device in the wristband 108 and may transmit data to the processing device. The processing device may cause a network interface card to transmit the data to the computing device 102 and the computing device 102 may use the data representing acceleration, frequency, duration, intensity, and patterns of movement to track steps taken by the user over certain time periods (e.g., days, weeks, etc.). The computing device 102 may transmit the steps to the computing device 114 executing a clinical portal 126. Additionally, in some embodiments, the processing device of the wristband 108 may determine the steps taken and transmit the steps to the computing device 102. In some embodiments, the wristband 108 may use photoplethysmography (PPG) to measure heartrate that detects an amount of red light or green light on the skin of the wrist. For example, blood may absorb green light so when the heart beats, the blood flow may absorb more green light, thereby enabling the detection of heartrate. The heartrate may be sent to the computing device 102 and/or the computing device 114.

The computing device 102 may present the steps taken by the user and/or the heartrate via respective graphical elements on the user portal 118, as discussed further below. The computing device may also use the steps taken and/or the heart rate to control a parameter of operating the electromechanical device 104. For example, if the heartrate exceeds a target heartrate for a pedaling session, the computing device 102 may control the electric motor 122 to reduce resistance being applied to rotation of the radially-adjustable couplings 124. In another example, if the steps taken are below a step threshold for a day, the treatment plan may increase the amount of time for one or more modes in which the user is to operate the electromechanical device 104 to ensure the affected body part is getting sufficient movement by reaching or exceeding the step threshold.

In some embodiments, the cloud-based computing system 116 may include one or more servers 128 that form a distributed computing architecture. Each of the servers 128 may include one or more processing devices, memory devices, data storage, and/or network interface cards. The servers 128 may be in communication with one another via any suitable communication protocol. The servers 128 may store profiles for each of the users that use the electromechanical device 104. The profiles may include information about the users, such as respective treatment plans, the affected body parts, any procedures the users had performed on the affected body parts, health, age, race, measured data from the goniometer 106, measured data from the wristband 108, measured data from the pedals 110, user input received at the user portal 118 during operation of any of the modes of the treatment plan, a specification of a level of discomfort, comfort, or general patient satisfaction that the user experiences before and after any of the modes, before and after session images of the affected body part, and so forth.

In some embodiments, the cloud-based computing system 116 may include a training engine 130 capable of generating one or more machine learning models 132. The machine learning models 132 may be trained to generate treatment plans for the patients in response to receiving various inputs (e.g., a procedure performed on the patient, an affected body part on which the procedure was performed, other health characteristics or demographic attributes (e.g., age, race, fitness level, etc.)). The one or more machine learning models 132 may be generated by the training engine 130 and may be implemented in computer instructions executable by one or more processing devices of the training engine 130 and/or the servers 128. To generate the one or more machine learning models 132, the training engine 130 may train the one or more machine learning models 132. The training engine 130 may use a base data set of patient characteristics, treatment plans followed by the patient, and results of the treatment plans followed by the patients. The results may include information indicating whether a given treatment plan led to full recovery of the affected body part, partial recovery of the affected body part, or lack of recovery of the affected body part, and the degree to which such recovery was achieved. The training engine 130 may be a rackmount server, a router computer, a personal computer, a portable digital assistant, a smartphone, a laptop computer, a tablet computer, a camera, a video camera, a netbook, a desktop computer, a media center, an IoT device, or any combination of the above. The one or more machine learning models 132 may refer to model artifacts that are created by the training engine 130 using training data that includes training inputs and corresponding target outputs. The training engine 130 may find patterns in the training data that map the training input to the target output, and generate the machine learning models 132 that capture these patterns. Although depicted separately from the computing device 102, in some embodiments, the training engine 130 and/or the machine learning models 132 may reside on the computing device 102 and/or the computing device 114.

The machine learning models 132 may include one or more of a neural network, such as an image classifier, recurrent neural network, convolutional network, generative adversarial network, a fully connected neural network, or some combination thereof, for example. In some embodiments, the machine learning models 132 may be composed of a single level of linear or non-linear operations or may include multiple levels of non-linear operations. For example, the machine learning model 132 may include numerous layers and/or hidden layers that perform calculations (e.g., dot products) using various neurons. The rehabilitation system architecture 100 can include additional and/or fewer components and is not limited to those illustrated in FIG. 1.

Figure 2:
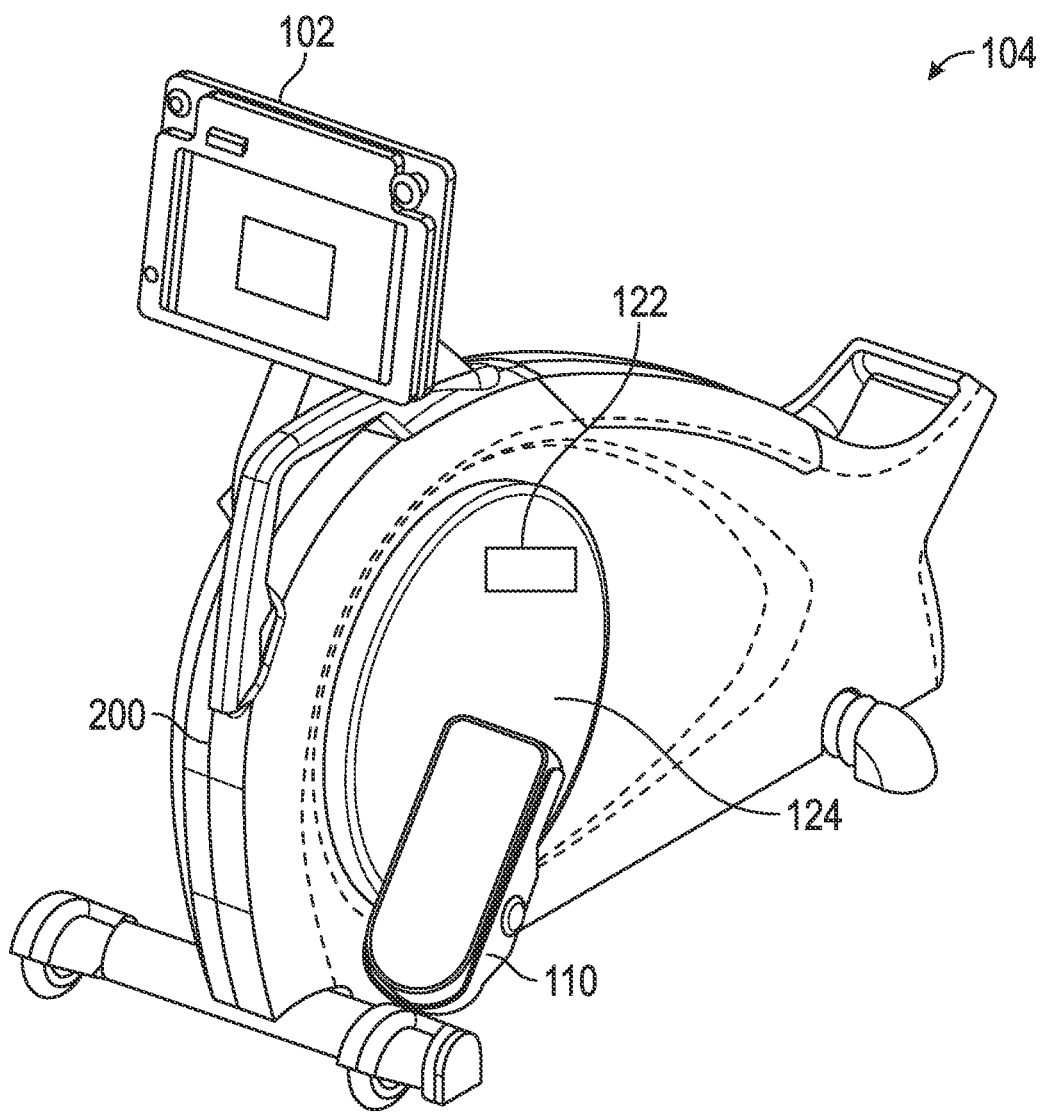
FIG. 2 illustrates a perspective view of an example of an exercise and rehabilitation device according to certain embodiments of this disclosure.

FIG. 2 illustrates a perspective view of an example of an exercise and rehabilitation device, such as the electromechanical device 104, according to certain embodiments of this disclosure. The electromechanical device 104 is shown having pedals 110 on opposite sides and which are adjustably positionable relative to one another on respective radially-adjustable couplings 124. The electromechanical device 104 is configured as a small and portable unit so that it is easily transported to different locations at which rehabilitation or treatment is to be provided, such as at patients' homes, alternative care facilities, or the like. The patient may sit in a chair proximate the electromechanical device 104 to engage the electromechanical device 104 with their feet, for example.

The electromechanical device 104 includes a rotary device such as radially-adjustable couplings 124 or a flywheel or flywheels or the like rotatably mounted such as by a central hub to a frame 200 or other support. The pedals 110 are configured for interacting with a patient to be rehabilitated and may be configured for use with lower body extremities such as the feet, legs, and the like, or with upper body extremities, such as the hands, arms, and the like. For example, the pedal 110 may be a bicycle pedal of the type having a foot support rotatably mounted onto an axle with bearings. To locate the pedal on the radially-adjustable coupling 12. the axle may or may not have exposed end threads for engaging a mount on the radially-adjustable coupling 124. The radially-adjustable coupling 124 may include an actuator configured to radially adjust the location of the pedal to various positions on the radially-adjustable coupling 124.

Alternatively, the radially-adjustable coupling 124 may be configured to have both pedals 110 on opposite sides of a single coupling 124. In some embodiments, as depicted, a pair of radially-adjustable couplings 124 may be spaced apart from one another but interconnected to the electric motor 122. In the depicted example, the computing device 102 may be mounted on the frame 200 and may be detachable and held by the user while the user operates the electromechanical device 104. The computing device 102 may present the user portal and control the operation of the electric motor 122, as described herein.

In some embodiments, as described in U.S. Pat. No. 10,173,094 (U.S. application Ser. No. 15/700,293), which is incorporated by reference herein in its entirety for all purposes, the electromechanical device 104 may take the form of a traditional exercise/rehabilitation device which is more or less non-portable and remains in a fixed location, such as a rehabilitation clinic or medical practice. This embodiment of the electromechanical device 104 may include a seat and is less portable than the electromechanical device 104 shown in FIG. 2.

Figure 3:
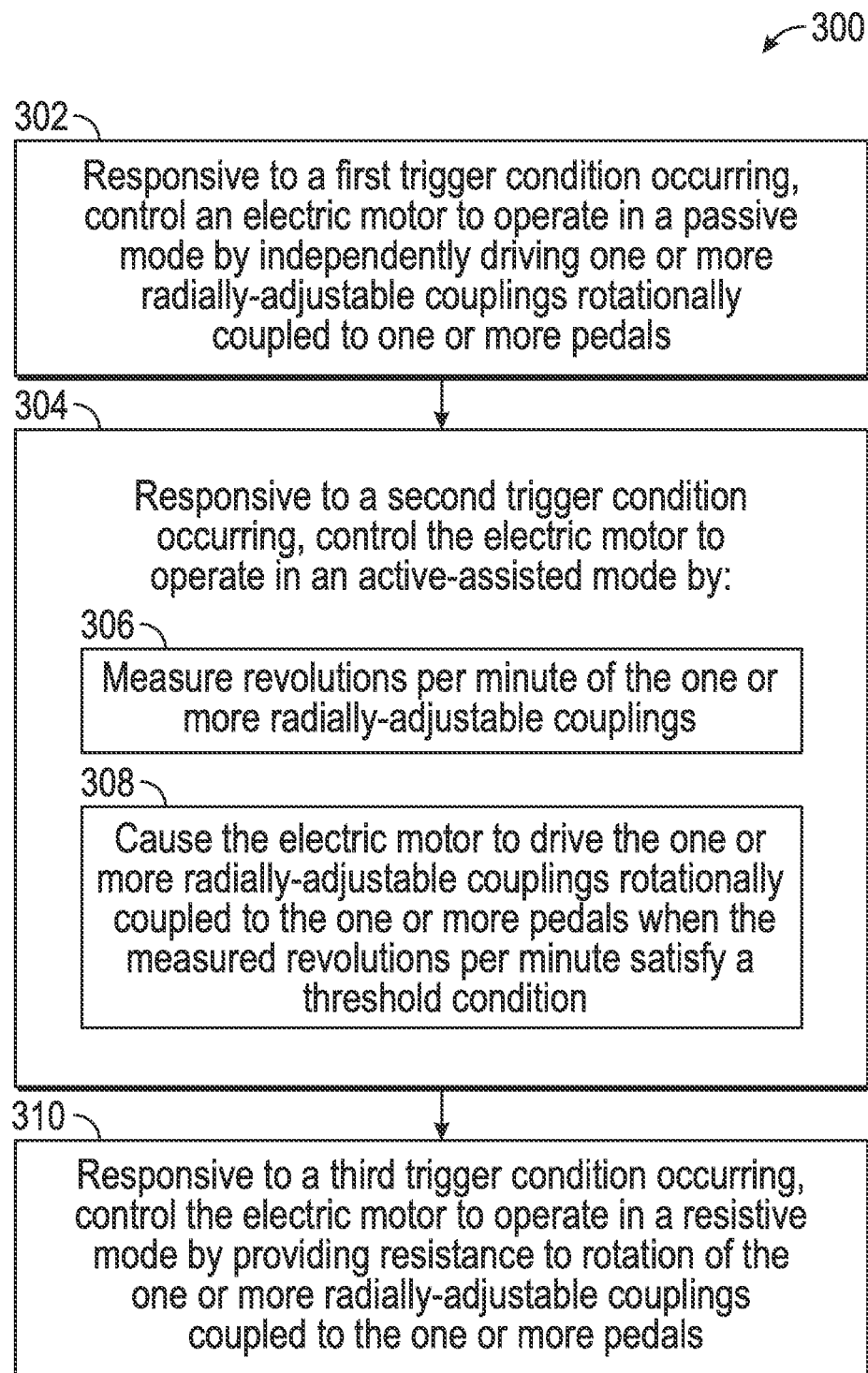
FIG. 3 illustrates example operations of a method for controlling an electromechanical device for rehabilitation in various modes according to certain embodiments of this disclosure.

FIG. 3 illustrates example operations of a method 300 for controlling an electromechanical device for rehabilitation in various modes according to certain embodiments of this disclosure. The method 300 may be performed by processing logic that may include hardware (circuitry, dedicated logic, etc.), firmware, software, or a combination of them. The method 300 and/or each of their individual functions, subroutines, or operations may be performed by one or more processors of a control system (e.g., computing device 102 of FIG. 1) implementing the method 300. The method 300 may be implemented as computer instructions that, when executed by a processing device, execute the user portal 118. In certain implementations, the method 300 may be performed by a single processing thread. Alternatively, the method 300 may be performed by two or more processing threads, each thread implementing one or more individual functions, routines, subroutines, or operations of the methods. Various operations of the method 300 may be performed by one or more of the cloud-based computing system 116, the motor controller 120, the pedals 110, the goniometer 106, the wristband 108, and/or the computing device 114 of FIG. 1.

As discussed above, an electromechanical device may include one or more pedals coupled to one or more radially-adjustable couplings, an electric motor coupled to the one or more pedals via the one or more radially-adjustable couplings, and the control system including one or more processing devices operatively coupled to the electric motor. In some embodiments, the control system (e.g., computing device 102 and/or motor controller 120) may store instructions and one or more operations of the control system may be presented via the user portal. In some embodiments, the radially-adjustable couplings are configured for translating rotational motion of the electric motor to radial motion of the pedals.

At block 302, responsive to a first trigger condition occurring, the processing device may control the electric motor to operate in a passive mode by independently driving the one or more radially-adjustable couplings rotationally coupled to the one or more pedals. "Independently drive" may refer to the electric motor driving the one or more radially-adjustable couplings without the aid of another driving source (e.g., the user). The first trigger condition may include an initiation of a pedaling session via the user interface of the control system, a period of time elapsing, a detected physical condition (e.g., heartrate, oxygen level, blood pressure, etc.) of a user operating the electromechanical device, a request received from the user via the user interface, or a request received via a computing device communicatively coupled to the control system (e.g., a request received from the computing device executing the clinical portal). While operating in the passive mode, the processing device may control the electric motor to independently drive the one or more radially-adjustable couplings rotationally coupled to the one or more pedals at a controlled speed specified in a treatment plan for a user operating the electromechanical device.

In some embodiments, the electromechanical device may be configured such that the processor controls the electric motor to individually drive the radially-adjustable couplings. For example, the processing device may control the electric motor to individually drive the left or right radially-adjustable coupling, while allowing the user to provide the force to drive the other radially-adjustable coupling. As another example, the processing device may control the electric motor to drive both the left and right radially-adjustable couplings but at different speeds. This granularity of control may be beneficial by controlling the speed at which a healing body part is moved (e.g., rotated, flexed, extended, etc.) to avoid tearing tendons or causing pain to the user.

At block 304, responsive to a second trigger condition occurring, the processing device may control the electric motor to operate in an active-assisted mode by measuring (block 306) revolutions per minute of the one or more radially-adjustable couplings, and causing (block 308) the electric motor to drive the one or more radially-adjustable couplings rotationally coupled to the one or more pedals when the measured revolutions per minute satisfy a threshold condition. The second trigger condition may include an initiation of a pedaling session via the user interface of the control system, a period of time elapsing, a detected physical condition (e.g., heartrate, oxygen level, blood pressure, etc.) of a user operating the electromechanical device, a request received from the user via the user interface, or a request received via a computing device communicatively coupled to the control system (e.g., a request received from the computing device executing the clinical portal). The threshold condition may be satisfied when the measured revolutions per minute are less than a minimum revolutions per minute. In such an instance, the electric motor may begin driving the one or more radially-adjustable couplings to increase the revolutions per minute of the radially-adjustable couplings.

As with the passive mode, in the active-assisted mode, the processing device may control the electric motor to individually drive the one or more radially-adjustable couplings. For example, if just a right knee is being rehabilitated, the revolutions per minute of the right radially-adjustable coupling may be measured and the processing device may control the electric motor to individually drive the right radially-adjustable coupling when the measured revolutions per minute are less than the minimum revolutions per minute. In some embodiments, there may be different minimum revolutions per minute set for the left radially-adjustable coupling and the right radially-adjustable coupling, and the processing device may control the electric motor to individually drive the left radially-adjustable coupling and the right radially-adjustable coupling as appropriate to maintain the different minimum revolutions per minute.

At block 310, responsive to a third trigger condition occurring, the processing device may control the electric motor to operate in a resistive mode by providing resistance to rotation of the one or more radially-adjustable couplings coupled to the one or more pedals. The third trigger condition may include an initiation of a pedaling session via the user interface of the control system, a period of time elapsing, a detected physical condition (e.g., heartrate, oxygen level, blood pressure, etc.) of a user operating the electromechanical device, a request received from the user via the user interface, or a request received via a computing device communicatively coupled to the control system (e.g., a request received from the computing device executing the clinical portal).

In some embodiments, responsive to a fourth trigger condition occurring, the processing device may be further configured to control the electric motor to operate in an active mode by powering off to enable another source (e.g., the user) to drive the one or more radially-adjustable couplings via the one or more pedals. In the active mode, the another source may drive the one or more radially-adjustable couplings at any desired speed via the one or more pedals.

In some embodiments, the processing device may control the electric motor to operate in each of the passive mode, the active-assisted mode, the resistive mode, and/or the active mode for a respective period of time during a pedaling session (e.g., based on a treatment plan for a user operating the electromechanical device). In some embodiments, the various modes and the respective periods of time may be selected by a clinician that sets up the treatment plan using the clinical portal. In some embodiments, the various modes and the respective periods of time may be selected by a machine learning model trained to receive parameters (e.g., procedure performed on the user, body part on which the procedure was performed, health of the user) and to output a treatment plan to rehabilitate the affected body part, as described above.

In some embodiments, the processing device may modify one or more positions of the one or more pedals on the one or more radially-adjustable couplings to change one or more diameters of ranges of motion of the one or more pedals during any of the passive mode, the active-assisted mode, the resistive mode, and/or the active mode throughout a pedaling session for a user operating the electromechanical device. The processing device may further be configured to modify the position of one of the one or more pedals on one of the one or more radially-adjustable couplings to change the diameter of the range of motion of the one of the one or more pedals while maintaining another position of another of the one or more pedals on another of the one or more radially-adjustable couplings to maintain another diameter of another range of motion of another pedal. In some embodiments, the processing device may cause both positions of the pedals to move to change the diameter of the range of motion for both pedals. The amount of movement of the positions of the pedals may be individually controlled in order to provide different diameters of ranges of motions of the pedals as desired.

In some embodiments, the processing device may receive, from the goniometer worn by the user operating the electromechanical device, at least one of an (i) angle of extension of a joint of the user during a pedaling session or an (ii) angle of bend of the joint of the user during the pedaling session. In some instances, the joint may be a knee or an elbow. The goniometer may be configured to measure the angles of bend and/or extension of the joint and to continuously, continually, or periodically transmit the angle measurements received by the processing device. The processing device may modify the positions of the pedals on the radially-adjustable couplings to change the diameters of the ranges of motion of the pedals based on the at least one of the angle of extension of the joint of the user or the angle of bend of the joint of the user.

In some embodiments, the processing device may receive, from the goniometer worn by the user, a set of angles of extension between an upper leg and a lower leg at a knee of the user as the user extends the lower leg away from the upper leg via the knee. In some embodiments, the goniometer may send the set of angles of extension between an upper arm, upper body, etc. and a lower arm, lower body, etc. The processing device may present, on a user interface of the control system, a graphical animation of the upper leg, the lower leg, and the knee of the user as the lower leg is extended away from the upper leg via the knee. The graphical animation may include the set of angles of extension as the set of angles of extension changes during the extension. The processing device may store, in a data storage of the control system, a lowest value of the set of angles of extension as an extension statistic for an extension session. A set of extension statistics may be stored for a set of extension sessions specified by the treatment plan. The processing device may present progress of the set of extension sessions throughout the treatment plan via a graphical element (e.g., line graph, bar chart, etc.) on the user interface presenting the set of extension statistics.

In some embodiments, the processing device may receive, from the goniometer worn by the user, a set of angles of bend or flex between an upper leg and a lower leg at a knee of the user as the user retracts the lower leg closer to the upper leg via the knee. In some embodiments, the goniometer may send the set of angles of bend between an upper arm, upper body, etc. and a lower arm, lower body, etc. The processing device may present, on a user interface of the control system, a graphical animation of the upper leg, the lower leg, and the knee of the user as the lower leg is retracted closer to the upper leg via the knee. The graphical animation may include the set of angles of bend as the set of angles of bend changes during the bending. The processing device may store, in a data storage of the control system, a highest value of the set of angles of bend as a bend statistic for a bend session. A set of bend statistics may be stored for a set of bend sessions specified by the treatment plan. The processing device may present progress of the set of bend sessions throughout the treatment plan via a graphical element (e.g., line graph, bar chart, etc.) on the user interface presenting the set of bend statistics.

In some embodiments, the angles of extension and/or bend of the joint may be transmitted by the goniometer to a computing device executing a clinical portal. A clinician may operate the computing device executing the clinical portal. The clinical portal may present a graphical animation in real-time of the upper leg extending away from the lower leg and/or the upper leg bending closer to the lower leg during a pedaling session, extension session, and/or a bend session of the user. In some embodiments, the clinician may provide notifications to the computing device to present via the user portal. The notifications may indicate that the user has satisfied a target extension and/or bend angle. Other notifications may indicate that the user has extended or retracted a body part too far and should cease the extension and/or bend session. In some embodiments, the computing device executing the clinical portal may transmit a control signal to the control system to move a position of a pedal on the radially-adjustable coupling based on the angle of extension or angle of bend received from the goniometer. That is, the clinician can in real-time increase a diameter of range of motion for a body part of the user based on the measured angles of extension and/or bend during a pedaling session.

This may enable the clinician to dynamically control the pedaling session to enhance the rehabilitation results of the pedaling session.

In some embodiments, the processing device may receive, from a wearable device (e.g., a wristband), a number of steps taken by a user over a certain time period (e.g., a day, a week, etc.). The processing device may calculate whether the number of steps satisfies a step threshold of a walking session of a treatment plan for the user. The processing device may be configured to present on a user interface of the control system the number of steps taken by the user and may be configured to present an indication of whether the number of steps satisfies the step threshold.

The wearable device, which is interchangeably described herein as a wristband, though a person having ordinary skill in the art will readily comprehend in light of having read the present disclosure that other varieties of wearable devices may also be used without departing from the scope and intent of the present disclosure, may also measure one or more vital statistics of the user, such as a heartrate, oxygen level, blood pressure, and the like. The measurements of the vital statistics may be performed at any suitable time, such as during a pedaling session, walking session, extension session, bend session, and/or any other desired session. The wristband may transmit the one or more vital statistics to the control system. The processing device of the control system may use the vital statistics to determine whether to reduce resistance the electric motor is providing for the purpose of lowering one of the vital statistics (e.g., heartrate) when that vital statistic is above a threshold, to determine whether the user is in pain when one of the vital statistics is elevated beyond a threshold, to determine whether to provide a notification indicating the user should take a break or increase the intensity of the appropriate session, and so forth.

In some embodiments, the processing device may receive a request to stop the one or more pedals from moving. The request may be received by a user selecting on the user portal of the control system a graphical icon representing "stop." The processing device may cause the electric motor to lock and stop the one or more pedals from moving over a configured period of time (e.g., instantly, over 1 second, 2 seconds, 3 seconds, 5 seconds, 10 seconds, or any period of time less than those, more than those or in between those, etc.). One benefit of including an electric motor in the electromechanical device is that the motor can be configured to provide the ability to stop the movement of the pedals as soon as a user desires.

In some embodiments, the processing device may receive, from one or more force sensors operatively coupled to the one or more pedals and the one or more processing devices, one or more measurements of force on the one or more pedals. The force sensors may be operatively coupled to the one or more processing devices via a wireless connection (e.g., Bluetooth) enabled by wireless circuitry in the pedals. The processing device may determine, based on the one or more measurements of force, whether the user has fallen from the electromechanical device. Responsive to determining that the user has fallen from the electromechanical device, the processing device may lock the electric motor to stop the one or more pedals from moving.

Additionally or alternatively, the processing device may determine, based on the one or more measurements of force that the user's feet or hands have separated from the pedals. Responsive to determining that the feet or hands have separated from the pedals, the processing device may lock the electric motor to stop the one or more pedals from moving. Also, the processing device may present a notification on a user interface of the control system, such notification instructing the user to place their feet or hands in contact with the pedals.

In some embodiments, the processing device may receive, from the force sensors operatively coupled to the one or more pedals, the measurements of force exerted by a user on the pedals during a pedaling session. While the user pedals during the pedaling session, the processing device may present the respective measurements of force on each of the pedals on a separate respective graphical scale on the user interface of the control system. Various graphical indicators may be presented on the user interface to indicate when the force is below a threshold target range, is within the threshold target range, and/or exceeds the threshold target range. Notifications may be presented to encourage the user to apply more force and/or less force to achieve the threshold target range of force. For example, the processing device may be configured to present a first notification on the user interface after the one or more measurements of force satisfy a pressure threshold and to present a second notification on the user interface after the one or more measurements do not satisfy the pressure threshold.

In addition, the processing device may provide an indicator to the user based on the one or more measurements of force. The indicator may include at least one of (1) providing haptic feedback in the pedals, handles, and/or seat of the electromechanical device, (2) providing visual feedback on the user interface (e.g., an alert, a light, a sign, etc.), (3) providing audio feedback via an audio subsystem (e.g., speaker) of the electromechanical device, or (4) illuminating a warning light of the electromechanical device.

In some embodiments, the processing device may receive, from an accelerometer of the control system, motor controller, pedal, or the like, a measurement of acceleration of movement of the electromechanical device. The processing device may determine whether the electromechanical device has moved excessively relative to a vertical axis (e.g., fallen over) based on the measurement of acceleration. Responsive to determining that the electromechanical device has moved excessively relative to the vertical axis based on the measurement of acceleration, the processing device may lock the electric motor to stop the one or more pedals from moving.

After a pedaling session is complete, the processing device may lock the electric motor to prevent the one or more pedals from moving a certain amount of time after the completion of the pedaling session. This may enable healing of the body part being rehabilitated and prevent strain on that body part by excessive movement. Upon expiration of the certain amount of time, the processing device may unlock the electric motor to enable movement of the pedals again.

The computing device can include a user portal. The user portal may provide an option to image the body part being rehabilitated. The user portal may include a display and a camera. For example, the user may place the body part within an image capture section, such as a camera, of the user portal and select an icon to capture an image of the body part. An icon, such as a camera icon, may be located on a display of the user portal. The user may select the camera icon to use the camera to capture an image or to take a photograph of a site of the body of the user. The site may be a body part such as a leg, arm, joint, such as a knee or an elbow, or any other desired site of the body of the user. The processing device can execute the instructions to store the image or photograph. The processing device may execute the instructions to transmit the image or photograph to a clinical portal. The images may be captured before and after a pedaling session, walking session, extension session, and/or bend session. These images may be sent to the cloud-based computing system to use as training data to enable the machine-learning model to determine the effects of the session. Further, the images may be sent to the computing device executing the clinical portal to enable the clinician to view the results of the sessions and modify the treatment plan if desired and/or provide notifications (e.g., reduce resistance, increase resistance, extend the joint further or less, etc.) to the user if desired.

Figure 4:
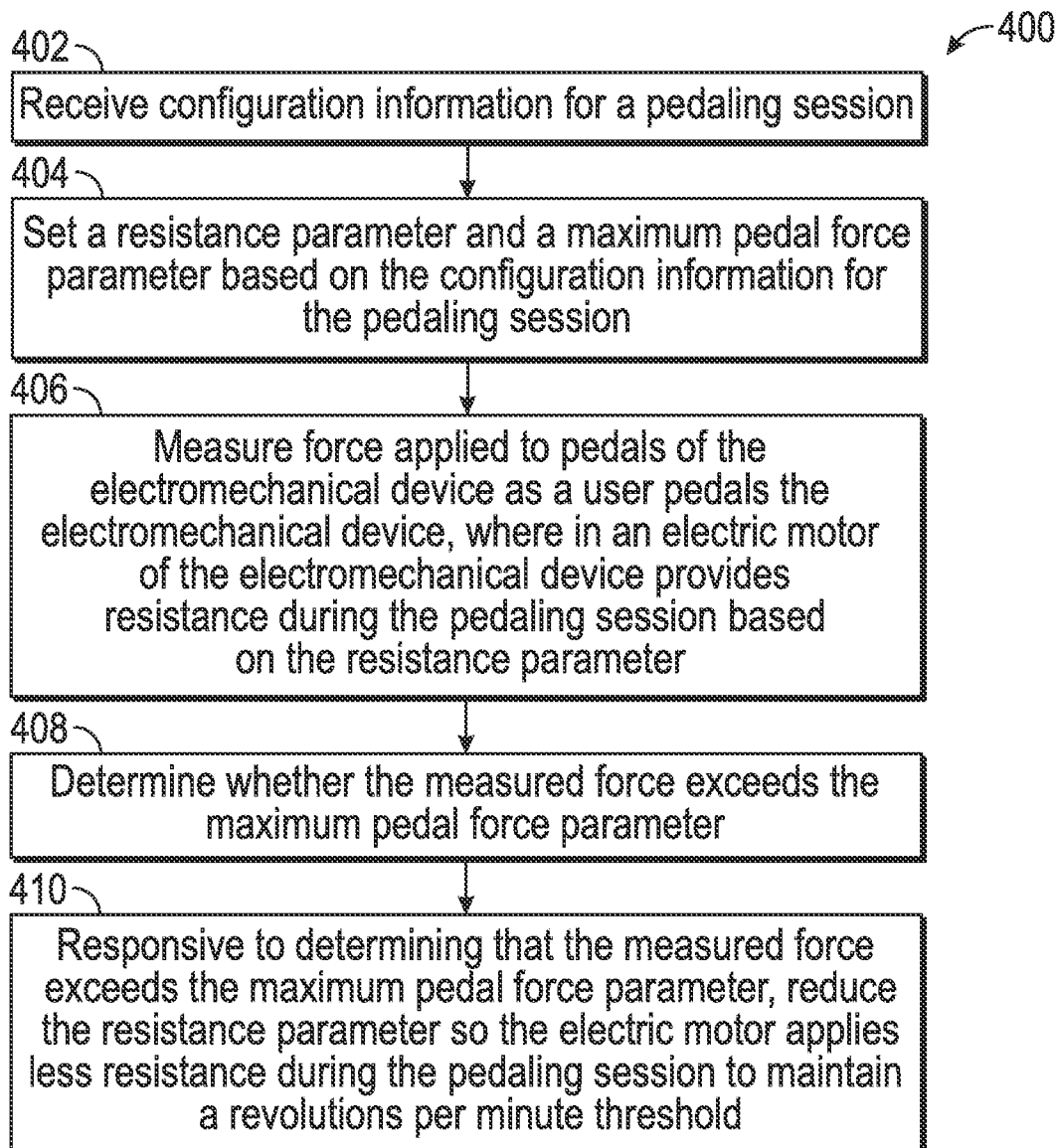
FIG. 4 illustrates example operations of a method for controlling an amount of resistance provided by an electromechanical device according to certain embodiments of this disclosure.

FIG. 4 illustrates example operations of a method 400 for controlling an amount of resistance provided by an electromechanical device according to certain embodiments of this disclosure. Method 400 includes operations performed by processing devices of the control system (e.g., computing device 102) of FIG. 1. In some embodiments, one or more operations of the method 400 are implemented in computer instructions that, when executed by a processing device, execute the control system and/or the user portal. Various operations of the method 400 may be performed by one or more of the computing device 114, the cloud-based computing system 116, the motor controller 120, the pedal 110, the goniometer 106, and/or the wristband 108. The method 400 may be performed in the same or a similar manner as described above in regards to method 300.

At block 402, the processing device may receive configuration information for a pedaling session. The configuration information may be received via selection by the user on the user portal executing on the computing device, received from the computing device executing the clinical portal, downloaded from the cloud-based computing system, retrieved from a memory device of the computing device executing the user portal, or some combination thereof. For example, the clinician may select the configuration information for a pedaling session of a patient using the clinical portal and upload the configuration information from the computing device to a server of the cloud-based computing system.

The configuration information for the pedaling session may specify one or more modes in which the electromechanical device is to operate, and configuration information specific to each of the modes, an amount of time to operate each mode, and the like. For example, for a passive mode, the configuration information may specify a position for the pedal to be in on the radially-adjustable couplings and a speed at which to control the electric motor. For the resistive mode, the configuration information may specify an amount of resistive force the electric motor is to apply to rotate radially-adjustable couplings during the pedaling session, a maximum pedal force that is desired for the user to exert on each pedal of the electromechanical device during the pedaling session, and/or a revolutions per minute threshold for the radially-adjustable couplings. For the active-assisted mode, the configuration information may specify a minimum pedal force and a maximum pedal force desired for the user to exert on each pedal of the electromechanical device, a speed at which to operate the electric motor for driving one or both of the radially-adjustable couplings, and so forth.

In some embodiments, responsive to receiving the configuration information, the processing device may determine that a trigger condition has occurred. The trigger condition may include receiving a selection of a mode from a user, an amount of time elapsing, receiving a command from the computing device executing the clinical portal, or the like. The processing device may control, based on the trigger condition occurring, the electric motor to operate in a resistive mode by providing, based on the trigger condition, a resistance to rotation of the pedals.

At block 404, the processing device may set a resistance parameter and a maximum pedal force parameter based on the amount of resistive force and the maximum pedal force, respectively, included in the configuration information for the pedaling session. The resistance parameter and the maximum force parameter may be stored in a memory device of the computing device and used to control the electric motor during the pedaling session. For example, the processing device may transmit a control signal along with the resistance parameter and/or the maximum pedal force parameter to the motor controller, and the motor controller may drive the electric motor using at least the resistance parameter during the pedaling session.

At block 406, the processing device may measure force applied to pedals of the electromechanical device as a user operates (e.g., pedals) the electromechanical device. The electric motor of the electromechanical device may provide resistance during the pedaling session based on the resistance parameter. A force sensor disposed in each pedal and operatively coupled to the motor controller and/or the computing device executing the user portal may measure the force exerted on each pedal throughout the pedaling session. The force sensors may transmit the measured force to a processing device of the pedals, which in turn may cause a communication device to transmit the measured force to the processing device of the motor controller and/or the computing device.

At block 408, the processing device may determine whether the measured force exceeds the maximum pedal force parameter. To make this determination, the processing device may compare the measured force to the maximum pedal force parameter.

At block 410, responsive to determining that the measured force exceeds the maximum pedal force parameter, the processing device may reduce the resistance parameter to maintain the revolutions per minute threshold specified in the configuration information so the electric motor applies less resistance during the pedaling session. Reducing the resistance may enable the user to pedal faster, thereby increasing the revolutions per minute of the radially-adjustable couplings. Maintaining the revolutions per minute threshold may ensure that the patient is exercising the affected body part as rigorously as desired during the mode. Responsive to determining that the measured force does not exceed the maximum pedal force parameter, the processing device may, during the pedaling session, maintain the same maximum pedal force parameter specified by the configuration information.

In some embodiments, the processing device may determine that a second trigger condition has occurred. The second trigger condition may include receiving a selection of a mode from a user via the user portal, an amount of time elapsing, receiving a command from the computing device executing the clinical portal, or the like. The processing device may control, based on the trigger condition occurring, the electric motor to operate in a passive mode by independently driving one or more radially-adjustable couplings coupled to the pedals in a rotational fashion. The electric motor may drive the one or more radially-adjustable couplings at a speed specified in the configuration information without another driving source. Also, the electric motor may drive each of the one or more radially-adjustable couplings individually at different speeds.

In some embodiments, the processing device may determine that a third trigger condition has occurred. The third trigger condition may be similar to the other trigger conditions described herein. The processing device may control, based on the third trigger condition occurring, the electric motor to operate in an active-assisted mode by measuring revolutions per minute of the one or more radially-adjustable couplings coupled to the pedals and, when the measured revolutions per minute satisfy a threshold condition, causing the electric motor to drive, in a rotational fashion, the one or more radially-adjustable couplings coupled to the pedals.

In some embodiments, the processing device may receive, from a goniometer worn by the user operating the electromechanical device, a set of angles of extension between an upper leg and a lower leg at a knee of the user. The set of angles is measured as the user extends the lower leg away from the upper leg via the knee. In some embodiments, the angles of extension may represent angles between extending a lower arm away from an upper arm at an elbow. Further, the processing device may receive, from the goniometer, a set of angles of bend between the upper leg and the lower leg at the knee of the user. The set of angles of bend is measured as the user retracts the lower leg closer to the upper leg via the knee. In some embodiments, the angles of bend represent angles between bending a lower arm closer to an upper arm at an elbow.

The processing device may determine whether a range of motion threshold condition is satisfied based on the set of angles of extension and the set of angles of bend. Responsive to determining that the range of motion threshold condition is satisfied, the processing device may modify a position of one of the pedals on one of the radially-adjustable couplings to change a diameter of a range of motion of the one of the pedals. Satisfying the range of motion threshold condition may indicate that the affected body part is strong enough or flexible enough to increase the range of motion allowed by the radially-adjustable couplings.

FIG. 5 illustrates example operations of a method 500 that uses a goniometer according to certain embodiments of this disclosure for measuring angles of bend and/or extension of a lower leg relative to an upper leg. In some embodiments, one or more operations of the method 500 are implemented in computer instructions executed by the processing devices of the goniometer 106 of FIG. 1. The method 500 may be performed in the same or a similar manner as described above in regards to method 300.

At block 502, the processing device may receive a set of angles from the one or more goniometers. The goniometer may measure angles of extension and/or bend between an upper body part (leg, arm, torso, neck, head, etc.) and a lower body part (leg, arm, torso, neck head, hand, feet, etc.) as the body parts are extended and/or bent during various sessions (e.g., pedaling session, walking session, extension session, bend session, etc.). The set of angles may be received while the user is pedaling one or more pedals of the electromechanical device.

At block 504, the processing device may transmit the set of angles to a computing device controlling the electromechanical device, via one or more network interface cards. The electromechanical device may be operated by a user rehabilitating an affected body part. For example, the user may have recently had surgery to repair a tear of an anterior cruciate ligament (ACL). Accordingly, the goniometer may be secured proximate to the knee by the affected ACL around the upper and lower leg.

In some embodiments, transmitting the set of angles to the computing device controlling the electromechanical device may cause the computing device, based on the set of angles satisfying a range of motion threshold condition to adjust a position of one of one or more pedals on a radially-adjustable coupling. The range of motion threshold condition may be set based on configuration information for a treatment plan received from the cloud-based computing system or the computing device executing the clinical portal. The position of the pedal is adjusted to increase a diameter of a range of motion transited by an upper body part (e.g., an upper leg), lower body part (e.g., a lower leg), and a joint (e.g., knee) of the user as the user operates the electromechanical device. In some embodiments, the position of the pedal may be adjusted in real-time while the user is operating the electromechanical device. In some embodiments, the user portal may present a notification to the user indicating that the position of the pedal should be modified, and the user may modify the position of the pedal and resume operating the electromechanical device with the modified pedal position.

In some embodiments, transmitting the set of angles to the computing device may cause the computing device executing the user portal to present the set of angles in a graphical animation of the lower body part and the upper body part moving in real-time during the extension or the bend. In some embodiments, the set of angles may be transmitted to the computing device executing the clinical portal, and the clinical portal may present the set of angles in a graphical animation of the lower body part and the upper body part moving in real-time during the extension or the bend. In addition, the set of angles may be presented in one or more graphs or charts on the clinical portal and/or the user portal to depict progress of the extension or bend for the user.

FIGS. 6-12 illustrate various detailed views of components of the rehabilitation system disclosed herein. The rehabilitation system can include additional and/or fewer components and is not limited to those illustrated in FIGS. 6-12.

Figure 6:
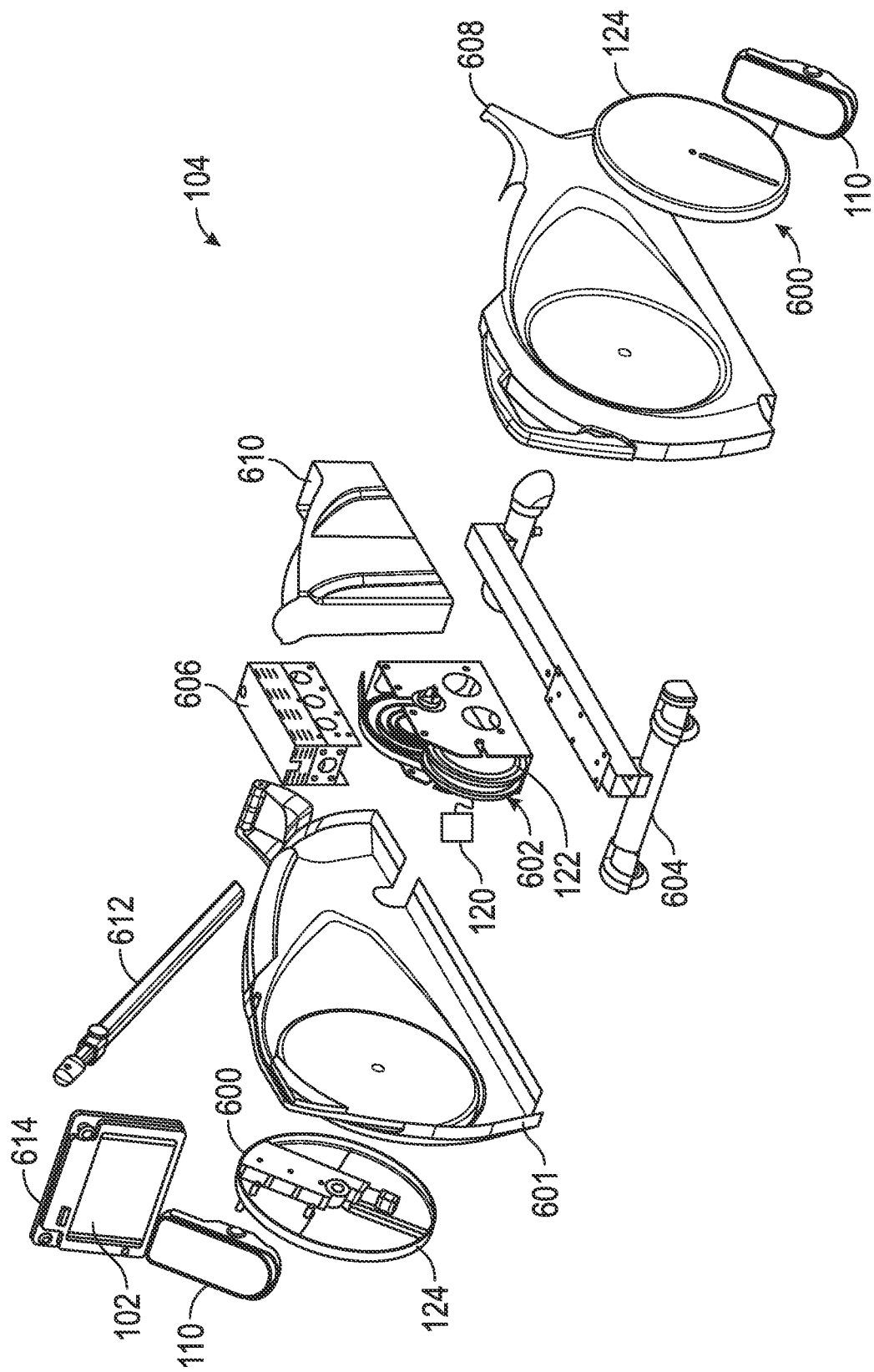
FIG. 6 illustrates an exploded view of components of the exercise and rehabilitation device according to certain embodiments of this disclosure.

For example, FIG. 6 illustrates an exploded view of components of the exercise and rehabilitation electromechanical device 104 according to certain embodiments of this disclosure. The electromechanical device 104 may include a pedal 110 that couples to a left radially-adjustable coupling 124 via a left pedal arm assembly 600 disposed within a cavity of the left radially-adjustable coupling 124. The radially-adjustable coupling 124 may be disposed in a circular opening of a left outer cover 601 and the pedal arm assembly 600 may be secured to a drive sub-assembly 602. The drive sub-assembly 602 may include the electric motor 122 operatively coupled to the motor controller 120. The drive sub-assembly 602 may include one or more braking mechanisms, such as disc brakes, that enable instantaneously locking of the electric motor 122 or stopping of the electric motor 122 over a period of time. The electric motor 122 may be any suitable electric motor (e.g., a crystallite electric motor). The drive sub-assembly 602 may be secured to a frame sub-assembly 604. A top support sub-assembly 606 may be secured on top of the drive sub-assembly 602.

A right pedal 110 couples to a right radially-adjustable coupling 124 via a right pedal arm assembly 600 disposed within a cavity of the right radially-adjustable coupling 124. The right radially-adjustable coupling 124 may be disposed in a circular opening of a right outer cover 608 and the right pedal arm assembly 600 may be secured to the drive sub-assembly 602. An internal volume may be defined when the left outer cover 601 and the right outer cover 608 are secured together around the frame sub-assembly 604. The left outer cover 601 and the right outer cover 608 may also make up the frame of the electromechanical device 104 when secured together. The drive sub-assembly 602, top support sub-assembly 606, and pedal arm assemblies 600 may be disposed within the internal volume upon assembly. A storage compartment 610 may be secured to the frame.

Further, a computing device arm assembly 612 may be secured to the frame and a computing device mount assembly 614 may be secured to an end of the computing device arm assembly 612. The computing device 102 may be attached or detached from the computing device mount assembly 614 as desired during operation of the electromechanical device 104.

Figure 7:
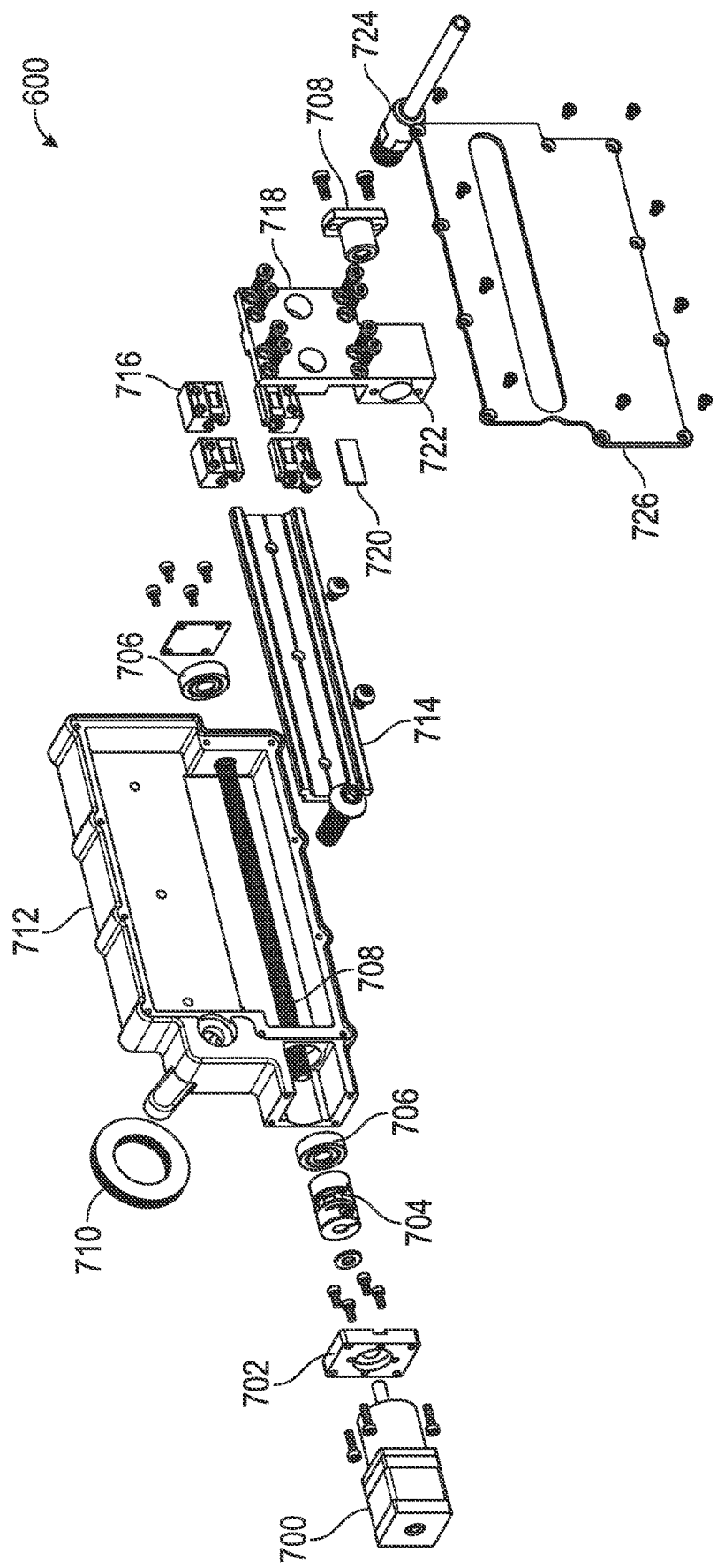
FIG. 7 illustrates an exploded view of a right pedal assembly according to certain embodiments of this disclosure.

FIG. 7 illustrates an exploded view of a pedal arm assembly 600 according to certain embodiments of this disclosure. The pedal arm assembly 600 includes a stepper motor 700. The stepper motor 700 may be any suitable stepper motor. The stepper motor 700 may include multiple coils organized in groups referred to as phases. Each phase may be energized in sequence to rotate the motor one step at a time. The control system may use the stepper motor 700 to move the position of the pedal on the radially-adjustable coupling.

The stepper motor 700 includes a barrel and pin inserted through a hole in a motor mount 702. A shaft coupler 704 and a bearing 706 include through holes that receive an end of a first end lead screw 708. The lead screw 708 is disposed in a lower cavity of a pedal arm 712. The pin of the electric motor may be inserted in the through holes of the shaft coupler 704 and the bearing 706 to secure to the first end of the lead screw 708. The motor mount 702 may be secured to a frame of the pedal arm 712. Another bearing 706 may be disposed on another end of the lead screw 708. An electric slip ring 710 may be disposed on the pedal arm 712.

A linear rail 714 is disposed in and secured to an upper cavity of the pedal arm 712. The linear rail 714 may be used to move the pedal to different positions as described further below. A number of linear bearing blocks 716 are disposed onto a top rib and a bottom rib of the linear rail 714 such that the bearing blocks 716 can slide on the ribs. A spindle carriage 718 is secured to each of the bearing blocks 716. A support bearing 720 is used to provide support. The lead screw 708 may be inserted in through hole 722 of the spindle carriage 718. A spindle 724 may be secured at an end of the through hole 722 to house an end of the lead screw 708. A spindle 724 may be attached to a hole of the spindle carriage 718. When the pedal arm assembly 600 is assembled, the end of the spindle 724 may protrude through a hole of a pedal arm cover 726. When the stepper motor 700 turns on, the lead screw 708 can be rotated, thereby causing the spindle carriage 718 to move radially along the linear rail 714. As a result, the spindle 724 may radially traverse the opening of the pedal arm cover 726 as desired.

Figure 8:
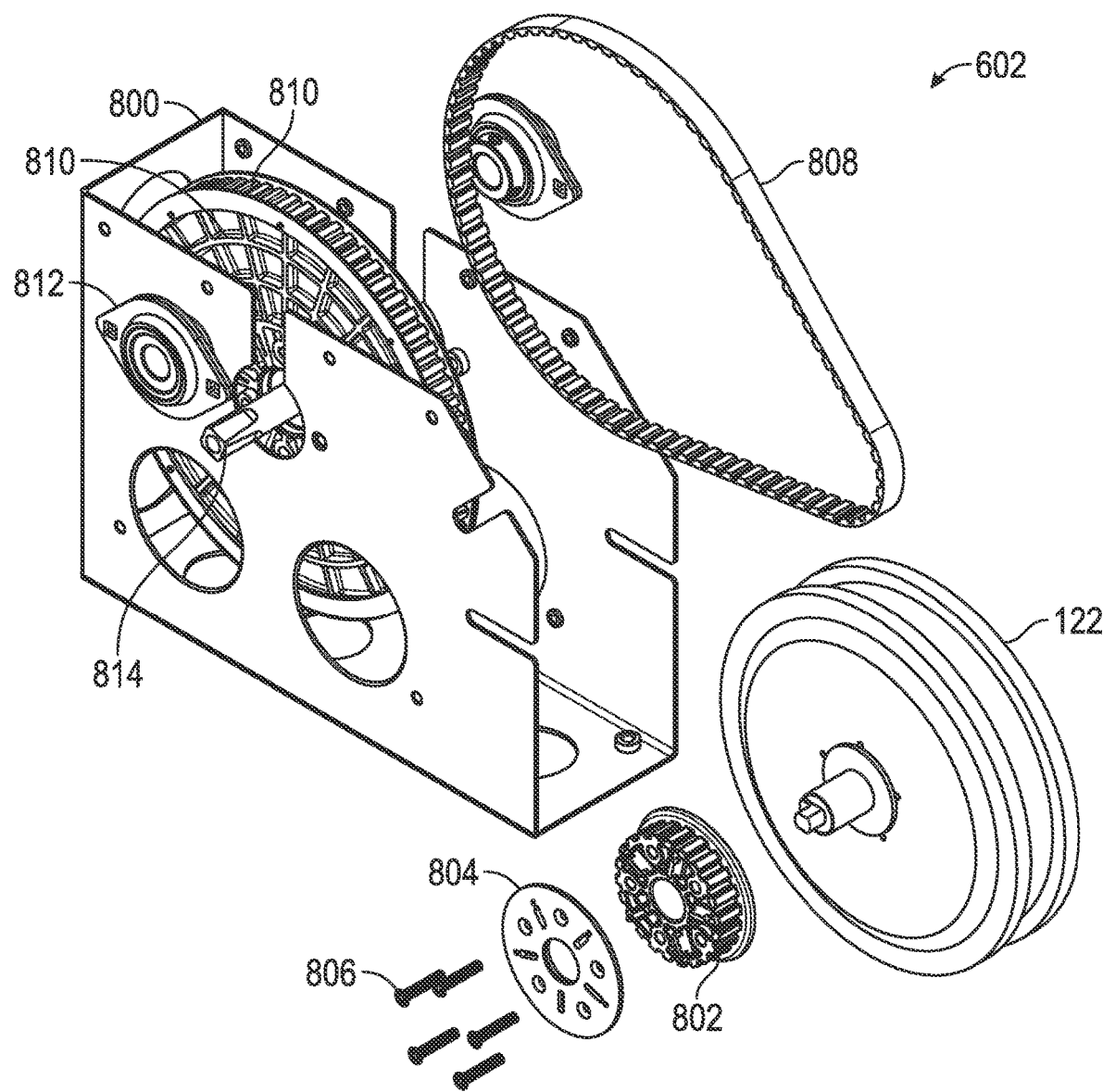
FIG. 8 illustrates an exploded view of a motor drive assembly according to certain embodiments of this disclosure.

FIG. 8 illustrates an exploded view of a drive sub-assembly 602 according to certain embodiments of this disclosure. The drive sub-assembly 602 includes an electric motor 122. The electric motor 122 is partially disposed in a crank bracket housing 800. A side of the electric motor 122 includes a small molded pulley 802 secured to it via a small pulley plate 804 by screws 806. Also disposed within the crank bracket housing 800 is a timing belt 808 and a large molded pulley 810. The timing belt 808 may include teeth on an interior side that engage with teeth on the small molded pulley 802 and the large molded pulley 810 to cause the large molded pulley 810 to rotate when the electric motor 122 operates. The crank bracket housing 800 includes mounted bearing 812 on both sides through which crankshafts 814 of the large molded pulley 810 protrude. The crankshafts 814 may be operatively coupled to the pedal assemblies.

Figure 9:
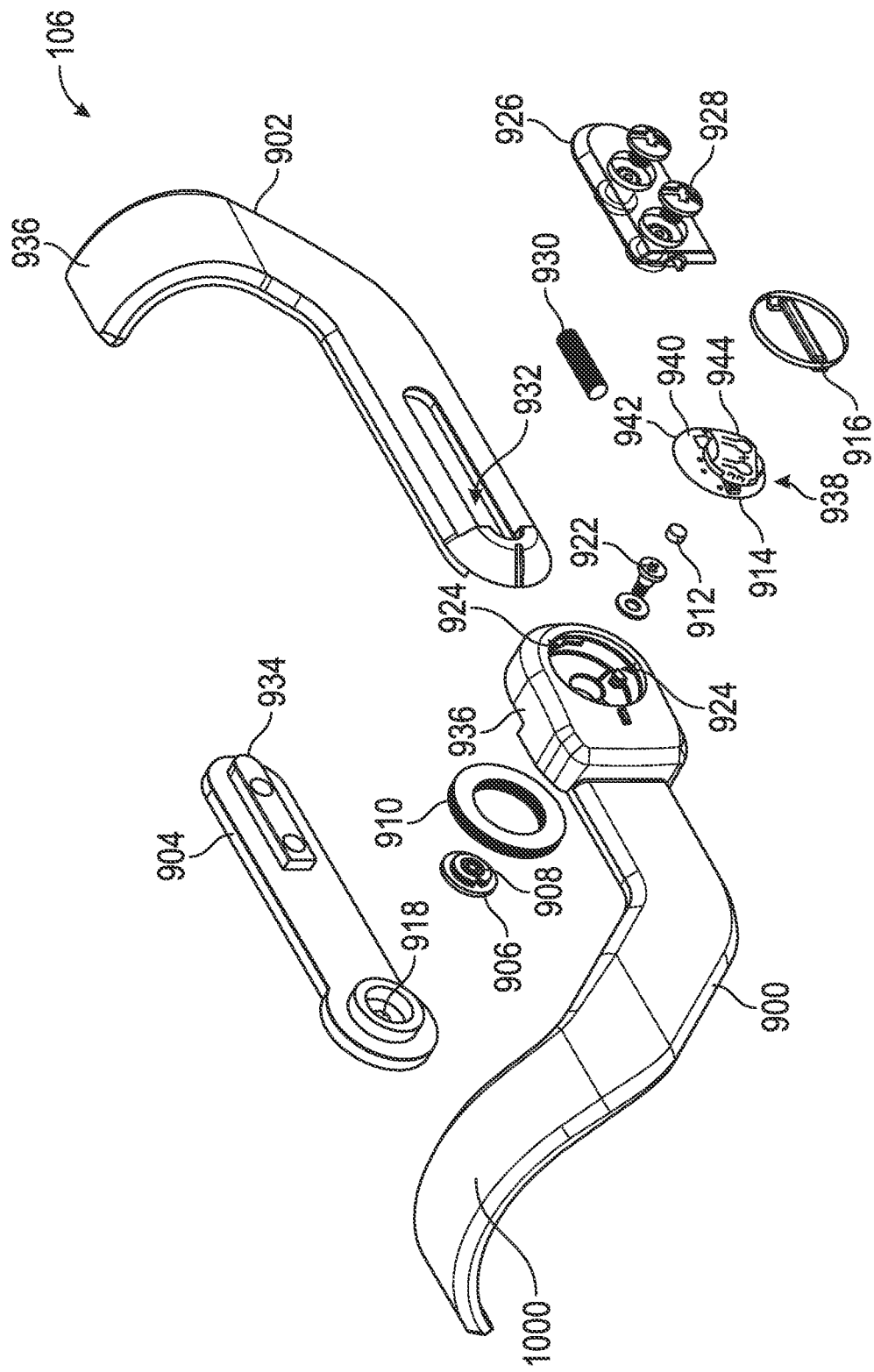
FIG. 9 illustrates an exploded view of a portion of a goniometer according to certain embodiments of this disclosure.

FIG. 9 illustrates an exploded view of a portion of a goniometer 106 according to certain embodiments of this disclosure. The goniometer 106 includes an upper section 900 and a lower section 902. The upper section 900 and the lower section 902 are rotatably coupled via a lower leg side brace 904. A bottom cap 906 may be inserted into a protruded cavity 918 of the lower leg side brace 904. In some embodiments, the bottom cap 906 includes a microcontroller 908. A thrust roller bearing 910 fits over the protruded cavity 918 of the lower leg side brace 904, which is inserted into a cavity 920 of the upper section 900 and secured to the upper section 900 via an attachment, such as a screw 922. Second cavity 924 is located is on a side of the upper section 900 opposite to the side having the cavity 920 with the inserted protruded cavity 918. A radial magnet 912 and a microcontroller (e.g., a printed control board) 914 are disposed in the second cavity 924 and a top cap 916 is placed on top to cover the second cavity 924. The microcontroller 908 and/or the microcontroller 914 may include a network interface card 940 or a radio configured to communicate via a short range wireless protocol (e.g., Bluetooth), a processing device 944, and a memory device 938. Further, either or both of the microcontrollers 908 and 914 may include a magnetic sensing encoder chip that senses the position of the radial magnet 912. The position of the radial magnet 912 may be used to determine an angle of bend or extension 2118, 2218 of the goniometer 106 by the processing device(s) of the microcontrollers 908 and/or 914. The angles of bend/extension 2118, 2218 may be transmitted via the radio to the computing device 102. The lower section 902 defines an opening 932 configured to receive a protruding tab 934 and a spring 930. The spring 930 may be disposed along the opening 932 between the protruding tab 934 and a side cap 926. The side cap 926 may be coupled to the protruding tab 934 through the opening 932. One or more attachments 928 may couple the side cap 926 to the protruding tab 934. The attachment 928 may be a screw, a magnet, or any other desired attachment. The spring 930 can be configured to apply pressure on the side cap 926 to provide limited movement of the side cap 926 relative to the opening 932. The spring 930 may allow for movement of the lower section 902 relative to the upper section 900. The electronic device 106 can include additional and/or fewer components, including in different locations and/or configurations, and is not limited to those illustrated in FIG. 9.

Figure 10:
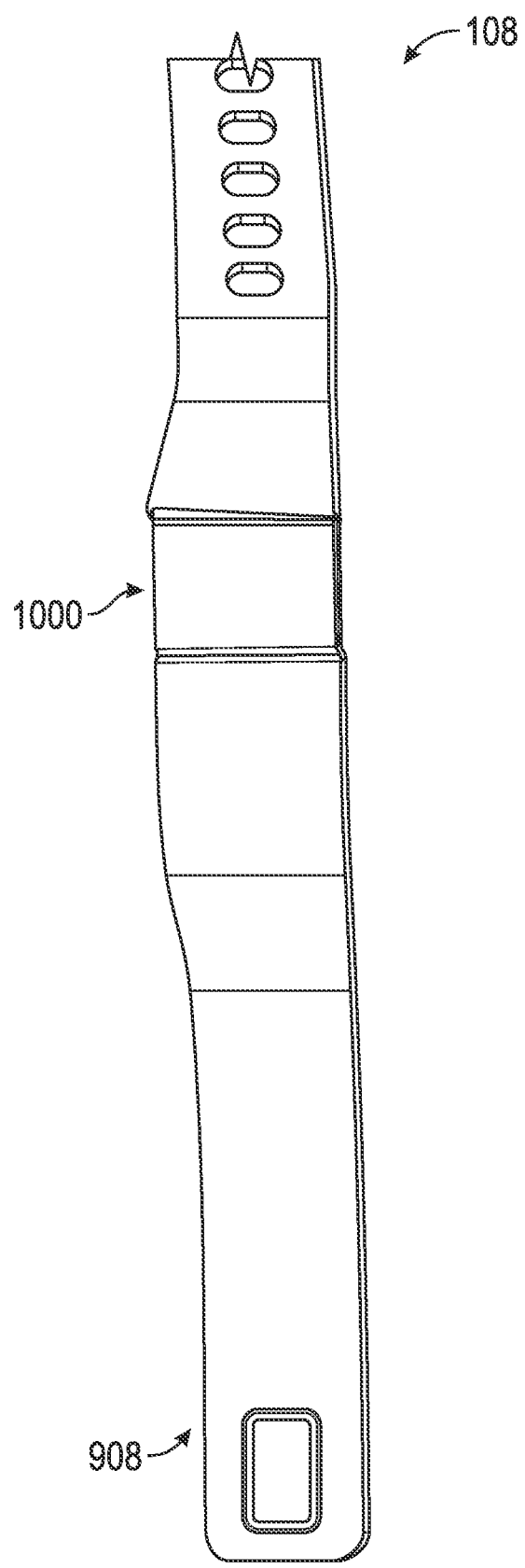
FIG. 10 illustrates a top view of a wristband according to certain embodiments of this disclosure.

FIG. 10 illustrates a top view of a wristband 108 according to certain embodiments of this disclosure. The wristband 108 includes a strap with a clasp to secure the strap to a wrist of a person. The wristband 108 may include one or more processing devices, memory devices, network interface cards, and so forth. The wristband 108 may include a display 1000 configured to present information measured by the wristband 108. The wristband 108 may include an accelerometer, gyroscope, and/or an altimeter, as discussed above. The wristband 108 may also include a light sensor to detect a heartrate of the user wearing the wristband 108. In some embodiments, the wristband 108 may include a pulse oximeter to measure an amount of oxygen (oxygen saturation) in the blood by sending infrared light into capillaries and measuring how much light is reflected off the gases. The wristband 108 may transmit the measurement data to the computing device 102.

Figure 11:
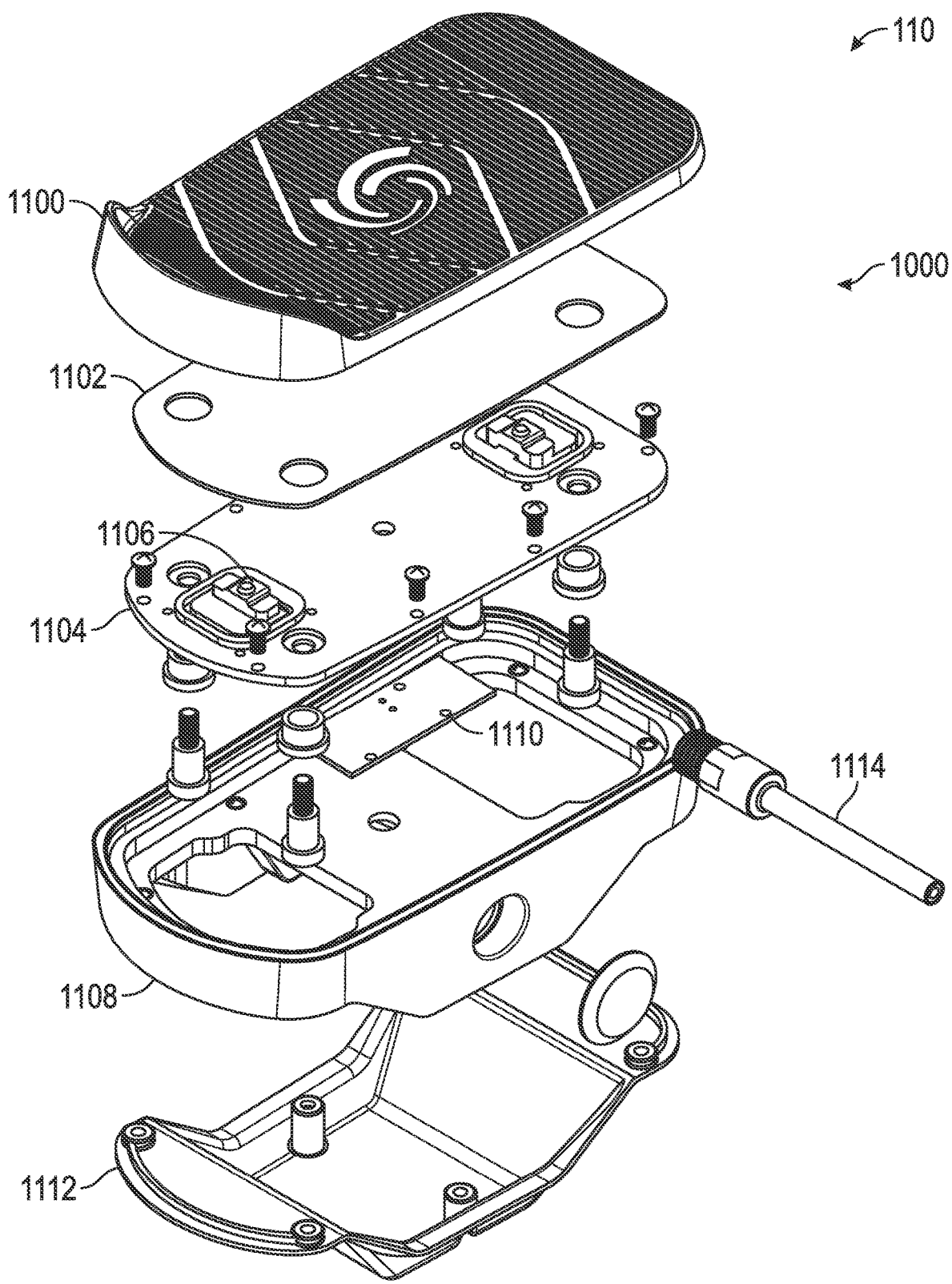
FIG. 11 illustrates an exploded view of a pedal according to certain embodiments of this disclosure.

FIG. 11 illustrates an exploded view of a pedal 110 according to certain embodiments of this disclosure. The pedal 110 includes a molded pedal top 1100 disposed on top of a molded pedal top support plate 1102. The molded pedal top 1100 and the molded pedal top support plate 1102 are secured to a molded pedal base plate 1104 via screws, for example. The molded pedal base plate 1104 includes a strain gauge 1106 configured to measure force exerted on the pedal 110. The pedal 110 also includes a molded pedal bottom 1108 where a microcontroller 1110 is disposed. The microcontroller 1110 may include processing devices, memory devices, and/or a network interface card or radio configured to communicate via a short range communication protocol, such as Bluetooth. The strain gauge 1106 is operatively coupled to the microcontroller 1110 and the strain gauge 1106 transmits the measured force to the microcontroller 1110. The microcontroller 1110 transmits the measured force to the computing device 102 and/or the motor controller 120 of the electromechanical device 104. The molded pedal top 1100, the molded pedal top support plate 1102, and the molded pedal base plate 1104 are secured to the molded pedal bottom 1108, which is further secured to a molded pedal bottom cover 1112. The pedal 110 also includes a spindle 1114 that couples with the pedal arm assembly.

Figure 12:
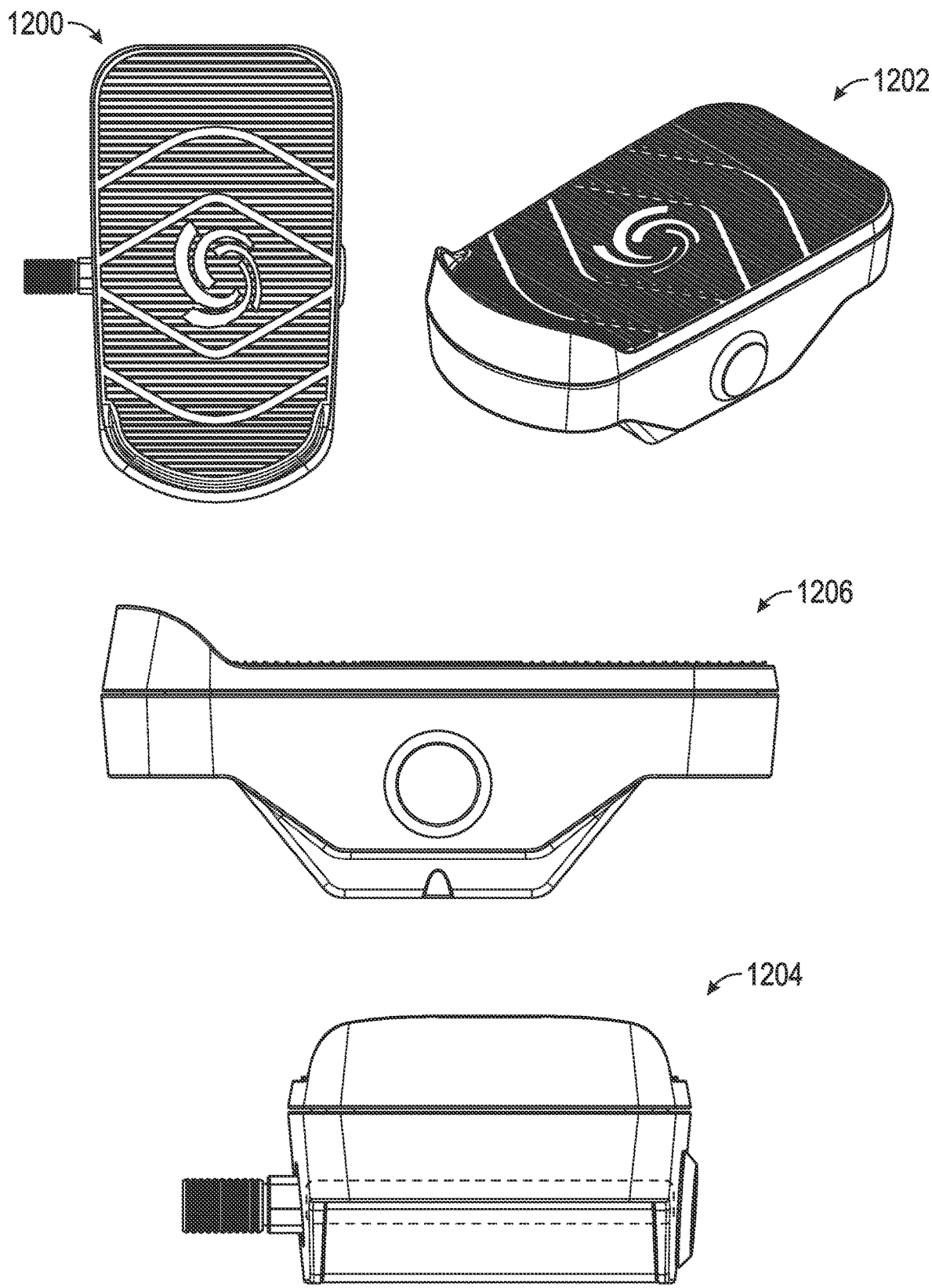
FIG. 12 illustrates additional views of the pedal according to certain embodiments of this disclosure.

FIG. 12 illustrates additional views of the pedal 110 according to certain embodiments of this disclosure. A top view 1200 of the pedal 110 is depicted, a perspective view 1202 of the pedal 110 is depicted, a front view 1204 of the pedal 110 is depicted, and a side view 1206 of the pedal 110 is depicted.

FIGS. 13-29 illustrate different user interfaces of the user portal 118. A user may use the computing device 102, such as a tablet, to execute the user portal 118. In some embodiments, as they perform a pedaling session, the user may hold the tablet in their hands and view the user portal 118. Various user interfaces of the user portal 118 may provide prompts for the users to affirm that they are wearing the goniometer and the wristband, and that their feet are on the pedals.

Figure 13:
FIG. 13 illustrates an example user interface of the user portal, and the user interface is configured to present a treatment plan for a user according to certain embodiments of this disclosure.

FIG. 13 illustrates an example user interface 1300 of the user portal 118, the user interface 1300 presenting a treatment plan 1302 for a user according to certain embodiments of this disclosure. The treatment plan 1302 may be received from the computing device 114 executing the clinical portal 126 and/or downloaded from the cloud-based computing system 116. The physician may have generated the treatment plan 1302 using the clinical portal 126 or the trained machine learning model(s) 132 may have generated the treatment plan 1302 for the user. As depicted, the treatment plan 1302 presents the type of procedure ("right knee replacement") that the patient underwent. Further, the treatment plan 1302 presents a pedaling session including a combination of the modes in which to operate the electromechanical device 104, as well as a respective set period of time for operating each of the modes. For example, the treatment plan 1302 indicates operating the electromechanical device 104 in a passive mode 1304 for 5 minutes, an active-assisted mode 1306 for 5 minutes, an active mode 1308 for 5 minutes, a resistive mode 1310 for 2 minutes, the active mode 1308 again for 3 minutes, and the passive mode 1304 for 2 minutes. The total duration of the pedaling session is 22 minutes and the treatment plan 1302 also specifies that the position of the pedal may be set according to a comfort level of the patient or user. The user interface 1300 also may display the number of sessions scheduled per day and how many sessions have been completed. Prior to the user beginning the pedaling session, the user interface 1300 may be displayed as an introductory user interface.

Figure 14:
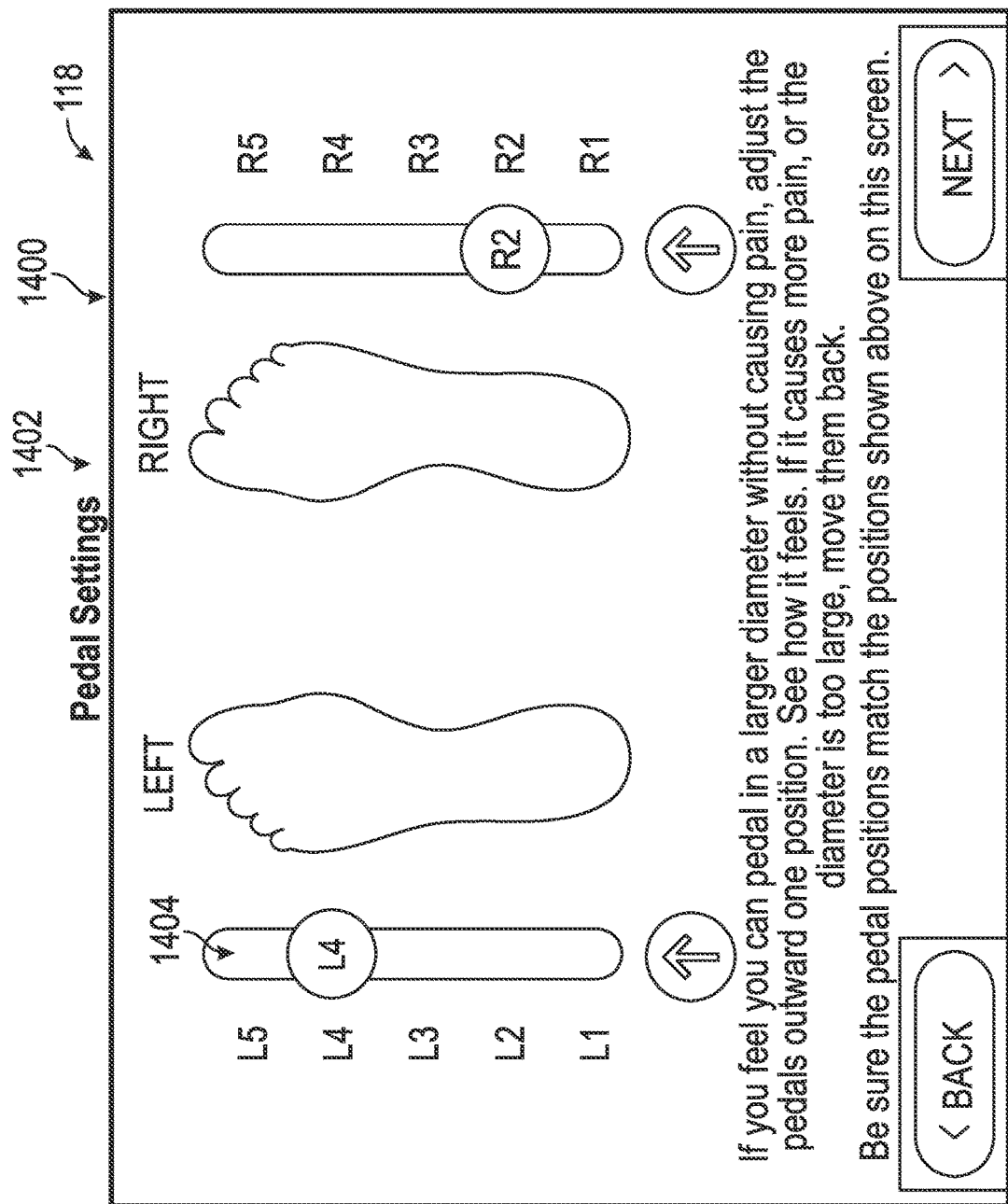
FIG. 14 illustrates an example user interface of the user portal, and the user interface is configured to present pedal settings for a user according to certain embodiments of this disclosure.

FIG. 14 illustrates an example user interface 1400 of the user portal 118, the user interface 1400 presenting pedal settings 1402 for a user according to certain embodiments of this disclosure. As depicted, graphical representation of feet are presented on the user interface 1400, as are two sliders including positions which correspond to portions of the feet. For example, a left slider 1404 includes positions L1, L2, L3, L4, and L5. A right slider includes positions R1, R2, R3, R4, and R5. A button 1404 may be slid up or down on the sliders to automatically adjust via the pedal arm assembly the pedal position on the radially-adjustable coupling. The pedal positions may be automatically populated according to the treatment plan but the user has the option to modify them based on comfort level. The changed positions may be stored locally on the computing device 102, sent to the computing device 114 executing the clinical portal 126, and/or sent to the cloud-based computing system 116.

Figure 15:
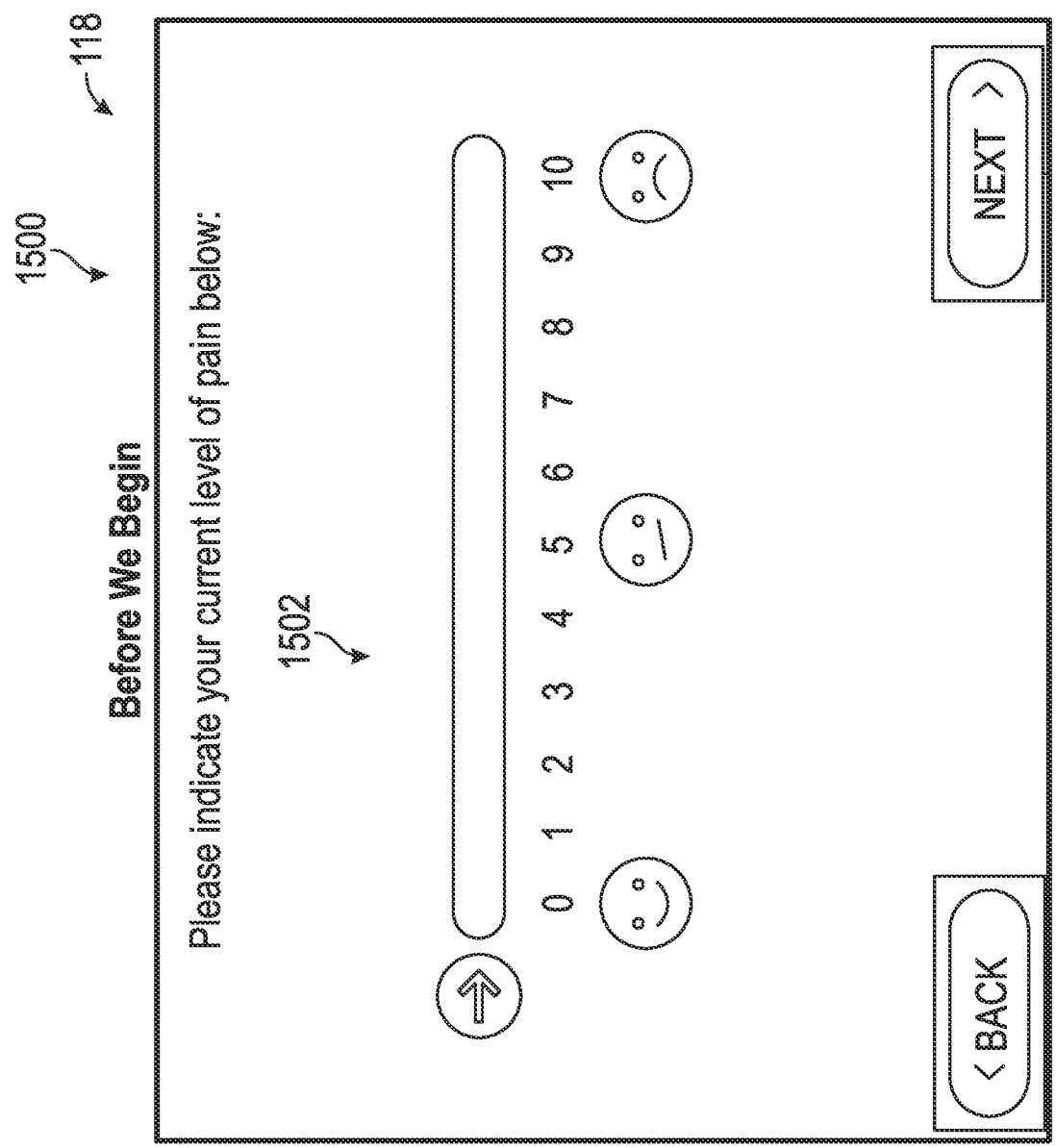
FIG. 15 illustrates an example user interface of the user portal, and the user interface is configured to present a scale for measuring pain of the user at a beginning of a pedaling session according to certain embodiments of this disclosure.

FIG. 15 illustrates an example user interface 1500 of the user portal 118, the user interface 1500 presenting a scale 1502 for measuring discomfort of the user at a beginning of a pedaling session according to certain embodiments of this disclosure. The scale 1502 may provide options ranging from no discomfort (e.g., smiley face), to mild discomfort (e.g., moderate face), to high discomfort (e.g., sad face). This discomfort information may be stored locally on the computing device 102, sent to the computing device 114 executing the clinical portal 126, and/or sent to the cloud-based computing system 116. For example, the user interface 1500 may be configured to receive a user input 1504, such as a pain score, from the user. The user input 1504 (e.g., a first user input) may be provided at or near the beginning of the rehabilitation session, or at any other desired time.

Figure 16:
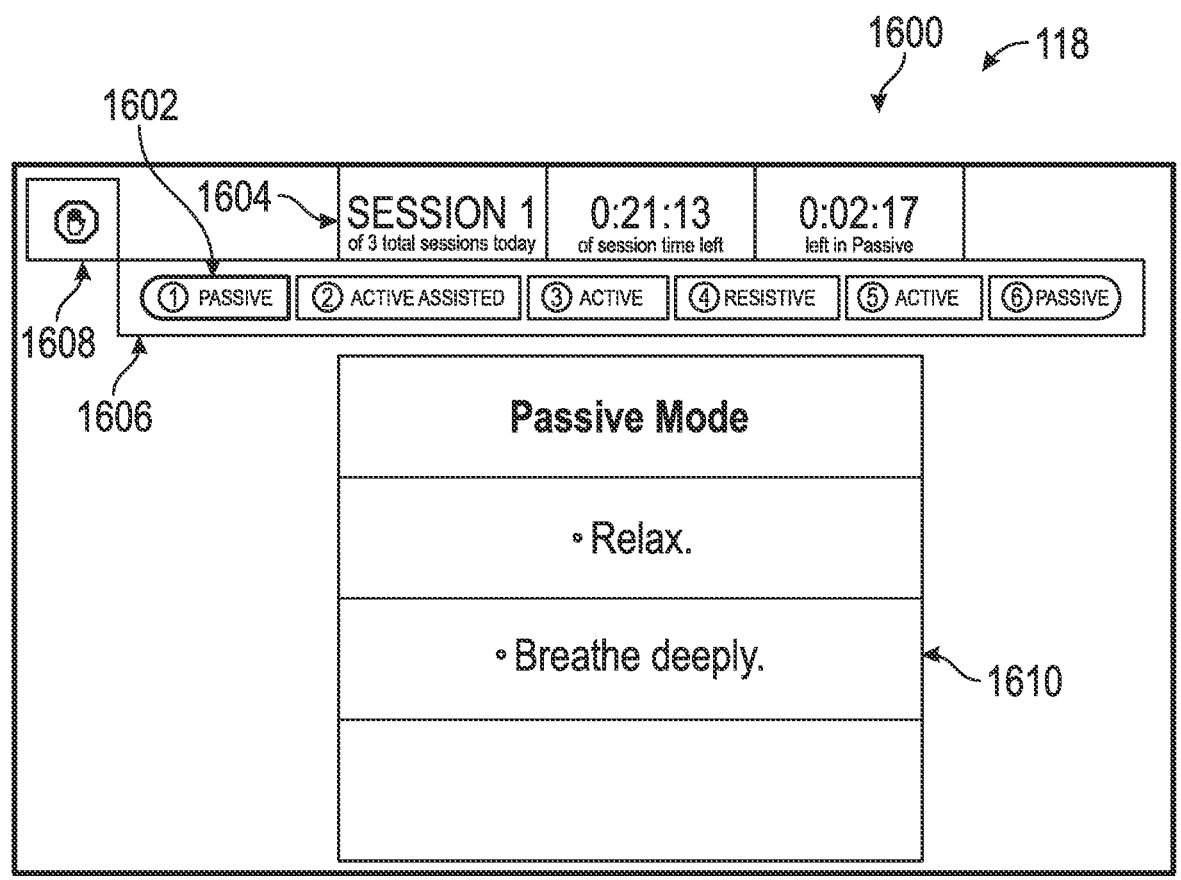
FIG. 16 illustrates an example user interface of the user portal, and the user interface is configured to present that the electromechanical device is operating in a passive mode according to certain embodiments of this disclosure.

FIG. 16 illustrates an example user interface 1600 of the user portal 118, the user interface is configured to present that the electromechanical device 104 is operating in a passive mode 1602 according to certain embodiments of this disclosure. The user interface 1600 is configured to present which pedaling session 1604 (session 1) is being performed and how many other pedaling sessions are scheduled for the day. The user interface 1600 also is configured to present an amount of time left in the pedaling session 1604 and an amount of time left in the current mode (passive mode). The full lineup of modes in the pedaling session 1604 is displayed in box 1606. While in the passive mode, the computing device controls the electric motor to independently drive the radially-adjustable couplings so the user does not have to exert any force on the pedals but such that their affected body part(s) and/or muscle(s) are enabled to be stretched and warmed up. At any time, if the user so desires, the user may select a stop button 1608, which may cause the electric motor to lock and stop the rotation of the radially-adjustable couplings instantaneously or over a set period of time. A descriptive box 1610 may provide instructions related to the current mode to the user.

FIGS. 17A-D illustrate an example user interface 1700 of the user portal 118, the user interface 1700 is configured to present that the electromechanical device 104 is operating in active-assisted mode 1702 and the user is applying various amounts of force to the pedals according to certain embodiments of this disclosure. Graphical representations 1704 of feet are configured to be presented on the user interface 1700 and the graphical representations may be configured to display the amount of force measured at the pedals. The force sensors (e.g., strain gauge) in the pedal may measure the forces exerted by the user and the microcontroller of the pedal may transmit the force measurements to the computing device 102. Notifications may be configured to be presented when the amount of force is outside of a force threshold 1730 (e.g., either below a range of force threshold 1730 or above the range of force threshold 1730). For example, in FIG. 17A, the right foot includes a notification to apply more force with the right foot because the current force measured at the pedal 110 is below the force threshold 1730.

A virtual tachometer 1706 is also presented that measures the revolutions per time period (e.g., per minute) of the radially-adjustable couplings and displays the current speed at which the user is pedaling. For example, the tachometer 1706 includes areas 1708 (between 0 and 10 revolutions per minute and between 20 and 30 revolutions per minute) that the user should avoid according to their treatment plan. In the depicted example, the treatment plan specifies that the user should maintain the speed at between 10 and 20 revolutions per minute. The electromechanical device 104 transmits the speed to the computing device 102 and the needle 1710 moves in real-time as the user operates the pedals. Notifications are presented near the tachometer 1706, wherein such notifications may indicate that the user should keep the speed above a certain revolutions threshold 1732 (e.g., 10 RPM). If the computing device 102 receives a speed from the electromechanical device 104 and the speed is below the revolutions threshold 1732, the computing device 102 may control the electric motor to drive the radially-adjustable couplings to maintain the revolutions threshold 1732. The computing device 102 may also be made capable of determining the state of the user in a particular exercise comprising the treatment plan, such that if the state is to maintain the revolutions per minute, the notification will be issued, but further, such that if the state is indicative of starting to exercise, ending an exercise, or transitioning between different parts of an exercise, and crossing an otherwise undesirable or forbidden threshold and/or range of revolutions per minute would, in these particular or otherwise similar indictive states, be neither undesirable nor forbidden, and the computing device 102 would, in those instances, not issue a notification. As will readily be appreciated by a person of ordinary skill of the art in light of having read the present disclosure, as used herein, actions described as being performed in real-time include actions performed in near-real-time without departing from the scope and intent of the present disclosure.

Figure 17A:
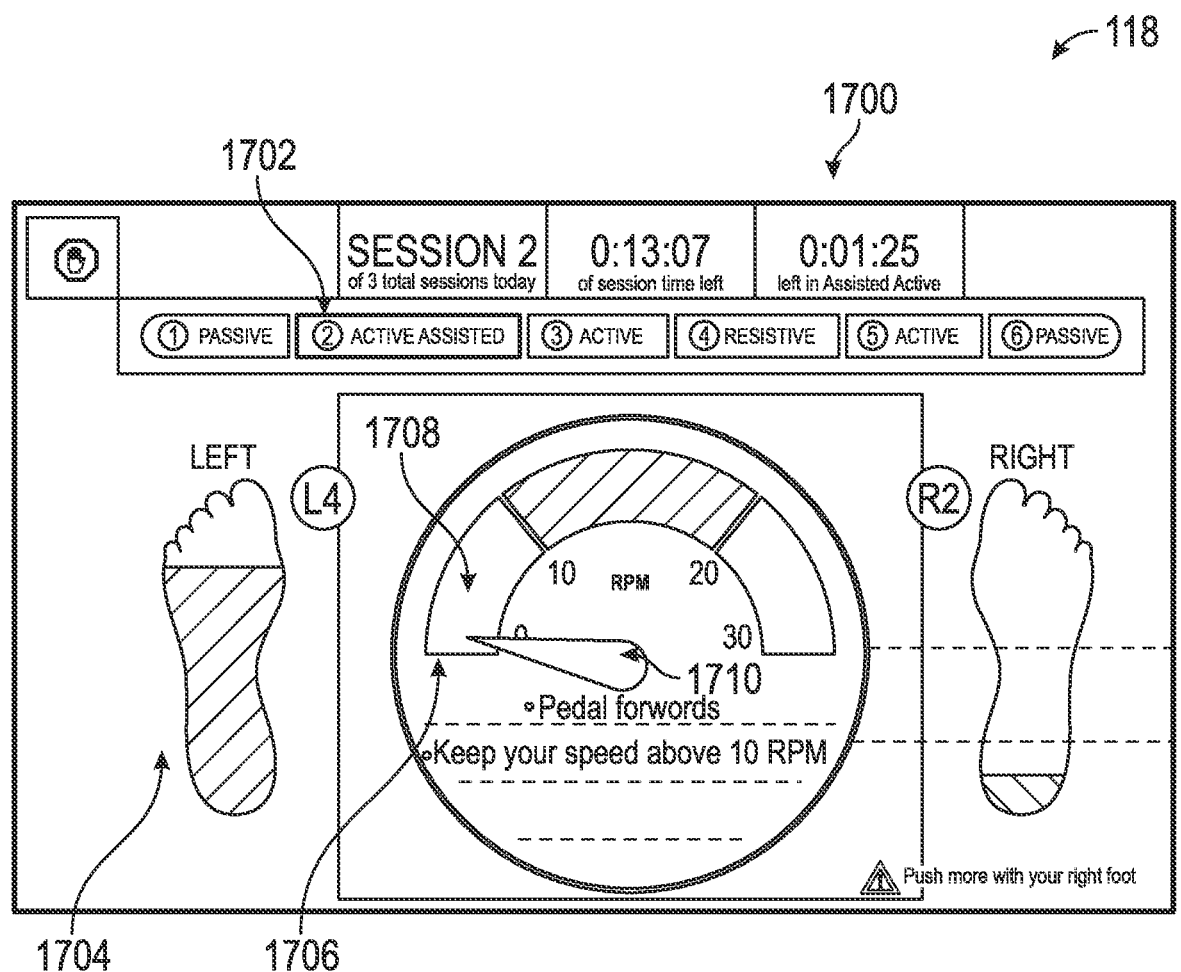
FIGS. 17A-D illustrate an example user interface of the user portal, and the user interface is configured to present that the electromechanical device is operating in active-assisted mode and if and/or to what extent the user is applying various amounts of force to the pedals according to certain embodiments of this disclosure.
Figure 17B:
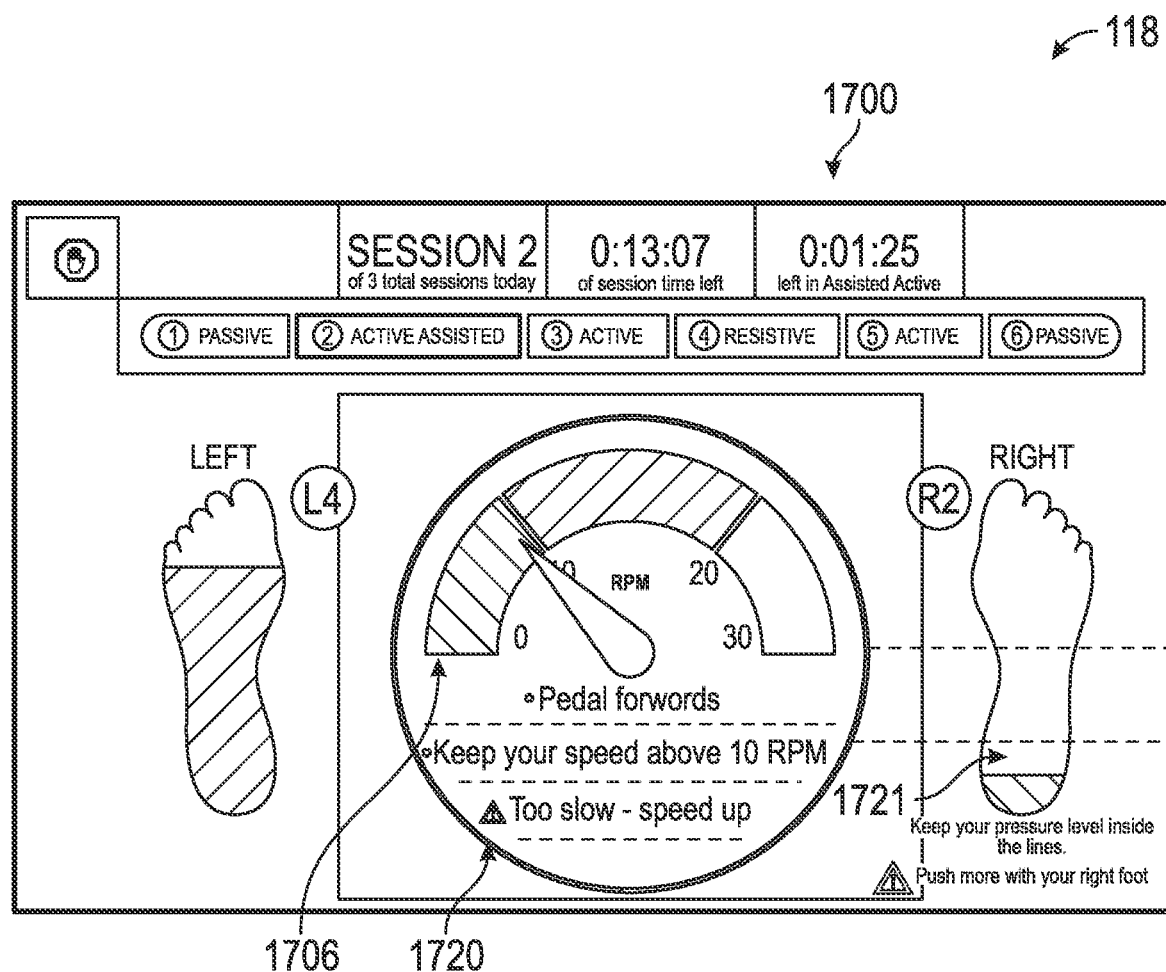
Figure 17C:
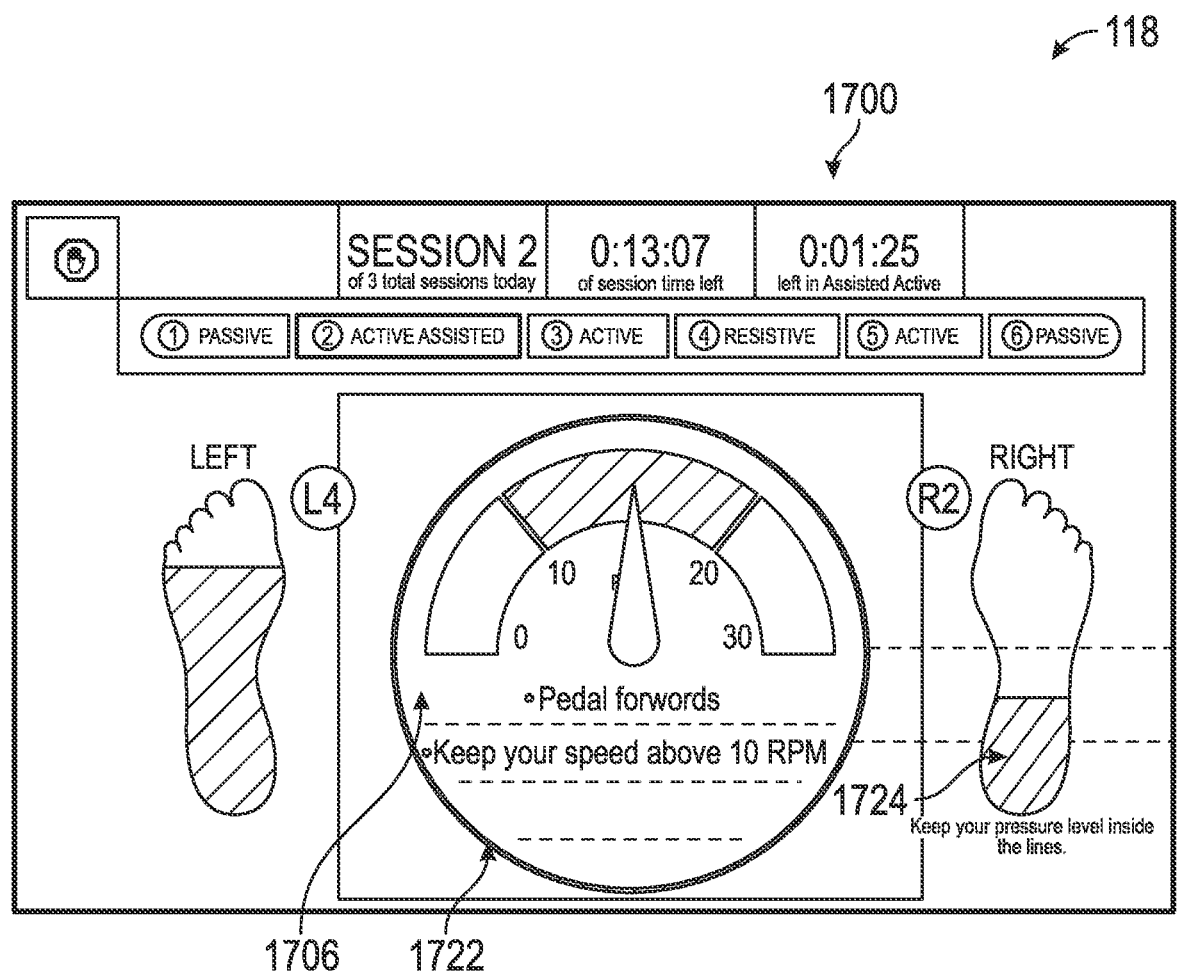
Figure 17D:
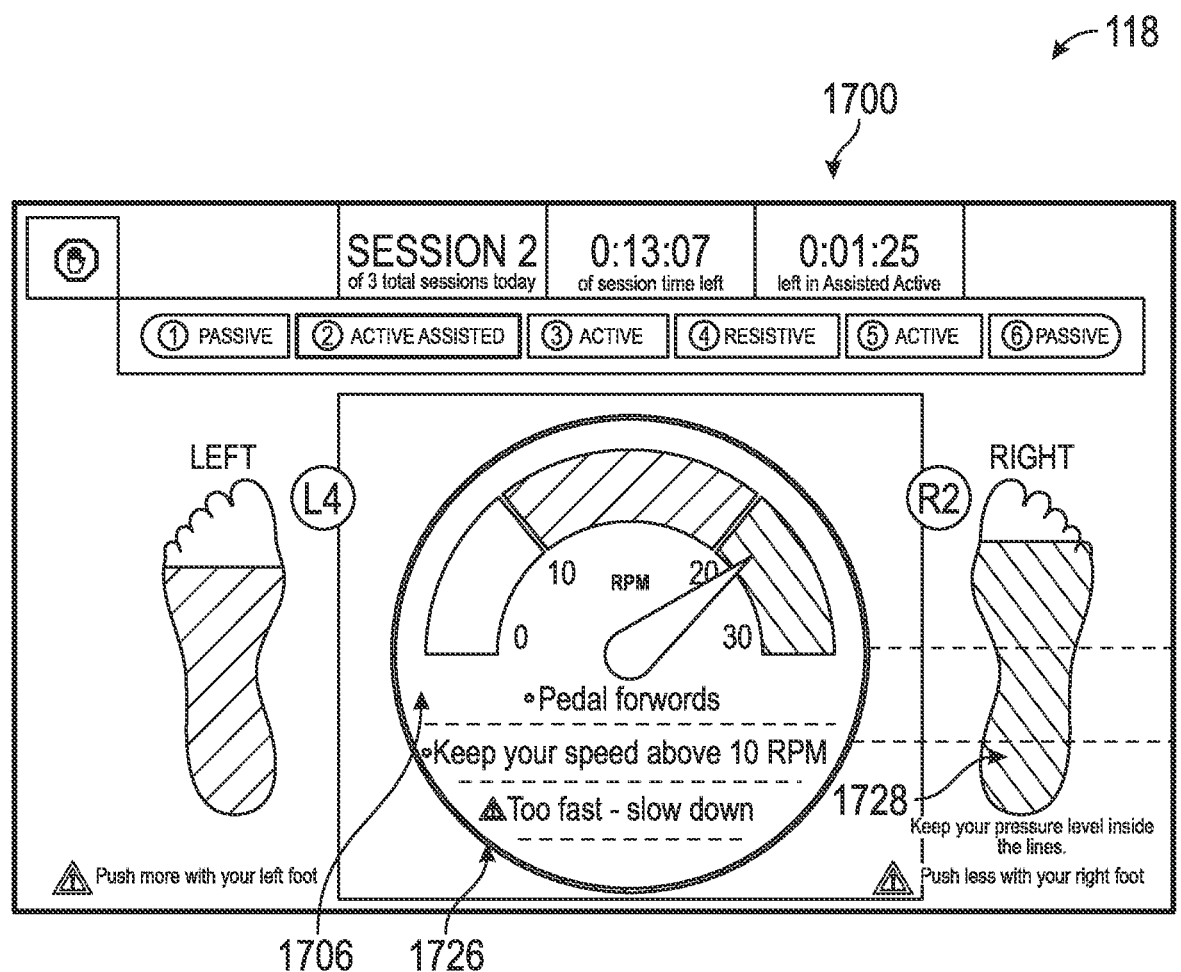

FIG. 17B depicts the example user interface 1700 presenting a graphic 1720 for the tachometer 1706 when the speed is below the revolutions threshold 1732. As depicted, a notification is presented that states "Too slow—speed up." Also, when the pressure exerted at the pedal is below the range of force threshold 1730, the user interface 1700 presents an example graphical representation 1721 of the right foot. A notification may be presented that states, "Push more with your right foot." FIG. 17C depicts, when the speed is within the desired target revolutions per minute, the example user interface 1700 presenting a graphic 1722 for the tachometer 1706. Also, the user interface 1700 presents, when the pressure exerted at the pedal is within the range of force threshold 1730, an example graphical representation 1724 of the right foot. FIG. 17D depicts, when the speed is above the desired target revolutions per minute, the example user interface 1700 presenting a graphic 1726 for the tachometer 1706. As depicted, a notification is presented that states "Too fast—slow down." Also, the user interface 1700 presents, when the pressure exerted at the pedal is above the range of force threshold 1730, an example graphical representation 1728 of the right foot. A notification may be presented that states "Push less with your right foot."

Figure 18:
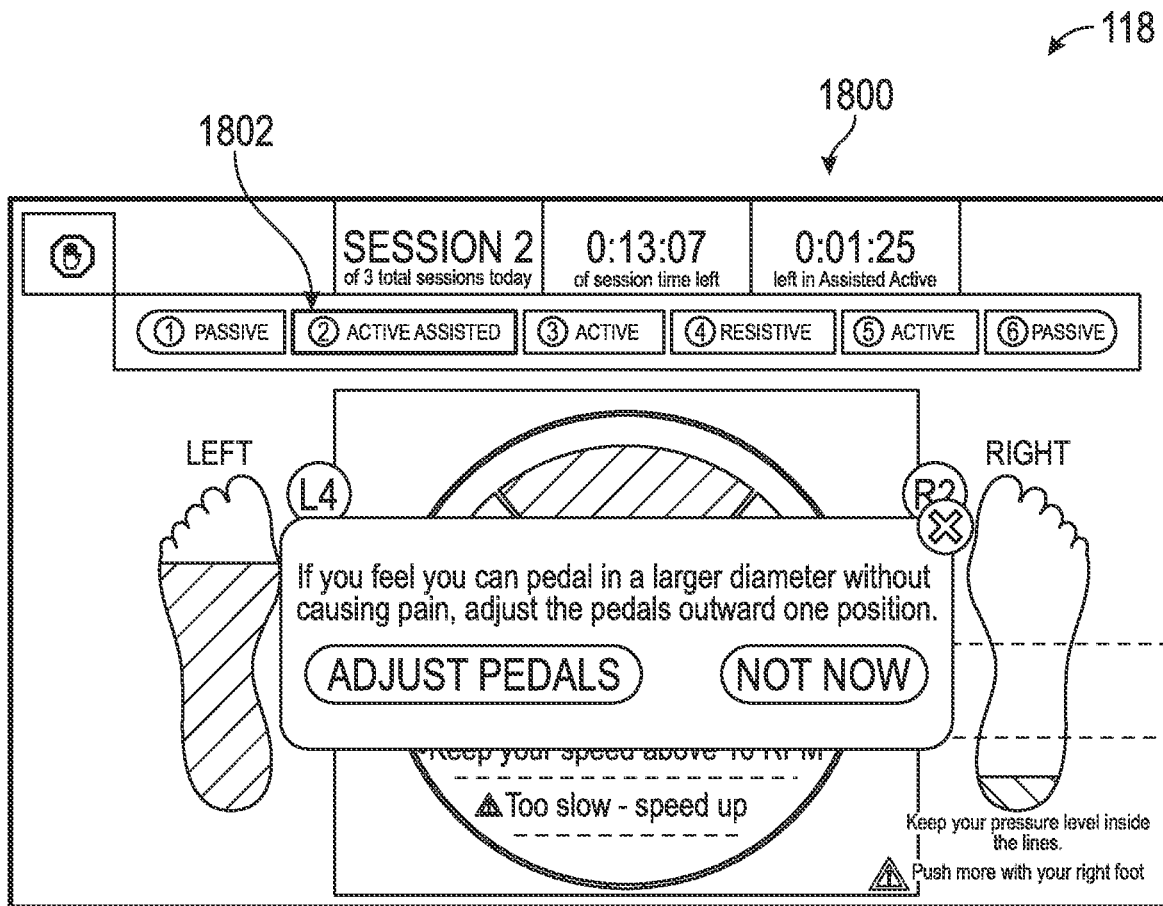
FIG. 18 illustrates an example user interface of the user portal, and the user interface is configured to present a request to modify pedal position while the electromechanical device is operating in active-assisted mode according to certain embodiments of this disclosure.

FIG. 18 illustrates an example user interface 1800 of the user portal 118, the user interface 1800 presenting a request 1804 to modify pedal position while the electromechanical device 104 is operating in active-assisted mode 1802 according to certain embodiments of this disclosure. The request 1804 may graphically pop up on a regular interval if specified in the treatment plan. If the user selects the "Adjust Pedals" button 1806, the user portal 118 may present a screen that allows the user to modify the position of the pedals.

Figure 19:
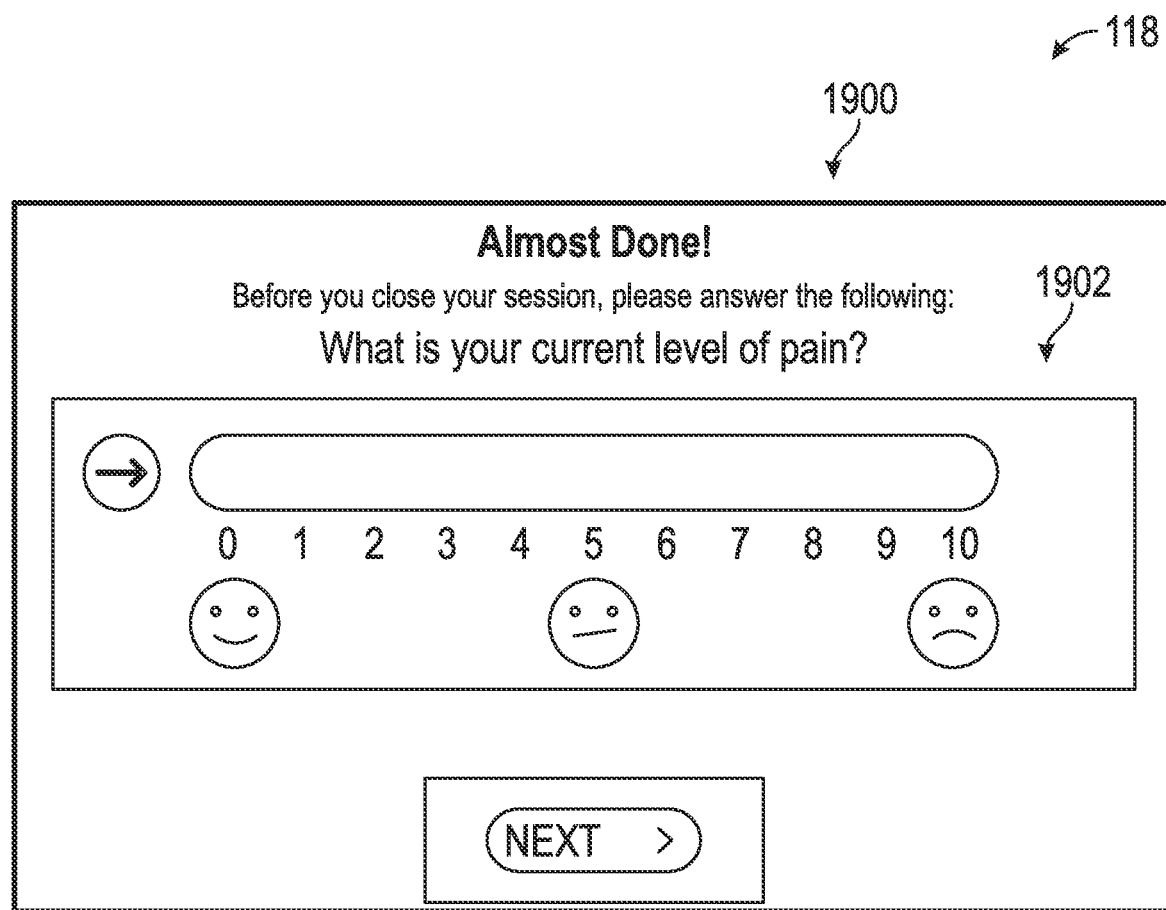
FIG. 19 illustrates an example user interface of the user portal, and the user interface is configured to present a scale for measuring pain of the user at an end of a pedaling session according to certain embodiments of this disclosure.

FIG. 19 illustrates an example user interface 1900 of the user portal 118, the user interface 1900 presenting a scale 1902 for measuring discomfort of the user at an end of a pedaling session according to certain embodiments of this disclosure. The pain level may be obtained from the user in response to a solicitation, such as a question, presented upon the user interface 1900. The scale 1902 may provide choices, such as a pain level, ranging from no discomfort (e.g., smiley face), to mild discomfort (e.g., moderate face), to high discomfort (e.g., sad face); alternatively a non-illustrated version of the scale could be alphabetic (A-to-F), numeric (1-to-10), or in any other form enabling an indication of comfort to be made. As used herein, "discomfort" is simply an approximate opposite of "comfort," and hence "no discomfort" corresponds approximately to "high comfort," "mild discomfort" corresponds approximately to "mostly comfortable," and "high discomfort" corresponds approximately to "very little comfort" or, in some cases, to "no comfort" or "an absence of comfort." This discomfort information may be stored locally on the computing device 102, sent to the computing device 114 executing the clinical portal 126, and/or sent to the cloud-based computing system 116. For example, the user interface 1900 may be configured to receive a user input 1904, such as a pain score, from the user. The user input 1904 (e.g., a second user input) may be provided at or near the end of the rehabilitation session, or at any other desired time.

The user interface 1900 may also include treatment graphs. The treatment graphs can include information including an extension (angle), a flexion (angle), the pain score (scale), an ambulation (steps/day), a number of revolutions (i.e., revolutions performed on the of the electromechanical device 104), and any other desired information.

In some embodiments, the user interface 1900 presents an adjustment confirmation control configured to solicit a response regarding the user's comfort level with the position of the body part or the force exerted by the body part. The comfort level may be indicated by a binary selection (e.g., comfortable or not comfortable). In some embodiments, the comfort level may be an analog value that may be indicated numerically or with an analog input control, such as a slider or a rotary knob. In some embodiments, the comfort level may be indicated by one of several different comfort level values, such as an integer number from 1 to 5. In some embodiments, the comfort level may be indicated using controls for the user to maintain a setting or for the user to change the setting. More specifically, the control for the user to change the setting may provide for the user to change the setting in either of two or more directions. For example, the controls may allow the user to maintain the value of a setting, to increase the value of the setting, or to decrease the value of the setting.

In some embodiments, one or more of the controls may be provided by one or more of the sensors. For example, the user interface 1900 may prompt the user to move a body part until the user starts to feel discomfort. One or more of the sensors may measure the range of motion that the body part moved. The range of motion may be used for performing the rehabilitation regimen. For example, one or more of the sensors, such as a pressure sensor and/or a goniometer 106, may measure a physical response by the user, such as a flinch that indicates pain. A target value of a parameter may be set based upon the value of the parameter where the user indicated pain or discomfort. The target value of the parameter may then be used for performing the rehabilitation regimen of the treatment plan. A target parameter value may be the target value of the parameter. The target parameter value may be set based upon a value of the parameter where the user indicated pain or discomfort. The target parameter value may be set to X% of P, where X is a predetermined percentage, and P is the value of the parameter where the user indicated pain or discomfort. For example, if a user indicated pain at a pedal radius of 6.0 cm, and X is 90%, the target parameter value for the pedal position may be set to 5.4 cm, or 90% of 6.0 cm. Alternatively, the target parameter value may be set using an offset value that is added or subtracted from the value of the parameter where the user indicated pain or discomfort. For example, if a user indicated pain at pedal radius of 8.0 cm, and the offset value is −1.2 cm, then the target parameter value for the pedal radius may be set to 6.8 cm. Values of other parameters, such as target pressure or target speed, may be similarly adjusted.

In some embodiments, user interface 1900 of the user portal 118 can present an adjustment confirmation control configured to solicit a response regarding the patient's comfort level with the position of the body part or the force exerted by the body part. The comfort level may be indicated by a binary selection (e.g., comfortable or not comfortable). In some embodiments, the comfort level may be an analog value that may be indicated numerically or with an analog input control, such as a slider or a rotary knob. In some embodiments, the comfort level may be indicated by one of several different comfort level values, such as an integer number from 1 to 5. In some embodiments, the comfort level may be indicated using controls for the patient to maintain a setting or for the patient to change the setting. More specifically, the control for the patient to change the setting may provide for the patient to change the setting in either of two or more directions. For example, the controls may allow the patient to maintain the value of a setting, to increase the value of the setting, or to decrease the value of the setting.

Figure 20:
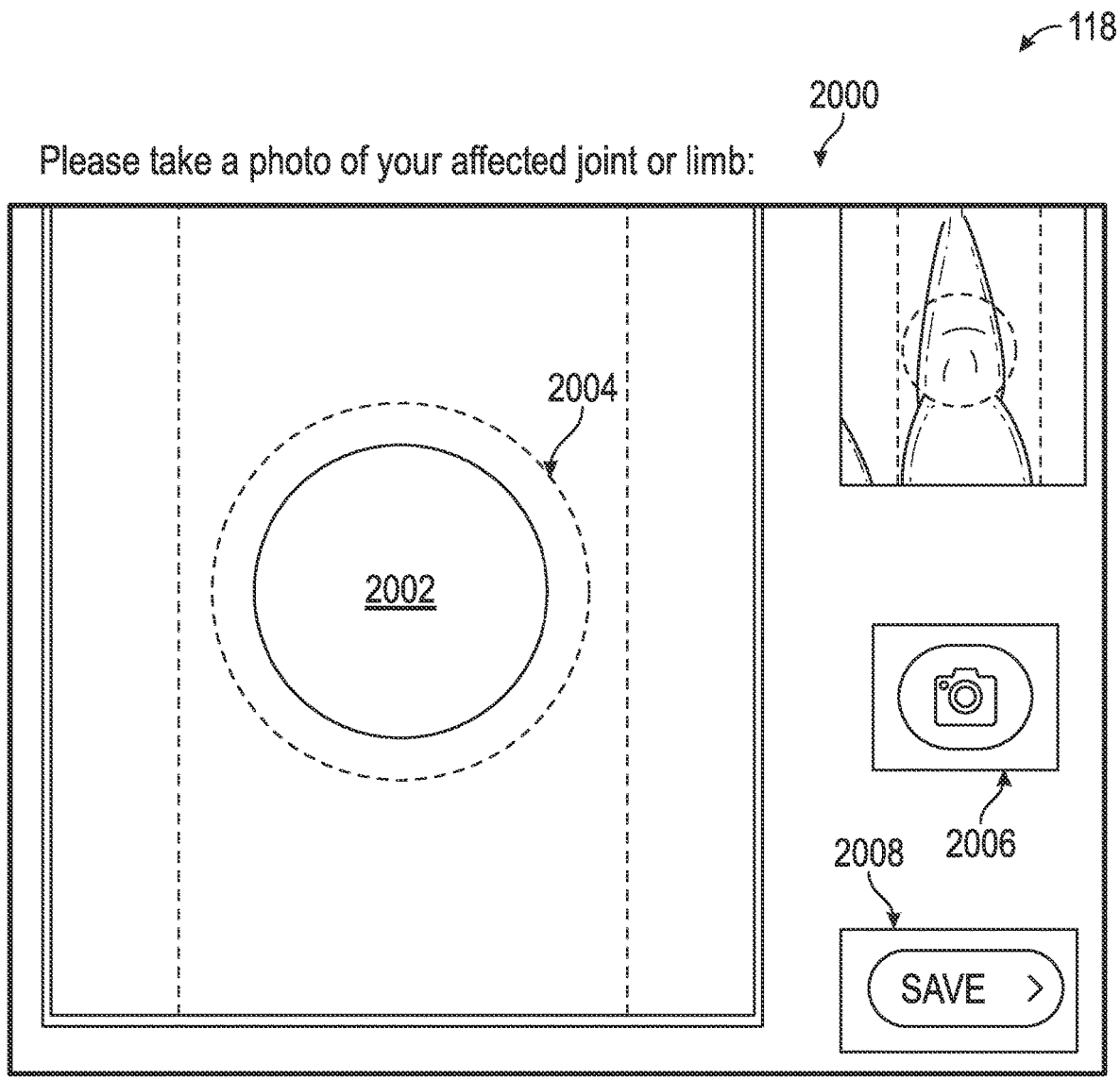
FIG. 20 illustrates an example user interface of the user portal, the user interface is configured to enable the user to capture an image of the body part under rehabilitation according to certain embodiments of this disclosure.

FIG. 20 illustrates, according to certain embodiments of this disclosure, an example user interface 2000 of the user portal 118. The user interface 2000 enables the user to capture an image of the body part under rehabilitation. For example, via an image capture device 616, an image capture zone 2002 is presented on the user interface 2000. The dotted lines 2004 may populate to show a rough outline of the leg, for example, with a circle to indicate where the user's kneecap (patella) should be in the image. This enables the patient or user to line up his or her leg/knee, or any other desired body part, for the image. The user may select a camera icon 2006 to capture the image. If the user is satisfied with the image, the user can select a save button 2008 to store the image on the computing device 102 and/or in the cloud-based computing system 116. Also, the image may be transmitted to the computing device 114 executing the clinical portal 126.

Figure 21A:
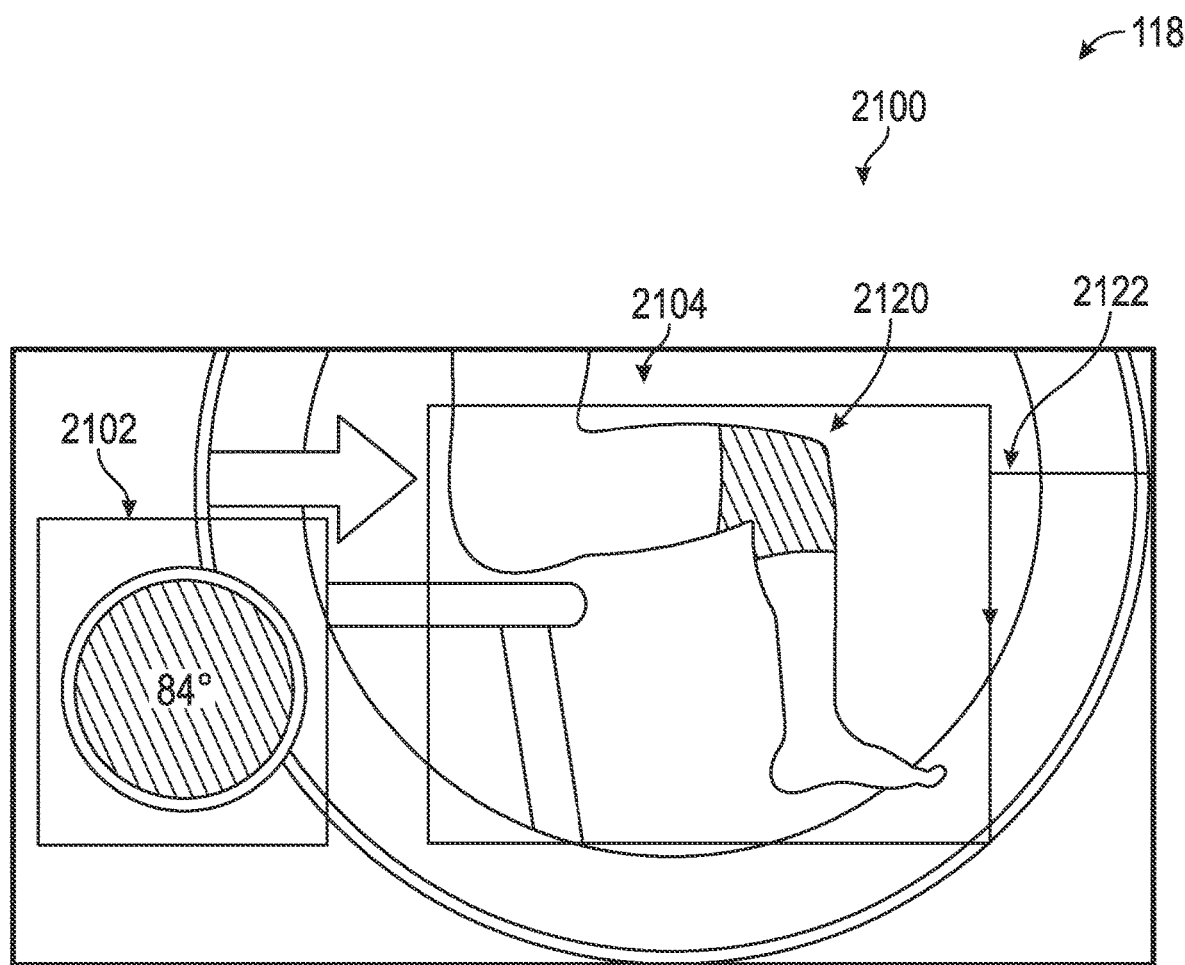
FIGS. 21A-D illustrate an example user interface of the user portal, and the user interface is configured to present angles of extension and bend of a lower leg relative to an upper leg according to certain embodiments of this disclosure.

FIGS. 21A-D illustrate an example user interface 2100 of the user portal 118. The user interface 2100 presents angles 2102 of an extension 2222 or a bend 2122 of a lower leg relative to an upper leg according to certain embodiments of this disclosure. As depicted in FIG. 21A, the user interface 2100 presents a graphical animation 2104 of the user's leg extending in real-time. The knee angle in the graphical animation 2104 may match the angle 2102 presented on the user interface 2100, for example, an angle of bend 2118 or an angle of extension 222. The computing device 102 may receive the angles of extension 2218 from the electronic device 106, and such device may be a goniometer or any other desired device that is worn by the user 2108 during an extension session and/or a pedaling session. To that end, although the graphical animation 2104 depicts the user 2108 extending his or her leg during an extension session, it should be understood that the user portal 118 may be configured to display the angles 2102 in real-time as the user 2108 operates the pedals 110 of the electromechanical device 104 in real-time.

Figure 21B:
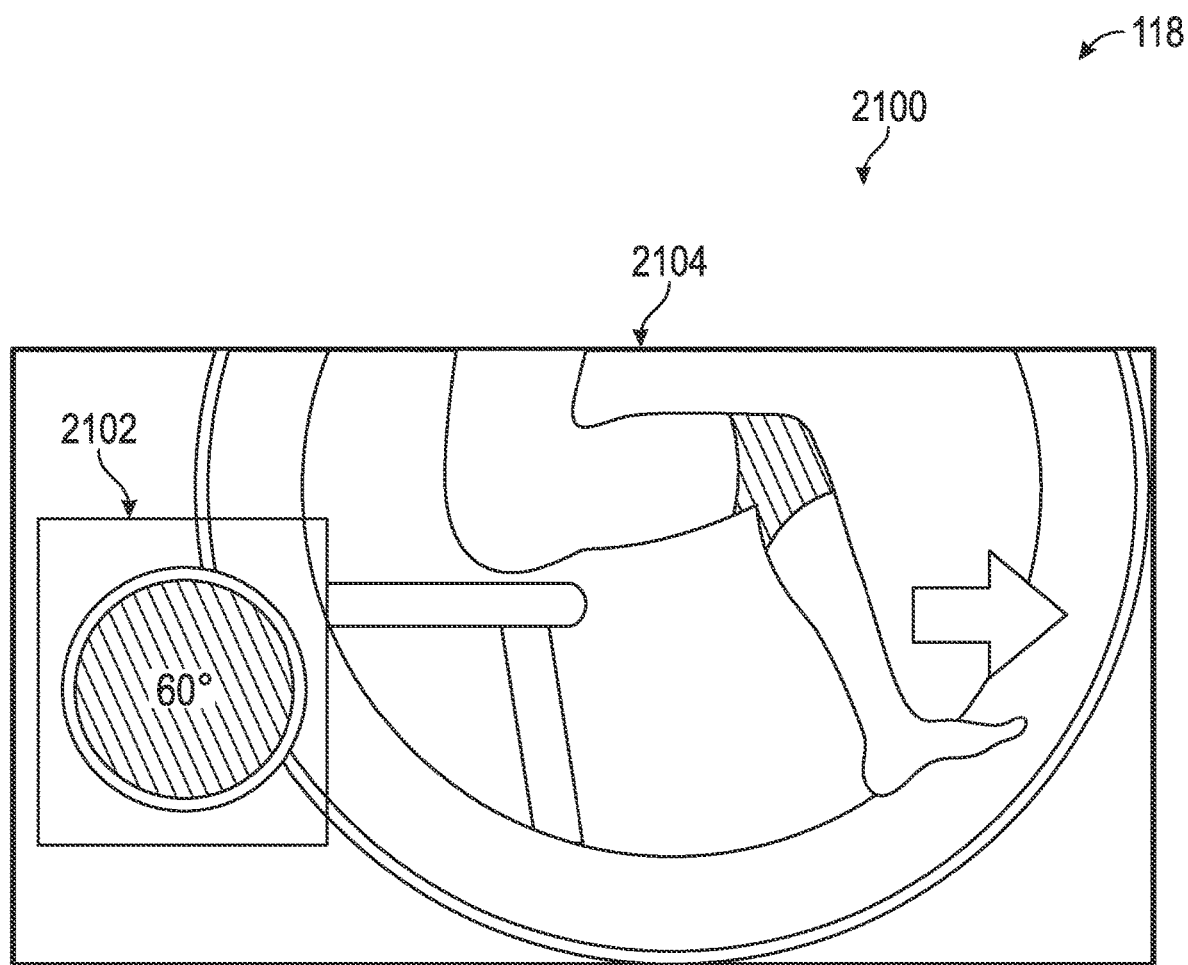
Figure 21C:
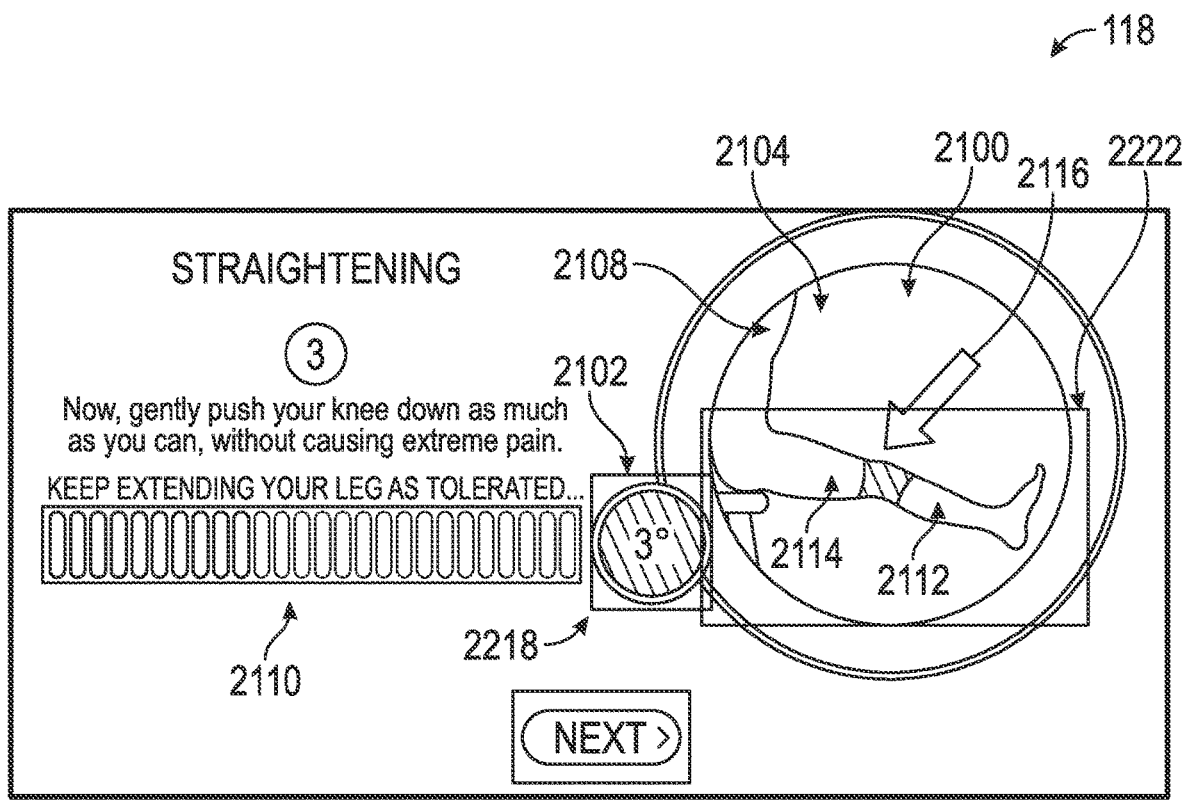
Figure 21D:
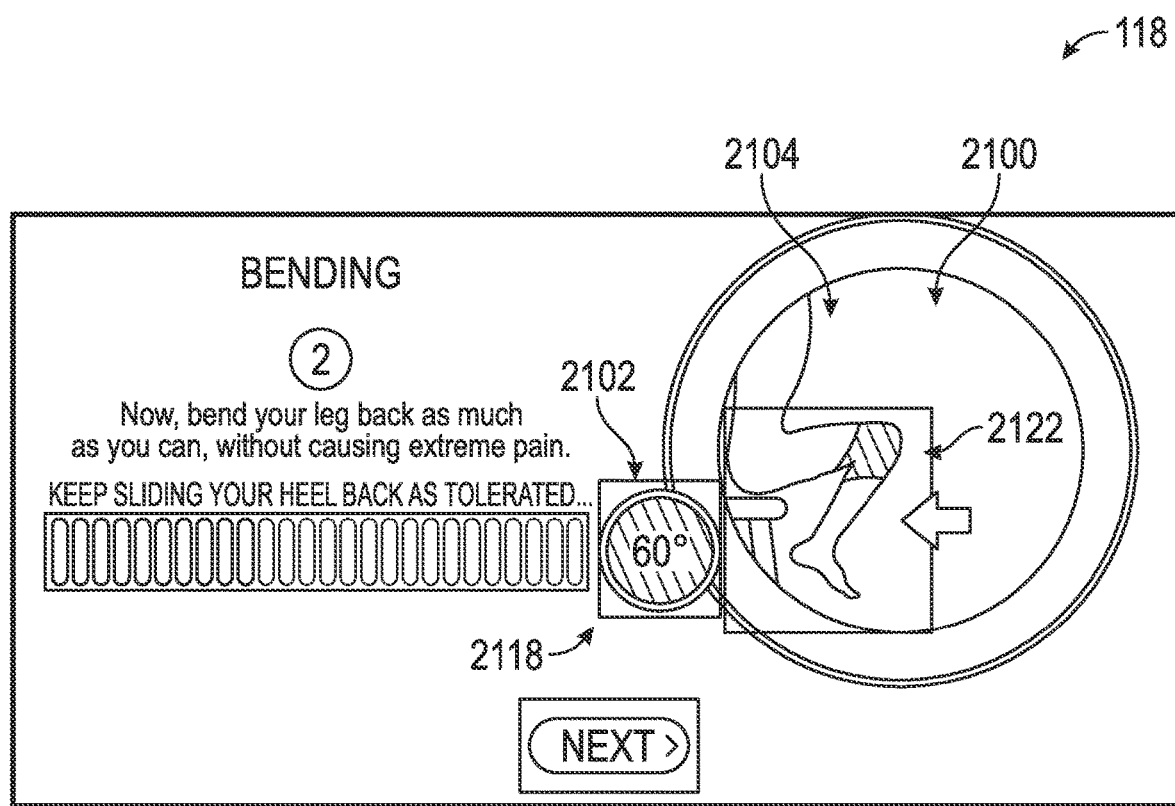

FIG. 21B illustrates the user interface 2100 with the graphical animation 2104 as the lower leg is extended farther away from the upper leg, and the angle 2102 changed from 84 to 60 degrees of extension. FIG. 21C illustrates the user interface 2100 with the graphical animation 2104 as the lower leg is extended even farther away from the upper leg. The computing device 102 may record the lowest angle to which the user 2108 is able to extend his or her leg as measured by the electronic device 106, such as the goniometer. The angle 2102 may be sent to the computing device 114 and that lowest angle may be presented on the clinical portal 126 as an extension statistic for that extension session. Further, a bar 2110 may be presented and the bar 2110 may fill from left to right over a set amount of time. A notification may indicate that the patient or user 2108 should push down on his or her knee over a set amount of time or until a set amount of time, minimum or maximum, has elapsed. The user interface 2100 in FIG. 21D is similar to FIG. 21C but it presents the angle of bend 2118, measured by the electronic device 106, such as the goniometer, as the user 2108 retracts his or her lower leg closer to his or her upper leg (e.g., during the bend 2122). As depicted, the graphical animation 2104 presented on the user interface 2100 in real-time depicts the angle of the knee matching the angle 2102. The computing device 102 may record the highest angle that the user 2108 is able to bend his or her leg as measured by the electronic device, such as the goniometer 106. That angle 2102 may be sent to the computing device 114 and that highest angle may be presented on the clinical portal 126 as a bend statistic for that bend session.

Figure 22:
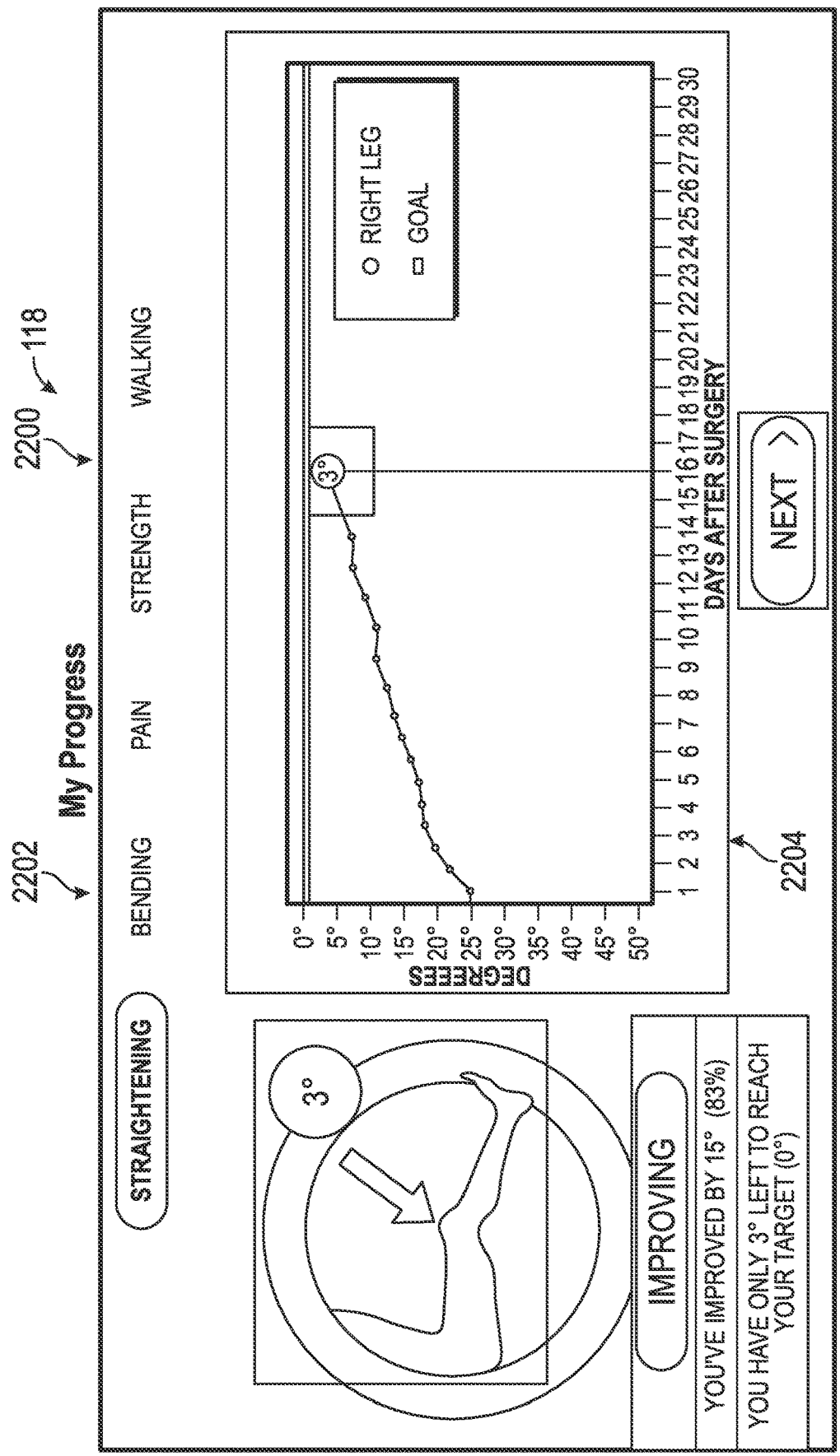
FIG. 22 illustrates an example user interface of the user portal, and the user interface is configured to present a progress screen for a user extending the lower leg away from the upper leg according to certain embodiments of this disclosure.

FIG. 22 illustrates an example user interface 2200 of the user portal 118. The user interface 2200 presents a progress report 2202 for a user extending the lower leg away from the upper leg according to certain embodiments of this disclosure. The user interface 2200 presents a graph 2204 wherein the degrees of extension are on a y-axis and the days after surgery are on an x-axis. The angles depicted in the graph 2204 are the smallest angles achieved each day. The user interface 2200 also depicts the smallest angle the user has achieved for extension and indicates an percentage of improvement (83%) in extension since beginning the treatment plan. The user interface 2200 also indicates how many degrees are left before reaching a target extension angle. The user interface 2000 may also display a summary box 2206. The summary box 2206 may include information, such as the amount of strength improvement in the legs, the amount of strength improvement needed to satisfy a target strength goal, or any other desired information. The summary box 2206 may include information, such as a score based on the target values, performance of the user 2108, or any other desired information. For example, the target value may be one or more of a target heartrate, a target force that the user 2108 is to exert on the one or more pedals 110, a target range of motion of the first and/or second body parts 2112, 2114, a target position of the one or more pedals 110 on the radially-adjustable couplings 124, a target angle of flex at the joint 2116, a target number of bends 2122 or extensions 2222, a target number of steps, a target temperature, or any other desired target value.

Figure 23:
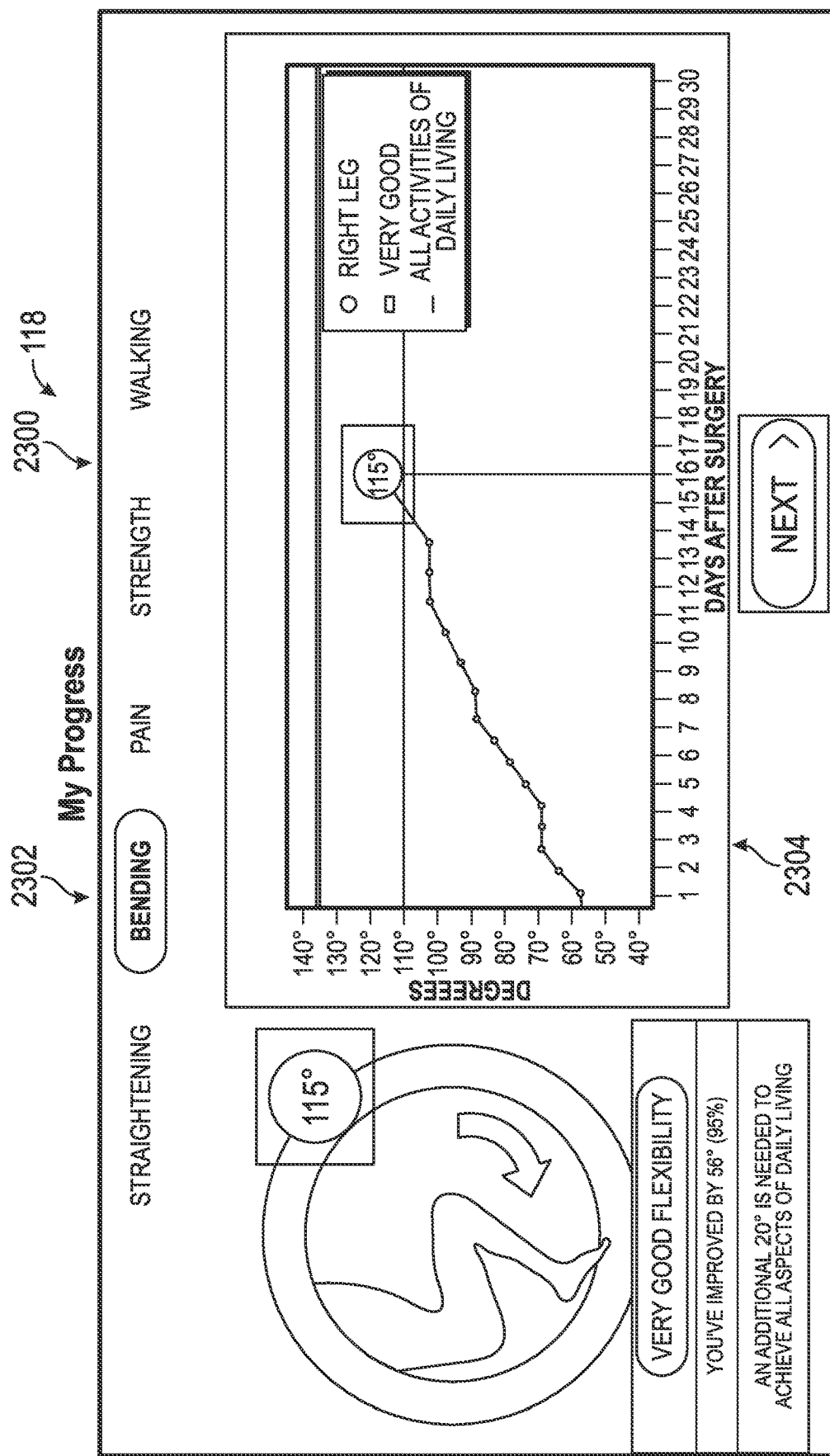
FIG. 23 illustrates an example user interface of the user portal, and the user interface is configured to present a progress screen for a user bending the lower leg toward the upper leg according to certain embodiments of this disclosure.

FIG. 23 illustrates an example user interface 2300 of the user portal 118. The user interface 2300 presents a progress screen 2302 for a user bending the lower leg toward the upper leg according to certain embodiments of this disclosure. The user interface 2300 presents a graph 2304 with the degrees of bend on a y-axis and the days after surgery on the x-axis. The angles depicted in the graph 2304 are the highest angles of bend achieved each day. The user interface 2200 also depicts the smallest angle the user has achieved for bending and indicates a percentage of improvement (95%) in extension since beginning the treatment plan. The user interface 2200 also indicates how many degrees are left before reaching a target bend angle.

Figure 24:
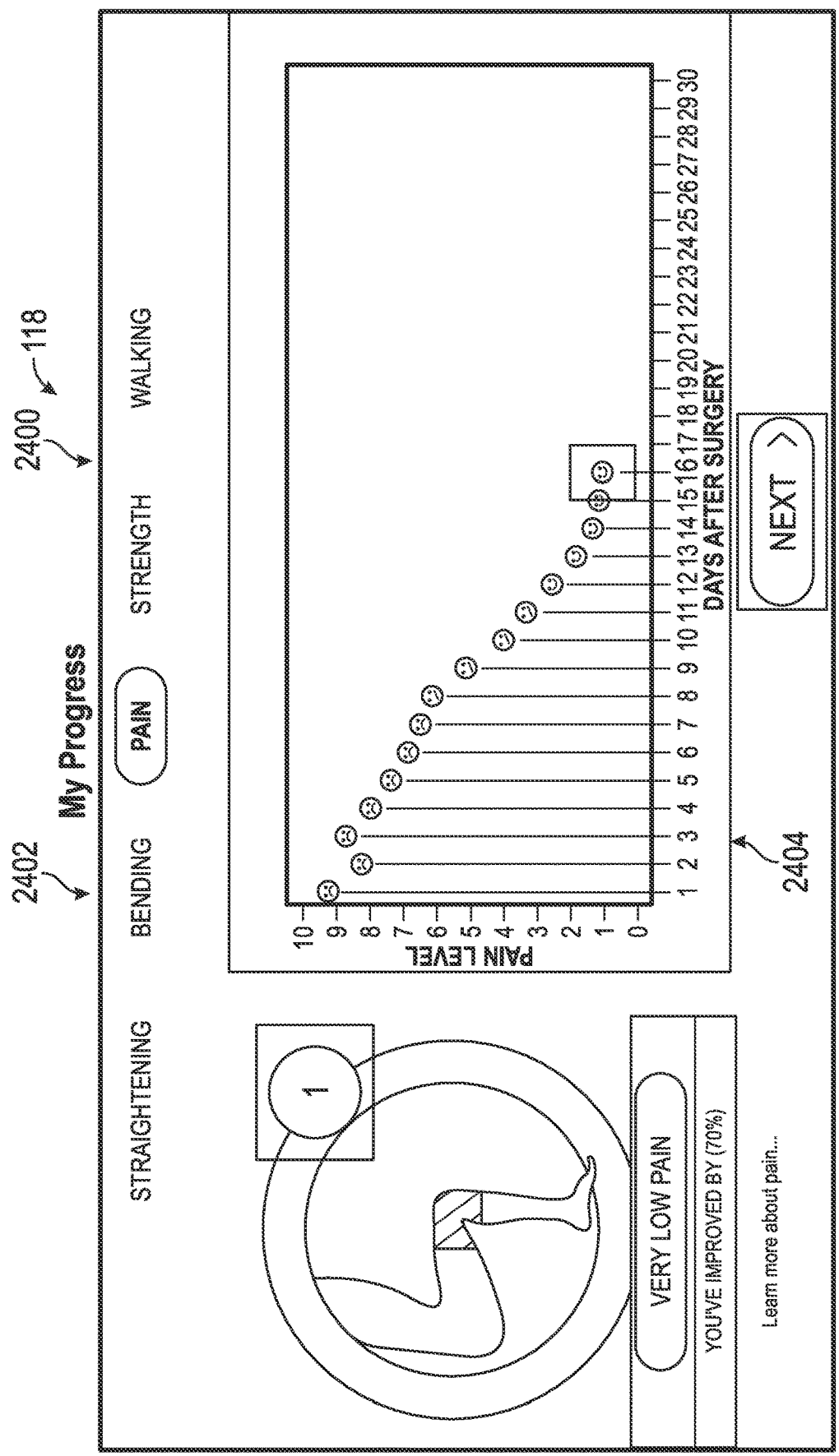
FIG. 24 illustrates an example user interface of the user portal, and the user interface is configured to present a progress screen for measuring a pain level of the user according to certain embodiments of this disclosure.

FIG. 24 illustrates an example user interface 2400 of the user portal 118. The user interface 2400 presents a progress screen 2402 for a discomfort level of the user according to certain embodiments of this disclosure. The user interface 2400 presents a graph 2404 with the discomfort level on a y-axis and the days after surgery on the x-axis. The user interface 2400 also depicts the lowest discomfort level the user has reported and a notification indicating a measurement of the reduction in discomfort that the user has experienced throughout the treatment plan.

Figure 25:
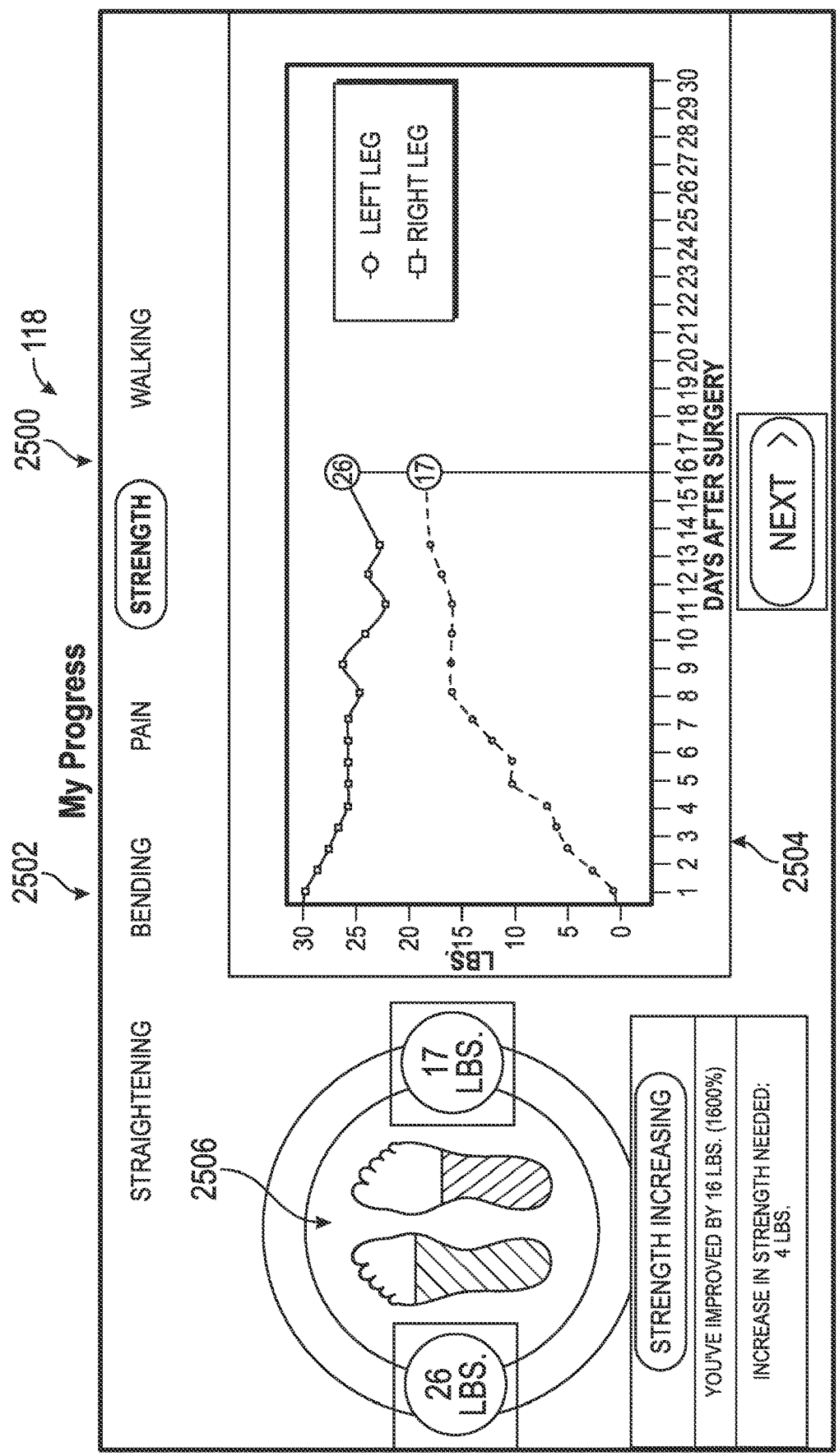
FIG. 25 illustrates an example user interface of the user portal, and the user interface is configured to present a progress screen for measuring a strength of a body part according to certain embodiments of this disclosure.

FIG. 25 illustrates, according to certain embodiments of this disclosure, an example user interface 2500 of the user portal 118. The user interface presents a progress screen 2502 for a strength of a body part. The user interface 2500 presents a graph 2504 with the pounds of force exerted by the patient for both the left leg and the right leg on a y-axis and the days after surgery on the x-axis. The graph 2504 may show an average for left and right leg for a current session. For the number of sessions a user does each day, the average pounds of force for those sessions may be displayed for prior days as well. The user interface 2500 also depicts graphical representations 2506 of the left and right feet and a maximum amount of force the user has exerted for the left and right leg. The maximum amount (e.g., in pounds) of force depicted may be computed when the electromechanical device is operating in the active mode. The user may select to see statistics for prior days and the average level of active sessions for the current day may be presented as well. The user interface 2500 indicates the amount of strength improvement in the legs and the amount of strength improvement needed to satisfy a target strength goal, for example, in the summary box 2508.

Figure 26:
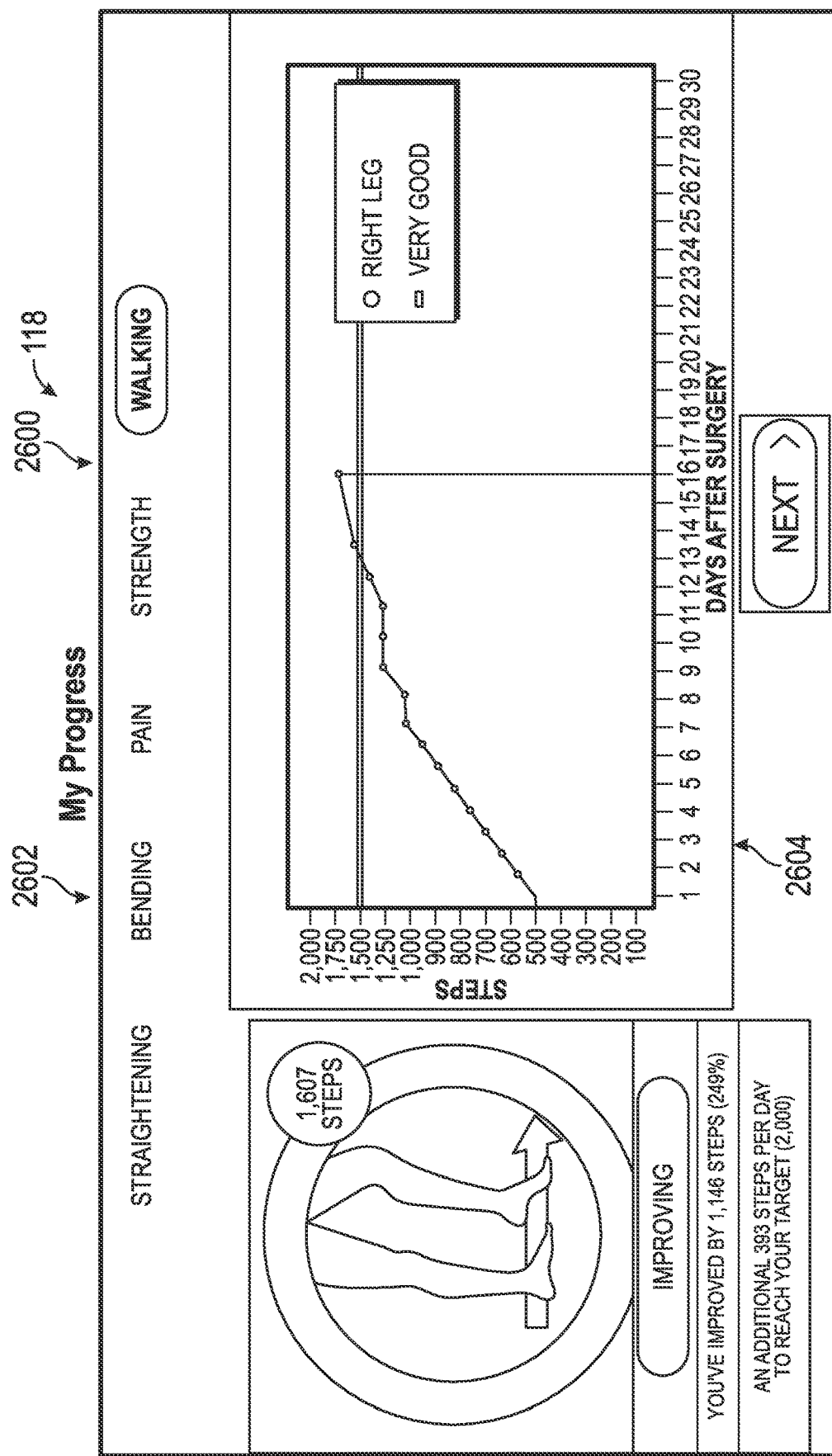
FIG. 26 illustrates an example user interface of the user portal, and the user interface is configured to present a progress screen capable of displaying an amount of steps of the user according to certain embodiments of this disclosure.

FIG. 26 illustrates, according to certain embodiments of this disclosure, an example user interface 2600 of the user portal 118. The user interface presents a progress screen 2602 for a number of steps of the user. The user interface 2600 presents a graph 2604 with the number of steps taken by the user on a y-axis and the days after surgery on the x-axis. The user interface 2500 also depicts the highest number of steps the user has taken among all of the days in the treatment plan, the amount the user has improved in steps per day since starting the treatment plan, and the number of additional steps needed to meet a target step goal. The user may select to view prior days to see the total number of steps they have taken per day.

Figure 27:
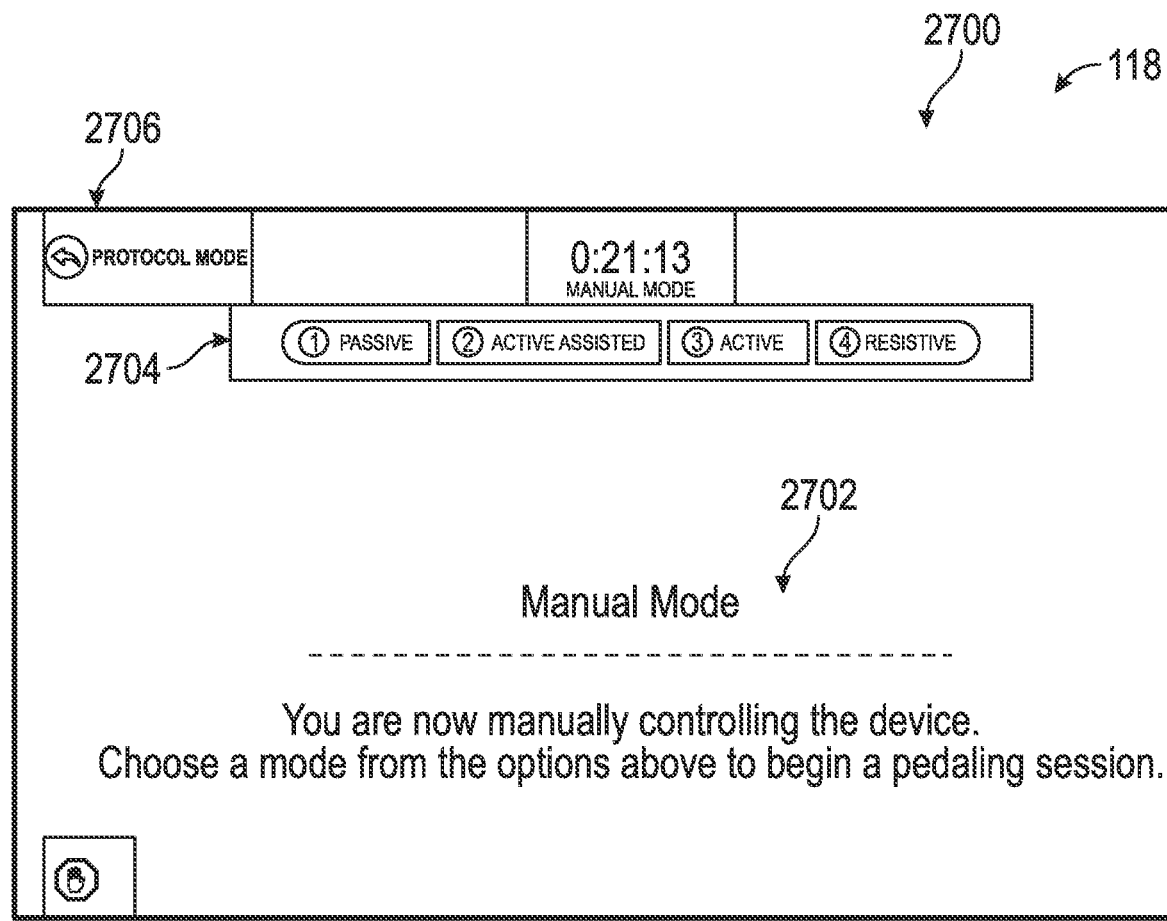
FIG. 27 illustrates an example user interface of the user portal, and the user interface is configured to present that the electromechanical device is operating in a manual mode according to certain embodiments of this disclosure.

FIG. 27 illustrates, according to certain embodiments of this disclosure, an example user interface 2700 of the user portal 118. The user interface 2700 presents that the electromechanical device 104 is operating in a manual mode 2702. During the manual mode 2702, the user may set the speed, resistance, time to exercise, position of pedals, etc. In such a configuration, the control system for the electromechanical device 104 may not provide any assistance to operation of the electromechanical device 104. When the user selects any of the modes in the box 2704, a pedaling session may begin. Further, when the user selects button 2706, the user portal 118 may return to the user interface 1300 depicted in FIG. 13.

Figure 28:
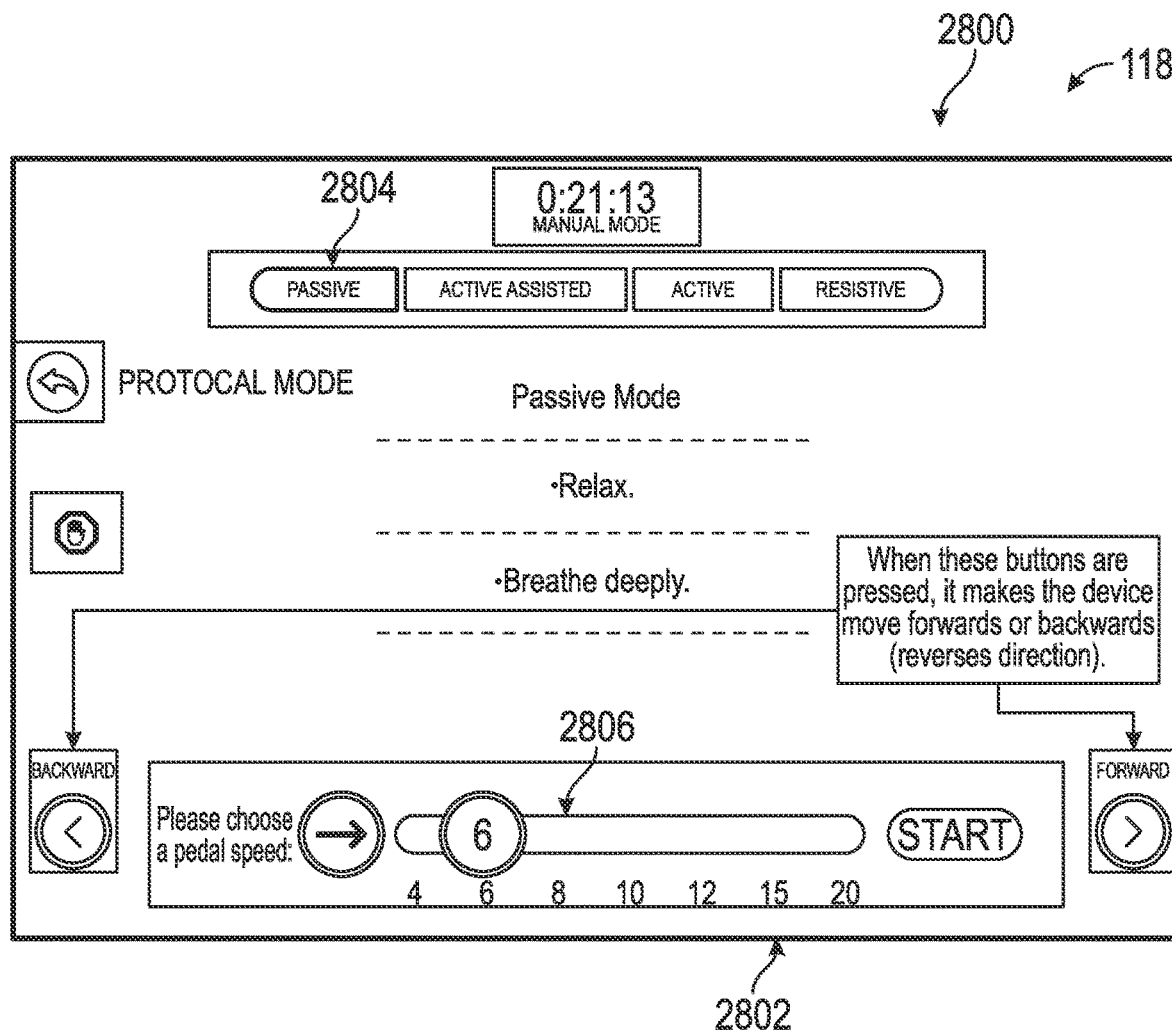
FIG. 28 illustrates an example user interface of the user portal, and the user interface is configured to present an option to modify a speed of the electromechanical device operating in the passive mode according to certain embodiments of this disclosure.

FIG. 28 illustrates, according to certain embodiments of this disclosure, an example user interface 2800 of the user portal 118. The user interface 2800 presents an option 2802 to modify a speed of the electromechanical device 104 operating in the passive mode 2804. The user may slide button 2806 to adjust the speed as desired during the passive mode 2804 where the electric motor is providing the driving force of the radially-adjustable couplings.

Figure 29:
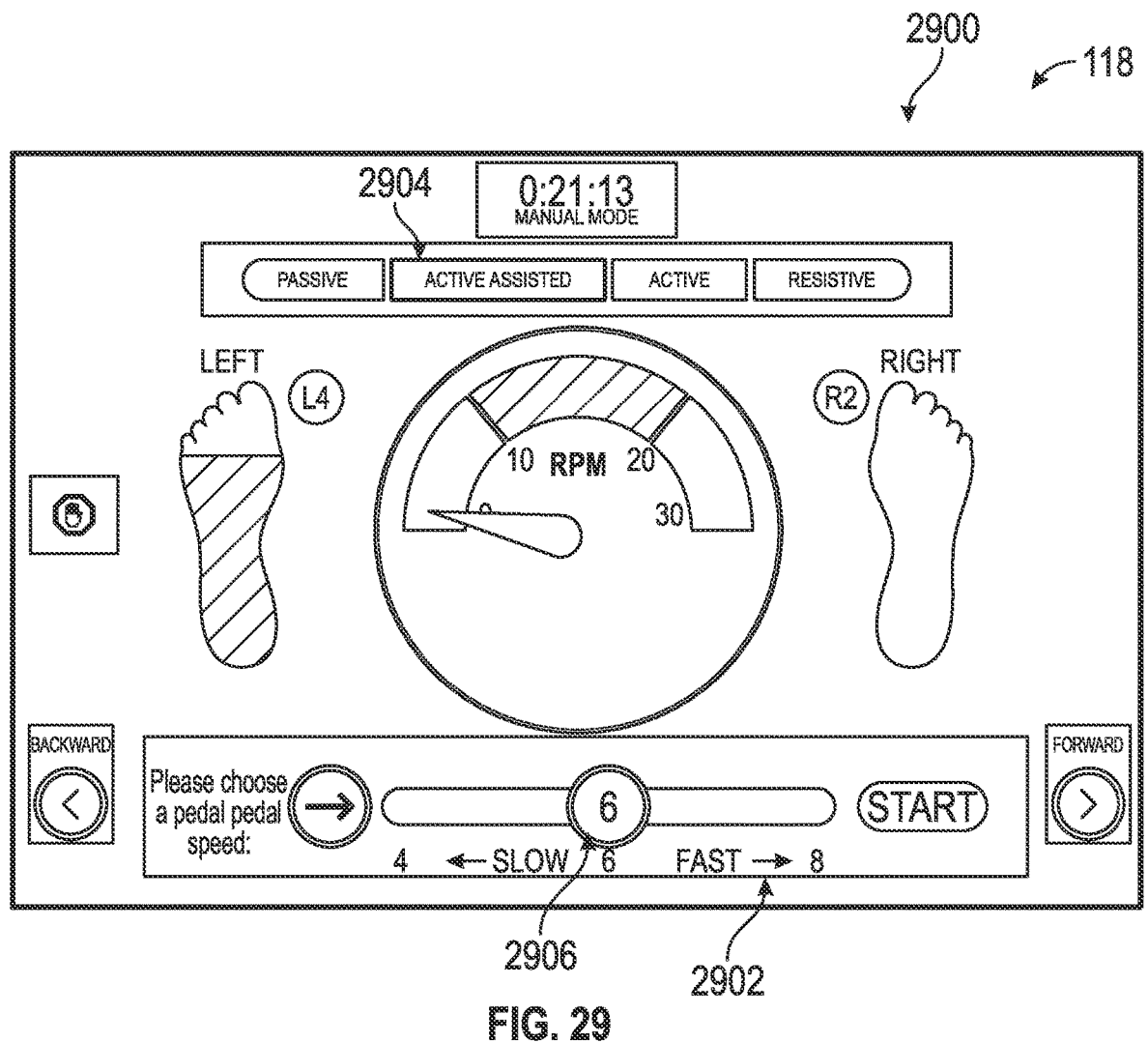
FIG. 29 illustrates an example user interface of the user portal, and the user interface is configured to present an option to modify a minimum speed of the electromechanical device operating in the active-assisted mode according to certain embodiments of this disclosure.

FIG. 29 illustrates, according to certain embodiments of this disclosure, an example user interface 2900 of the user portal 118. The user interface 2900 presents an option 2902 to modify a minimum speed of the electromechanical device 104 operating in the active-assisted mode 2904. The user may slide button 2906 to adjust the minimum speed that the user should maintain before the electric motor begins providing driving force.

Figure 30:
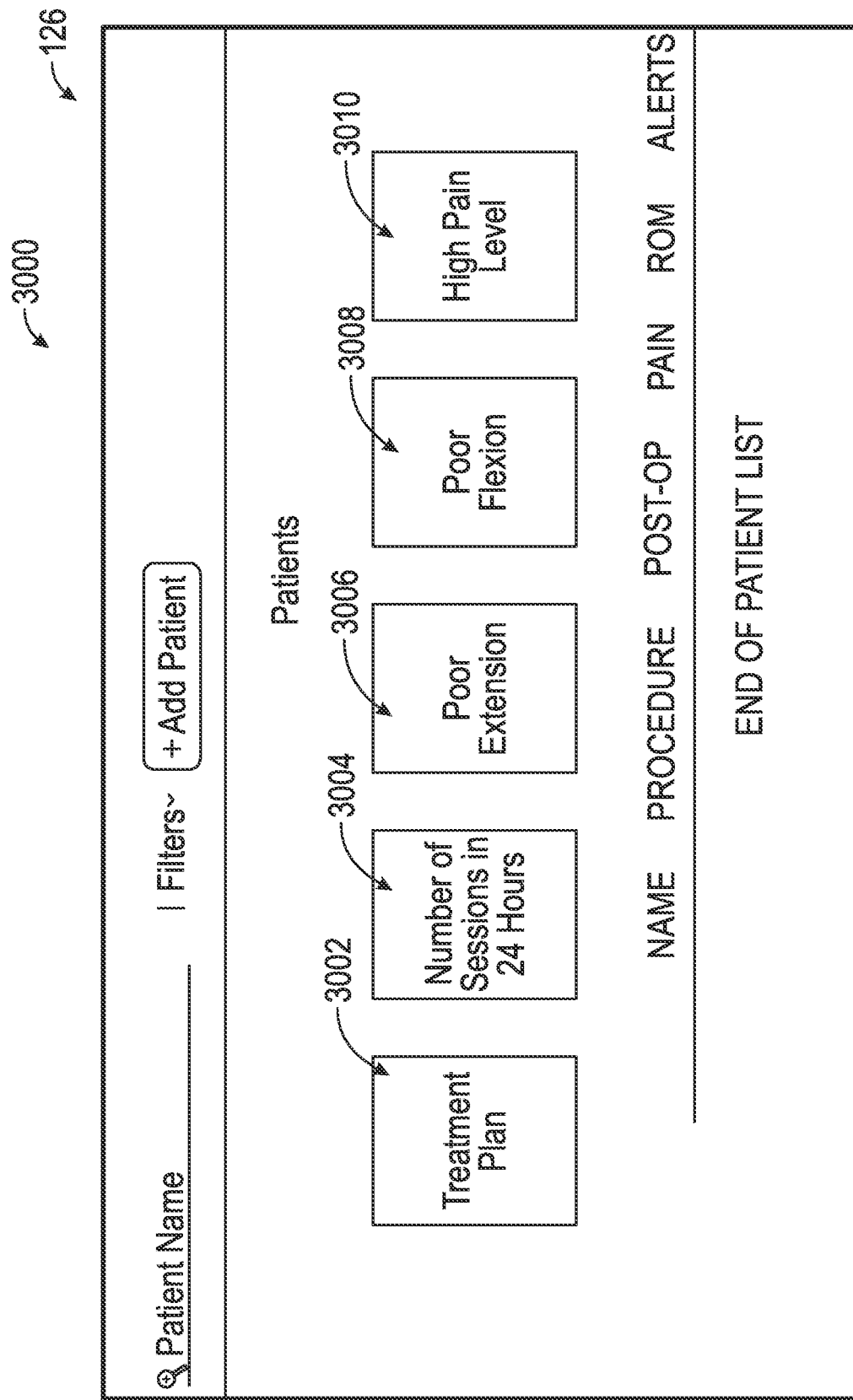
FIG. 30 illustrates an example user interface of the clinical portal, and the user interface is configured to present various options available to the clinician according to certain embodiments of this disclosure.

FIG. 30 illustrates, according to certain embodiments of this disclosure, an example user interface 3000 of the clinical portal 126, wherein the user interface 3000 presents various options available to the clinician/physician. The clinical portal 126 may retrieve a list of patients for a particular physician who logs into the clinical portal 126. The list of patients may be stored on the computing device 114 or retrieved from the cloud-based computing system 116. A first option 3002 may enable the clinician to generate treatment plans for one or more of the patients, as described above. A second option 3004 may enable the clinician to view the number of sessions that each of the patients have completed in 24 hours. This may enable the clinician to determine whether the patients are keeping up with the treatment plan and whether to send notifications to those patients not completing the sessions. A third option 3006 may enable the clinician to view the patients who have poor extension (e.g., angle of extension above a target extension for a particular stage in the treatment plan). A fourth option 3008 may enable the clinician to view the patients who have poor flexion (e.g., angle of bend below a target bend for a particular stage in the treatment plan). A fifth option 3010 may enable the clinician to view the patients reporting high pain levels. Regarding any of the options, the clinician can contact the user and inquire as to the status of their lack of participation, or degree of extension, flexion and pain level etc. The clinical portal 126 provides the benefit of direct monitoring of the patients progress by the clinician, which may enable faster and more effective recoveries.

Further, the clinical portal may include an option to control aspects of operating the electromechanical device 104. For example, while the user is engaged in a pedaling session or when the user is not engaged in the pedaling session, the clinician may use the clinical portal 126 to adjust a position of a pedal 110 based on angles of extension/bend received from the computing device 102 and/or the goniometer 106 in real-time. In response to determining an amount of force exerted by the user exceeds a target force threshold, such as the force threshold 1730, the clinical portal 126 may enable the clinician to adjust the amount of resistance provided by the electric motor 122. The clinical portal 126 may enable the clinician to adjust the speed of the electric motor 122, and so forth. The user interfaces can include additional and/or fewer components and are not limited to those illustrated in FIGS. 13-30.

Figure 31:
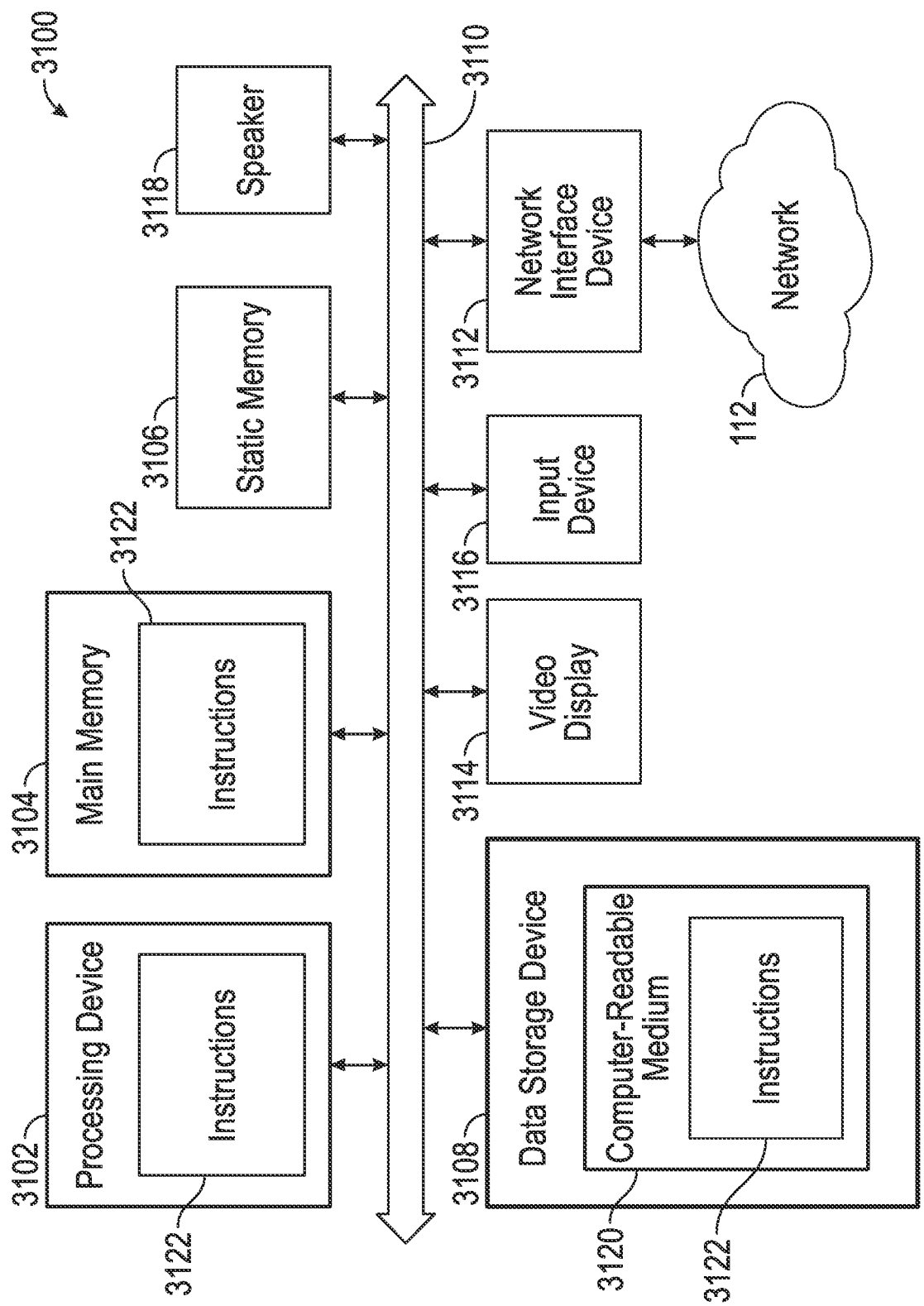
FIG. 31 illustrates an example computer system according to certain embodiments of this disclosure.

FIG. 31 illustrates, in accordance with one or more aspects of the present disclosure, example computer system 3100, which can perform any one or more of the methods described herein. In one example, computer system 3100 may correspond to the computing device 102 (e.g., user computing device), the computing device 114 (e.g., clinician computing device), one or more servers of the cloud-based computing system 116, the training engine 130, the servers 128, the motor controller 120, the pedals 110, the goniometer 106, and/or the wristband 108 of FIG. 1. The computer system 3100 may be capable of executing the user portal 118 and/or the clinical portal 126 of FIG. 1. The computer system 3100 may be connected (e.g., networked) to other computer systems in a LAN, an intranet, an extranet, or the Internet. The computer system 3100 may operate in the capacity of a server in a client-server network environment. The computer system 3100 may comprise a personal computer (PC), a tablet computer, a motor controller, a goniometer, a wearable device (e.g., wristband 108), a set-top box (STB), a personal Digital Assistant (PDA), a mobile phone, a camera, a video camera, an Internet of Things (IoT) sensor or device, or any device capable of executing a set of instructions (sequential or otherwise) that specify actions to be taken by that device. Further, while only a single computer system is illustrated, the term "computer" shall also be taken to include any collection of computers that individually or jointly execute a set (or multiple sets) of instructions to perform any one or more of the methods discussed herein.

The computer system 3100 comprises a processing device 3102, a main memory 3104 (e.g., read-only memory (ROM), flash memory, dynamic random access memory (DRAM) such as synchronous DRAM (SDRAM)), a static memory 3106 (e.g., flash memory, static random access memory (SRAM)), and a data storage device 3108, which communicate with each other via a bus 3110.

Processing device 3102 represents one or more general-purpose processing devices such as a microprocessor, central processing unit, or the like. More particularly, the processing device 3102 may comprise a complex instruction set computing (CISC) microprocessor, reduced instruction set computing (RISC) microprocessor, very long instruction word (VLIW) microprocessor, or a processor implementing other instruction sets or processors implementing a combination of instruction sets. The processing device 3102 may also comprise one or more special-purpose processing devices such as an application specific integrated circuit (ASIC), a field programmable gate array (FPGA), a digital signal processor (DSP), network processor, or the like. The processing device 3102 is configured to execute instructions for performing any of the operations and steps discussed herein.

The computer system 3100 may further comprise a network interface device (NID) 3112. The computer system 3100 also may comprise a video display 3114 (e.g., a liquid crystal display (LCD) or a cathode ray tube (CRT)), one or more input devices 3116 (e.g., a keyboard and/or a mouse), and one or more speakers 3118 (e.g., a speaker). In one illustrative example, the video display 3114 and the input device(s) 3116 may be combined into a single component or device (e.g., an LCD touch screen).

The data storage device 3108 may comprise a computer-readable storage medium 3120 on which the instructions 3122 (e.g., implementing control system, user portal, clinical portal, and/or any functions performed by any device and/or component depicted in the FIGURES and described herein) embodying any one or more of the methodologies or functions described herein are stored. The instructions 3122 may also reside, completely or at least partially, within the main memory 3104 and/or within the processing device 3102 during execution thereof by the computer system 3100. As such, the main memory 3104 and the processing device 3102 also constitute computer-readable media. The instructions 3122 may further be transmitted or received over a network via the network interface device 3112.

While the computer-readable storage medium 3120 is shown in the illustrative examples to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium capable of storing, encoding or carrying a set of instructions for execution by the machine and which cause the machine to perform any one or more of the methodologies of the present disclosure. The term "computer-readable storage medium" shall accordingly be taken to include, but not be limited to, solid-state memories, optical media, and magnetic media. The computer system 3100 can include additional and/or fewer components and is not limited to those illustrated in FIG. 31.

In one aspect, a system for rehabilitation includes one or more electronic devices 106 comprising one or more memory devices 938 storing instructions 3122, one or more network interface cards 940, and one or more sensors 942. The one or more electronic devices 106 may be coupled to a user 2108. The system for rehabilitation may further include one or more processing devices 944 operatively coupled to the one or more memory devices 938, the one or more network interface cards 940, and the one or more sensors 942. The one or more processing devices 944 may be configured to execute the instructions 3122 to receive information from the one or more sensors 942. The one or more processing devices 944 may further be configured to execute the instructions 3122 to transmit, via the one or more network interface cards 940, the information to a computing device 102 controlling an electromechanical device 104. The information may be received while a user 2108 is engaging one or more pedals 110 of the electromechanical device 104. Engaging the pedals 110 can include the user 2108 moving the pedals 2108 or causing the pedals 2108 to not move. Engaging can mean engaging at the time the information is received, about to engage proximately in time or distance, or having just engaged with an intention of engaging again. The one or more processing devices 944 may further be configured to transmit, via the one or more network interface cards 940, the information to a second computing device 114 to cause the second computing device 114 to present the information. Presenting the information may be in a user portal 118 of a computing device 102 (e.g., to a user 2108), in a clinical portal 126 of a computing device 114 (e.g., to a clinician), or in any other desired device. The information may comprise a plurality of angles 2102. The plurality of angles 2102 may comprise at least one of angles during an extension 2222 and a bend 2122 of body parts of a user 2108. For example, the plurality of angles 2102 may comprise at least one of angles of extension 2218 of a first body part 2112 of a user 2108 extended away from a second body part 2114 at a joint 2116 and angles of bend 2118 of the first body part 2112 retracting closer toward the second body part 2114. The first body part 2112 may be a lower leg, a forearm, or any other desired body part. The second body part 2114 may be an upper leg, an upper arm, or any other desired body part. The joint 2116 may be a knee, an elbow, or any other desired body part. For example, the one or more electronic devices 106 may be configured for coupling 124 to the lower leg and the upper leg and for flexing adjacent to the knee.

The processing device may determine whether a range of motion threshold condition is satisfied based on the plurality of angles, such as the set of angles of extension 2218 and the set of angles of bend 2118. Responsive to determining that the range of motion threshold condition is satisfied, the processing device may change a diameter (or radius, or other measurement) of a range of motion of the one of the pedals 110 by modifying a position of one of the pedals 110 on one of the radially-adjustable couplings 124. Satisfying the range of motion threshold condition may indicate that the affected body part is strong enough or flexible enough to increase the range of motion allowed by the radially-adjustable couplings 124. For example, if the range of motion threshold is satisfied, the computing device 102 may adjust a first position of a first pedal 110 on a first radially-adjustable coupling 124 of the electromechanical device 104. The first position may be adjusted to change a first diameter of a first range of motion of the first pedal 110. The computing device 102 may also maintain a second diameter of a second range of motion of a second pedal 110 on a second radially-adjustable coupling 124 of the electromechanical device 104 (e.g., a pedal for an opposing leg or arm to the first leg or arm engaging the first pedal). The computing device 102 can maintain the second range of motion of the second pedal 110 at approximately a constant second diameter. The computing device 102 may adjust a first position of a first pedal 110 on a first radially-adjustable coupling 124 of the electromechanical device 104, wherein the adjusting of the first position changes a first diameter of a first range of motion of the first pedal 110. The computing device 102 may adjust a second position of a second pedal 110 on a second radially-adjustable coupling 124 of the electromechanical device 104, wherein the adjusting of the second position changes a second diameter of a second range of motion of the second pedal 110.

The one or more processing devices 944 may execute the instructions 3122 to determine a number of extensions and/or a number of bends. The number of extension may be the number of times the first body part 2112 is extended away from the second body part 2114. The number of bends may include the number of times the first body part 2112 is retracted closer toward the second body part 2114. The one or more processing devices 944 may execute the instructions 3122 to transmit, via the one or more network interface cards 940, the number of extensions to a second computing device 114, wherein the transmitting the number of extensions to the second computing device 114 causes the second computing device 114 to present the number of extensions. The one or more processing devices 944 may execute the instructions 3122 to transmit, via the one or more network interface cards 940, the number of bends to a second computing device 114, wherein the transmitting the number of bends to the second computing device 114 causes the second computing device 114 to present the number of bends. The number of extensions and/or the number of bends may change during the rehabilitation session, for example, in real-time. The number of extensions and/or the number of bends may be presented at the end of the rehabilitation session or any other desired time. The number of extensions and/or the number of bends can be displayed, for example, on a user interface 2000, for the user 2108 to monitor the progress of the plurality of extension sessions and/or the plurality of bend sessions throughout the treatment plan. As part of the treatment plan, the user 2108 may have a prescribed number of extensions and/or bends to achieve, for example, per exercise session or per day. Being able to view the number of extensions and/or bends in real-time, the user can determine how many more extensions/bends are needed to reach the desired number of extensions and/or bends. The number of extensions and/or the number of bends can be presented on a user interface of the clinical portal 126 for the clinician to monitor the number of extensions and/or the number of bends to access the progress of the user 2108. The clinician can adjust the prescribed number of extensions and/or bends in the treatment plan.

The transmitting the plurality of angles 2102 to the computing device 102 may cause the computing device 102 to present the plurality of angles 2102 in a graphical animation 2104 of the first body part 2112 and the second body part 2114 moving in real-time during the extension 2222 or the bend 2122. For example, the one or more sensors 942 may be worn by the user 2108 and the one or more processing devices 944 may be configured to present, on a user interface 2000 of a control system, a graphical animation 2104 of the first body part 2112, the second body part 2114, and the joint 2116 of a user 2108 as the first body part 2112 is extended away from the second body part 2114 via the joint 2116. The graphical animation 2104 can include a plurality of angles of extension 2218 as the plurality of angles of extension 2218 changes during the extension 2222. The one or more processing devices 944 may be configured to store as an extension statistic for an extension session a lowest value, such as a smallest angle, of the plurality of angles of extension 2218. The plurality of extension statistics may be stored for a plurality of extension sessions specified by a treatment plan 1302. The one or more processing devices 944 may be configured to present, via a graphical element on the user interface 2000, a progress of the plurality of extension sessions throughout the treatment plan 1302.

The one or more processing devices 944 may be configured to present, on a user interface 2000 of a control system, a graphical animation 2104 of a first body part 2112, a second body part 2114, and a joint 2116 of a user 2108 as the first body part 2112 is retracted closer to the second body part 2114 via the joint 2116. The graphical animation 2104 may include a plurality of angles of bend 2118 as the plurality of angles of bend 2118 changes during the bend 2122. The one or more processing devices 944 may be configured to store a highest value, such as a largest angle, of the plurality of angles of bend 2118 as a bend statistic for a bend session, wherein a plurality of bend statistics may be stored for a plurality of bend sessions specified by a treatment plan 1302. The one or more processing devices 944 may be configured to present, via a graphical element on the user interface 2000, a progress of the plurality of bend sessions throughout the treatment plan 1302. For example, the processing device 944 may present progress of the set of bend sessions throughout the treatment plan 1302 via a graphical element (e.g., line graph, bar chart, etc.) on the user interface 2000 presenting the set of bend statistics.

The one or more processing devices 944 may be configured to control an image capture device 616 to capture an image 2010 of a body part of a user 2108 being rehabilitated (e.g., take a photograph of a site 2012, such as a joint 2116, and store the photograph in the memory device 938). For example, the image capture device 616 may capture a site 2012 of the user's knee and part of the user's lower and upper legs. The one or more processing devices 944 may further be configured to transmit, to a computing device 114 operated by a clinician, the image 2010 of the body part, wherein the computing device 114 may be communicatively coupled to the control system.

The one or more processing devices 944 may further be configured to receive, from a wearable device, a number of steps taken by a user 2108 over a certain time period. The wearable device may be the wristband 108, the electronic device 106, or any other desired device. The one or more processing devices 944 may be configured to calculate whether the number of steps satisfies a step threshold of a treatment plan 1302 for the user 2108. The one or more processing devices 944 may be configured to display, on a user interface 2000, the number of steps taken by the user 2108 and an indication of whether the number of steps satisfies the step threshold. The indication may include whether the number of steps is greater than, equal to, or less than the number of steps equal to the step threshold. The indication may also include information as to how many steps were taken over the step threshold, how many steps were required to meet the steps threshold, or any other desired information. The one or more processing devices 944 may be configured to display, on the clinical portal 126, the number of steps taken by the user 2108 and an indication of whether the number of steps satisfies the step threshold.

The one or more processing devices 944 may execute the instructions 3122 to prompt the user 2108 to enter or change a target value into the computing device 102 and cause the computing device 102 to present the target value. The one or more processing devices 944 may execute the instructions 3122 to prompt a second user, such as a clinician, to enter the target value into a second computing device 114 and cause the computing device 102 to present the target value. The target value may also be presented on the second computing device 114. The target value may include at least one of a first target value, a second target value, a first pain score, a second pain score, a pedal speed, and a mode (e.g., a pedaling mode, such as the passive mode 1304, the active-assisted mode 1306, the resistive mode 1308, and/or the active mode 1310). The target values may be the same as or different values from the threshold condition values (e.g., the force threshold 1730, the revolutions threshold 1732, the steps threshold, the vitals threshold, etc.), or any other desired value. For example, the first target value and/or the second target value may be one or more of a target heartrate, a target force that the user 2108 is to exert on the one or more pedals 110, a target range of motion of the first and/or second body parts 2112, 2114, a target position of the one or more pedals 110 on the radially-adjustable couplings 124, a target angle of flexion at the joint 2116, a target number of bends 2122 or extensions 2222, a target number of steps, or any other desired target value.

The first pain score may be received by the user input 1504. The first pain score may be a first level of pain that a user 2108 is experiencing at a first time, such as at or before the beginning of the user's rehabilitation session, or any other desired time, and wherein, for example, the pain occurs at the first body part 2112, the second body part 2114, and/or the joint 2116. The second pain score may be received by the user input 1904. The second pain score may be a second level of pain that the user 2108 is experiencing at a second time, such as during the rehabilitation session, after the rehabilitation session, or at any other desired time. The one or more processing devices 944 may further be configured to assign a score based on the target value and a performance of the user. For example, the score can be assigned based on user 2108 input, a performance of the user 2108 (for example, information included in the options 3004, 3006, 3008, 3010), or any other desired information.

In another aspect, a system for rehabilitation may include one or more electronic devices 106 comprising one or more memory devices 938 storing instructions 3122, one or more network interface cards 940, and one or more sensors 942. The one or more electronic devices 106 may be coupled to a user 2108. The system for rehabilitation may further include an electromechanical device 104 comprising an electrical motor 122 and one or more pedals 110. The system for rehabilitation may further include one or more processing devices 944 operatively coupled to the one or more memory devices 938, the one or more network interface cards 940, and the one or more sensors 942. The one or more processing devices 944 may be configured based on the configuration information for the pedaling session to execute the instructions 3122 to receive configuration information for a pedaling session and to set a resistance parameter and a maximum pedal force parameter (e.g., the force threshold 1730). A selection of the configuration information may be received from the user interface 2000 presented to the user 2108. The configuration information may be received from a server computing device (e.g., the server 128) that received the configuration information from a clinical portal 126 presented on a computing device 114. The configuration information may comprise configuration information specified for a stage of a plurality of stages in a treatment plan 1302 for rehabilitating a body part of the user 2108. The one or more processing devices 944 may further be configured to execute the instructions 3122 to measure force applied to the one or more pedals 110 of the electromechanical device 104 as a user 2108 pedals or otherwise engages the electromechanical device 104. Based on the resistance parameter, the electrical motor 122 may provide resistance during the pedaling session. The one or more processing devices 944 may further be configured to execute the instructions 3122 to determine whether the measured force exceeds a value of a maximum pedal force parameter and, responsive to determining that the measured force exceeds the value of the maximum pedal force parameter, to reduce the resistance parameter so the electrical motor 122 applies less resistance during the pedaling session to maintain a revolutions per time period threshold (e.g., the revolutions threshold 1732). Responsive to determining that the measured force does not exceed the value of the maximum pedal force parameter, the one or more processing devices 944 may execute the instructions 3122 to maintain the same maximum pedal force parameter during the pedaling session.

In yet another aspect, a system for rehabilitation may further include one or more electronic devices 106 comprising one or more memory devices 938 storing instructions 3122, one or more network interface cards 940, and one or more sensors 942. The one or more electronic devices 106 may be flexible and worn by a user. The system for rehabilitation may further include one or more processing devices 944 operatively coupled to the one or more memory devices 938, the one or more network interface cards 940, and the one or more sensors 942. The one or more processing devices 944 may further be configured to execute the instructions 3122 to receive, from the one or more electronic devices 106, a plurality of angles of extension 2218 between an upper leg and a lower leg at a knee of the user. The plurality of angles 2102 may be measured as the user 2108 extends the lower leg away from the upper leg via the knee.

The one or more electronic devices 106 may be one or more goniometers or any other device configured to detect, acquire, or measure parameters of the user, for example, via the one or more sensors 942. The parameters may include the user's movement, temperature, number of steps, angles of extension or bend of body parts, or any other desired parameter. For example, one electronic device may be worn by a user on the upper leg and another electronic device on the lower leg. The one electronic device may be bendably connected to the second electronic device, for example. Each electronic device may include one or more sensors 942. The one or more sensors 942 may be configured to measure joint flexion. For example, the sensors may include accelerometers, flex sensors, magnets, or any other type of sensors. The one or more electronic devices 106 may include portions, such as arms, that are bendable or flexible. For example, the arms may have portions that can bend and move with the one or more body parts about the respective joint.

The one or more processing devices 944 may be configured to execute the instructions 3122 to present, on a user interface 2000, a graphical animation 2104 of the upper leg, the lower leg, and the knee of the user 2108 as the lower leg is extended away from the upper leg via the knee. The graphical animation 2104 may include the plurality of angles of extension 2218 as the plurality of angles of extension 2218 changes during the extension 2222. The one or more processing devices 944 may further be configured to execute the instructions 3122 to store a smallest angle of the plurality of angles of extension 2218 as an extension statistic for an extension session, wherein a plurality of extension statistics may be stored for a plurality of extension sessions specified by the treatment plan 1302. The one or more processing devices 944 may further be configured to execute the instructions 3122 to present throughout the treatment plan 1302 via a graphical element on the user interface 2000 presenting the plurality of extension statistics progress of the plurality of extension sessions. The graphical element may be a graph 2204, a bar chart 2110, text, numbers, or any other desired graphics. The one or more processing devices 944 may further be configured to execute the instructions 3122 to determine, based on the plurality of angles of extension 2218, whether a range of motion threshold condition is satisfied. Responsive to determining that the range of motion threshold condition is satisfied, the one or more processing devices 944 may transmit, via the one or more network interface cards 940, a threshold condition update to a second computing device 114 to cause the second computing device 114 to present the threshold condition update. The threshold condition update may be presented in the clinical portal 126, the user portal 118, or in any other desired computing device.

Clause 1. A system for rehabilitation, comprising:
one or more electronic devices comprising one or more memory devices storing instructions, one or more network interface cards, and one or more sensors, wherein the one or more electronic devices are coupled to a user; and
one or more processing devices operatively coupled to the one or more memory devices, the one or more network interface cards, and the one or more sensors, wherein the one or more processing devices execute the instructions to:
receive information from the one or more sensors; and
transmit, via the one or more network interface cards, the information to a computing device controlling an electromechanical device.

Clause 2. The system of any preceding clause, wherein the information is received while a user is engaging one or more pedals of the electromechanical device.

Clause 3. The system of any preceding clause, wherein the one or more processing devices are further configured to transmit, via the one or more network interface cards, the information to a second computing device to cause the second computing device to present the information.

Clause 4. The system of any preceding clause, wherein the information comprises a plurality of angles, wherein the plurality of angles comprises at least one of angles of extension of a first body part of a user extended away from a second body part at a joint and angles of bend of the first body part retracting closer toward the second body part.

Clause 5. The system of any preceding clause, wherein the transmitting the plurality of angles to the computing device causes the computing device to:
adjust a first position of a first pedal on a first radially-adjustable coupling of the electromechanical device, wherein the adjusting of the first position changes a first diameter of a first range of motion of the first pedal; and
maintain a second diameter of a second range of motion of a second pedal on a second radially-adjustable coupling of the electromechanical device.

Clause 6. The system of any preceding clause, wherein at least one of the angles of extension and the angles of bend satisfies a range of motion threshold condition to cause the adjustment of the first position.

Clause 7. The system of any preceding clause, wherein the transmitting the plurality of angles to the computing device causes the computing device to:
adjust a first position of a first pedal on a first radially-adjustable coupling of the electromechanical device, wherein the adjusting of the first position changes a first diameter of a first range of motion of the first pedal; and
adjust a second position of a second pedal on a second radially-adjustable coupling of the electromechanical device, wherein the adjusting of the second position changes a second diameter of a second range of motion of the second pedal.

Clause 8. The system of any preceding clause, wherein at least one of the angles of extension and the angles of bend satisfies a range of motion threshold condition to cause the adjustments of the first and second positions.

Clause 9. The system of any preceding clause, wherein the first body part is a lower leg, the second body part is an upper leg, and the joint is a knee; and wherein the one or more electronic devices are configured for coupling to the lower leg and the upper leg, and for flexing adjacent to the knee.

Clause 10. The system of any preceding clause, wherein the transmitting the plurality of angles to the computing device causes the computing device to present the plurality of angles in a graphical animation of the first body part and the second body part, each moving in real-time during the extension or the bend.

Clause 11. The system of any preceding clause, wherein the one or more processing devices executes the instructions to:
select a number of extensions or a number of bends; and
transmit, via the one or more network interface cards, the number of extensions or the number of bends to a second computing device, wherein the transmitting the number of extensions or the number of bends to the second computing device causes the second computing device to present the respective number of extensions or the number of bends.

Clause 12. The system of any preceding clause, wherein the one or more sensors are worn by the user, and wherein the one or more processing devices are further configured to:
present, on a user interface of a control system, a graphical animation of a first body part, a second body part, and a joint of a user as the first body part is extended away from the second body part via the joint, wherein the graphical animation includes a plurality of angles of extension as the plurality of angles of extension changes during the extension;

store a smallest angle of the plurality of angles of extension as an extension statistic for an extension session, wherein a plurality of extension statistics is stored for a plurality of extension sessions specified by a treatment plan; and present, throughout the treatment plan, via a graphical element on the user interface, a progress of the plurality of extension sessions.

Clause 13. The system of any preceding clause, wherein the one or more sensors are worn by the user, and wherein the one or more processing devices are further configured to:

present, on a user interface of a control system, a graphical animation of a first body part, a second body part, and a joint of a user as the first body part is retracted closer to the second body part via the joint, wherein the graphical animation includes a plurality of angles of bend as the plurality of angles of bend changes during the bend;

store a largest angle of the plurality of angles of bend as a bend statistic for a bend session, wherein a plurality of bend statistics is stored for a plurality of bend sessions specified by a treatment plan; and present, throughout the treatment plan, via a graphical element on the user interface, a progress of the plurality of bend sessions.

Clause 14. The system of any preceding clause, wherein the one or more processing devices are further configured to:

control an image capture device to capture an image of a body part of a user being rehabilitated; and transmit, to a computing device operated by a clinician, the image of the body part, wherein the computing device is communicatively coupled to the control system.

Clause 15. The system of any preceding clause, wherein the one or more processing devices are further configured to:

receive, from a wearable device, a number of steps taken by a user over a certain time period;

calculate whether the number of steps satisfies a step threshold of a treatment plan for the user; and display, on a user interface, the number of steps taken by the user and an indication of whether the number of steps satisfies the step threshold.

Clause 16. The system of any preceding clause, wherein the one or more processing devices executes the instructions to:

prompt a second user to enter a target value into a second computing device; and cause the computing device to present the target value.

Clause 17. The system of any preceding clause, wherein the target value includes at least one of a first target value, a second target value, a first pain score, a second pain score, a pedal speed, and a mode.

Clause 18. The system of any preceding clause, wherein the one or more processing devices are further configured to assign a score based on the target value and a performance of the user.

Clause 19. A system for rehabilitation, comprising:

one or more electronic devices comprising one or more memory devices storing instructions, one or more network interface cards, and one or more sensors, wherein the one or more electronic devices are coupled to a user;

an electromechanical device comprising an electric motor and one or more pedals; and one or more processing devices operatively coupled to the one or more memory devices, the one or more network interface cards, and the one or more sensors, wherein the one or more processing devices execute the instructions to:

receive configuration information for a pedaling session;

based on the configuration information for the pedaling session, set a resistance parameter and a maximum pedal force parameter;

measure force applied to the one or more pedals of the electromechanical device as a user pedals the electromechanical device, wherein, based on the resistance parameter, the electric motor provides resistance during the pedaling session;

determine whether the measured force exceeds a value of the maximum pedal force parameter; and responsive to determining that the measured force exceeds the value of the maximum pedal force parameter, reduce the resistance parameter so the electric motor applies less resistance during the pedaling session to maintain a revolutions per time period threshold.

Clause 20. The system of any preceding clause, wherein the one or more processing devices execute the instructions to:

responsive to determining that the measured force does not exceed the value of the maximum pedal force parameter, maintain, during the pedaling session, the same maximum pedal force parameter.

Clause 21. The system of any preceding clause, wherein the configuration information is received from a server computing device that received the configuration information from a clinical portal presented on a computing device.

Clause 22. The system of any preceding clause, wherein the configuration information comprises configuration information specified for a stage of a plurality of stages in a treatment plan for rehabilitating a body part of the user.

Clause 23. The system of any preceding clause, further comprising receiving a selection of the configuration information from the user interface presented to the user.

Clause 24. A system for rehabilitation, comprising:

one or more electronic devices comprising one or more memory devices storing instructions, one or more network interface cards, and one or more sensors, wherein the one or more electronic devices are flexible and worn by a user; and one or more processing devices operatively coupled to the one or more memory devices, the one or more network interface cards, and the one or more sensors, wherein the one or more processing devices execute the instructions to:

receive, from the one or more electronic devices, a plurality of angles of extension between an upper leg and a lower leg at a knee of the user, wherein the plurality of angles is measured as the user extends the lower leg away from the upper leg via the knee;

present, on a user interface, a graphical animation of the upper leg, the lower leg, and the knee of the user as the lower leg is extended away from the upper leg via the knee, wherein the graphical animation includes the plurality of angles of extension as the plurality of angles of extension changes during the extension;

store a smallest angle of the plurality of angles of extension as an extension statistic for an extension session, wherein a plurality of extension statistics is stored for a plurality of extension sessions specified by the treatment plan;

present progress of the plurality of extension sessions throughout the treatment plan via a graphical element presenting the plurality of extension statistics on the user interface;

based on the plurality of angles of extension, determine whether a range of motion threshold condition is satisfied; and responsive to determining that the range of motion threshold condition is satisfied, transmit, via the one or more network interface cards, a threshold condition update to a second computing device to cause the second computing device to present the threshold condition update.

No part of the description in this application should be read as implying that any particular element, step, or function is an essential element that must be included in the claim scope. The scope of patented subject matter is defined only by the claims. Moreover, none of the claims is intended to invoke 35 U.S.C. § 112(f) unless the exact words "means for" are followed by a participle.

The foregoing description, for purposes of explanation, use specific nomenclature to provide a thorough understanding of the described embodiments. However, it should be apparent to one skilled in the art that the specific details are not required in order to practice the described embodiments. Thus, the foregoing descriptions of specific embodiments are presented for purposes of illustration and description. They are not intended to be exhaustive or to limit the described embodiments to the precise forms disclosed. It should be apparent to one of ordinary skill in the art that many modifications and variations are possible in view of the above teachings.

The above discussion is meant to be illustrative of the principles and various embodiments of the present invention. Once the above disclosure is fully appreciated, numerous variations and modifications will become apparent to those skilled in the art. It is intended that the following claims be interpreted to embrace all such variations and modifications.

What is claimed is:

1. A system for rehabilitation, comprising:
   one or more electronic devices comprising one or more memory devices storing instructions, one or more network interface cards, and one or more sensors, wherein the one or more electronic devices are coupled to a user;
   an electromechanical device comprising an electric motor and one or more pedals; and
   one or more processing devices operatively coupled to the one or more memory devices, the one or more network interface cards, and the one or more sensors, wherein the one or more processing devices execute the instructions to:
   receive configuration information for a pedaling session;
   based on the configuration information for the pedaling session, set a resistance parameter and a maximum pedal force parameter;
   measure force applied to the one or more pedals of the electromechanical device as a user pedals the electromechanical device, wherein, based on the resistance parameter, the electric motor provides resistance during the pedaling session;
   determine whether the measured force exceeds a value of the maximum pedal force parameter;
   responsive to determining that the measured force exceeds the value of the maximum pedal force parameter, reduce the resistance parameter so the electric motor applies less resistance during the pedaling session to maintain a revolutions per time period threshold;
   receive information from the one or more sensors of the one or more electronic devices coupled to the user, wherein the information comprises a plurality of angles of extension or retraction of a body part of the user; and
   based on the information, control operation of at least one controllable portion of the electromechanical device.

2. The system of claim 1, wherein the one or more processing devices execute the instructions to:
   responsive to determining that the measured force does not exceed the value of the maximum pedal force parameter, maintain, during the pedaling session, the same maximum pedal force parameter.

3. The system of claim 1, wherein the configuration information is received from a server computing device that received the configuration information from a clinical portal presented on a computing device.

4. The system of claim 1, wherein the configuration information comprises configuration information specified for a stage of a plurality of stages in a treatment plan for rehabilitating a body part of the user.

5. The system of claim 1, further comprising receiving a selection of the configuration information from the user interface presented to the user.

* * * * *